United States Patent
Bamdad

(10) Patent No.: US 10,724,027 B2
(45) Date of Patent: Jul. 28, 2020

(54) METHOD FOR MAKING PLURIPOTENT STEM CELLS

(71) Applicant: Minerva Biotechnologies Corporation, Waltham, MA (US)

(72) Inventor: Cynthia Bamdad, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

(21) Appl. No.: 14/029,651

(22) Filed: Sep. 17, 2013

(65) Prior Publication Data

US 2014/0178963 A1 Jun. 26, 2014
US 2020/0190502 A9 Jun. 18, 2020

Related U.S. Application Data

(63) Continuation of application No. PCT/US2012/029706, filed on Mar. 19, 2012.

(60) Provisional application No. 61/453,917, filed on Mar. 17, 2011, provisional application No. 61/472,516, filed on Apr. 6, 2011, provisional application No. 61/471,236, filed on Apr. 4, 2011.

(51) Int. Cl.

| | |
|---|---|
| *C07K 16/00* | (2006.01) |
| *C12N 11/06* | (2006.01) |
| *C07K 16/28* | (2006.01) |
| *C12Q 1/6881* | (2018.01) |
| *C12N 5/074* | (2010.01) |
| *C12N 5/0735* | (2010.01) |
| *A61K 31/7088* | (2006.01) |
| *C07K 16/30* | (2006.01) |

(52) U.S. Cl.
CPC .......... *C12N 11/06* (2013.01); *A61K 31/7088* (2013.01); *C07K 16/2863* (2013.01); *C07K 16/3092* (2013.01); *C12N 5/0606* (2013.01); *C12N 5/0696* (2013.01); *C12Q 1/6881* (2013.01); *C07K 2317/35* (2013.01); *C07K 2317/75* (2013.01); *C12N 2500/98* (2013.01); *C12N 2501/115* (2013.01); *C12N 2501/727* (2013.01); *C12N 2533/50* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2012/0156246 A1* 6/2012 Bamdad .................... 424/277.1

FOREIGN PATENT DOCUMENTS

| WO | WO 2009105570 | * | 7/2009 |
| WO | WO 2010/042562 A2 | | 4/2010 |
| WO | WO 2010/042891 A2 | | 4/2010 |
| WO | WO 2010/144887 A1 | | 12/2010 |

OTHER PUBLICATIONS

Hikita, Sherry et al., "MUC1* mediates the growth of human pluripotent stem cells," Plos One, Public Library of Science, US, 3(10):E3312, Oct. 3, 2008.

Smagghe, Benoit et al., "MUC1* Ligand, NM23-H1, Is a Novel Growth Factor That Maintains Human Stem Cells in a More Naïve State," Plos One, 8(3):e58601, Mar. 7, 2013.

Mahanta, Sanjeev et al., "A minimal fragment of MUC1 mediates growth of cancer cells," Plos One, Public Library of Science, US, 3(4):E2054.1-E2054.12, Apr. 30, 2008.

* cited by examiner

*Primary Examiner* — Michail A Belyavskyi
(74) *Attorney, Agent, or Firm* — Nixon & Vanderhye P.C.

(57) ABSTRACT

The present application discloses a method for inducing cells to gain characteristics of naïve stem cell state comprising culturing the cells in the presence of a MUC1* activator.

6 Claims, 44 Drawing Sheets
Specification includes a Sequence Listing.

| Surface:<br>Vita + 2D6C8 – no ROCi<br>Source:<br>H9s NM23 from feeders<br>Media Post – 8nM NM23-MM<br><br>• Day 1: plated<br>• Day 5: 4 ES organized colonies; no differentiation<br>• Day 8: 3 fully formed colonies, beginning to differentiate at edge; area of propagating single ES cells<br>• Day 9: these colonies harvested & passaged onto Vita + 2D6C8<br>• Day 13: 2 fully undifferentiated colonies growing | Surface:<br>Vita + 2D6C3 – no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells | Surface:<br>Vita + 2D6C8 – no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells |
|---|---|---|
| Surface:<br>Vita Alone – no ROCi<br>Source:<br>H9s NM23 from feeders<br>Media Post – 8nM NM23-MM<br><br>• Day 1: Plated<br>• Day 5: 4 colonies look like they may differentiate – no organized center<br>• Day 8: 3 colonies differentiated | Surface:<br>Vita Alone – no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells | Surface:<br>Vita Alone – no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells |

Fig. 1

| Plating Volume 1 ml – no growth factor in plating media<br>Time to correct volume and add NM23<br>T = 15 min<br><br>• Day 3: 14 colonies<br>• Day 6: 5-7 colonies mixture of fully undifferentiated, some edges differentiating, and some fully differentiated | Plating Volume 1 ml – no growth factor in plating media<br>Time to correct volume and add NM23<br>T = 30 min<br><br>• Day 3: 5 colonies<br>• Day 6: 5-7 colonies mixture of fully undifferentiated, some edges differentiating, and some fully differentiated | Plating Volume 1 ml – no growth factor in plating media<br>Time to correct volume and add NM23<br>T = 1 hr<br><br>• Day 3: 8 colonies<br>• Day 6: 5-7 colonies mixture of fully undifferentiated, some edges differentiating, and some fully differentiated |
|---|---|---|
| Plating Volume 1 ml – no growth factor in plating media<br>Time to correct volume and add NM23<br>T = 3 hrs<br><br>• Day 3: 8 colonies<br>• Day 6: 5-7 colonies mixture of large fully undifferentiated, some edges differentiating, and some fully differentiated | Plating Volume 1 ml – no growth factor in plating media<br>Time to correct volume and add NM23<br>T = 12 hrs<br><br>• Day 3: colonies<br>• Day 6: 5-7 colonies –do not look as good as T<O/N - mixture of fully undifferentiated, some edges differentiating, and some fully differentiated | Plating Volume 1 ml – no growth factor in plating media<br>Time to correct volume and add NM23<br>T = 24 hrs<br><br>• Day 3: 6 colonies<br>• Day 6: 5-7 colonies – do not look as good as T<O/N - mixture of fully undifferentiated, some edges differentiating, and some fully differentiated |

Fig. 5

| Surface:<br>Vita + 2D6C8-no ROCi<br>Source 1:<br>iPS NM23 on Matrigel<br>Media Post – 8nM NM23-MM<br><br>• Day 1: Plated<br>• Day 3: 2-3 undifferentiated colonies<br>• Day 6: 5-6 colonies undifferentiated, centers beginning to differentiate | Surface:<br>Vita + 2D6C3-no ROCi<br>Source 1:<br>iPS NM23 on Matrigel<br>Media Post – 8nM NM23-MM<br><br>• Day 1: Plated<br>• Day 3: 2-3 undifferentiated colonies<br>• Day 6: 5-6 colonies undifferentiated, centers beginning to differentiate | Surface:<br>Vita + 2D6C8-no ROCi<br>Source: 2<br>iPS FGF on MEF Feeders<br>Media Post – 8nM NM23-MM<br><br>• Day 1: Plated<br>• Day 3: 0 all floating<br>• Day 6: 6-7 colonies undifferentiated, centers beginning to differentiate |
|---|---|---|
| Surface:<br>Vita Alone – no ROCi<br>Source 1:<br>iPS NM23 on Matrigel<br>Media Post – 8nM NM23-MM<br><br>• Day 1: Plated<br>• Day 3: 2-3 undifferentiated colonies<br>• Day 6: 8-9 colonies mixture undifferentiated and differentiated | Surface:<br>Vita Alone – no ROCi<br>Source 2: iPS FGF on Feeders<br>Media Post – 8nM NM23-MM<br><br>• Day 1: Plated<br>• Day 3: 0 all floating<br>• Day 6: 5-6 colonies mixture undifferentiated and differentiated | Surface:<br>Vita + 2D6C3-no ROCi<br>Source: 2 iPS FGF on Feeders<br>Media Post – 8nM NM23-MM<br><br>• Day 1: Plated<br>• Day 3: 0 all floating<br>• Day 6: 5-6 colonies mixture undifferentiated and differentiated |

Fig. 8

| Surface:<br>Vita + 2D6C8<br>Source:<br>iPS NM23 on Matrigel<br>Media Post – 8nM NM23-MM<br><br>• Day 1: Plated<br>• Day 2: 2 undifferentiated colonies<br>• Day 4: 3-4 colonies undifferentiated or partially differentiated | Surface:<br>Vita + 2D6C3<br>Source:<br>iPS NM23 on Matrigel<br>Media Post – 8nM NM23-MM<br><br>• Day 1: Plated<br>• Day 2: 2 undifferentiated colonies<br>• Day 4: 3-4 colonies undifferentiated or partially differentiated | Surface:<br>Vita + ROC<br>Source:<br>iPS NM23 on Matrigel<br>Media Post – 8nM NM23-MM<br><br>• Day 1: Plated<br>• Day 2: 3 differentiated colonies<br>• Day 4: 3-4 colonies all partially or fully differentiated, slightly more differentiated than Vita + Ab No ROC |
|---|---|---|
| Surface:<br>Vita + 2D6C8<br>Source: H9s NM23 feeders<br>Media Post – 8nM NM23-MM<br><br>• Day 1: Plated<br>• Day 2: 3-4 small colonies, undifferentiated & partially differentiated<br>• Day 4: 8-10 colonies comparable or slightly more differentiated than Vita + ROC | Surface:<br>Vita + 2D6C3<br>Source: H9s NM23 feeders<br>Media Post – 8nM NM23-MM<br><br>• Day 1: Plated<br>• Day 2: 4-5 small colonies, undifferentiated & partially differentiated<br>• Day 4: 8-10 colonies comparable or slightly more differentiated than Vita + ROC | Surface:<br>Vita + ROC<br>Source: H9s NM23 feeders<br>Media Post – 8nM NM23-MM<br><br>• Day 1: Plated<br>• Day 2: 5-6 small undifferentiated colonies<br>• Day 4: 10-12 colonies mix of un and diff – only 3-4 still undifferentiated |

Fig. 10

2D6C3 Kappa Chain Variable Region

```
      ←―――――― FWR1 ――――――→ ←―――――― CDR1 ―――――→
      DIVITQTPLSLPVSLGDQASISCRSSQTIVHSNGNTYLE
      ←――――― FWR2 ―――――→ ←―CDR2―→ ←――――――――――
      WYLQKPGQSPKLLIYKVSNRFSGVPDRFSGSGSG
      ←―――――― FWR3 ――――――→ ←――― CDR3 ―――→
      TDFTLKINRVEAEDLGVYYCFQGSHVPFT       (SEQ ID NO:59)
```

Fig. 13

2D6C3 Heavy Chain Variable Region

| FWR1 | CDR1 |
EVMVVESGGGLVKPGGSLKLSCAASGFTFSGYAMSWVRQTPE
| FWR2 | CDR2 |
KRLEWVATISSGGTYIYYPDSVKGRFTISRDNAKNTLYLQMSSL
| FWR3 | CDR3 |
RSEDTAMYYCARLGGDNYYEY     (SEQ ID NO:60)

Fig. 14

2D6C8 Kappa Chain Variable Region

```
          ←———— FWR1 ————→ ←——— CDR1 ———→ ←
DIVITQTPASLAVSLGQRATISYRASKSVSTSGYSYMHWN
———— FWR2 ————→ ←— CDR2 —→ ←———— FWR3 ————
QQKPGQPPRLLIYLVSNLESGVPARFSGSGSGTDFTLNIH
→←——— CDR4 ———→
PVEEEDAATYYCQHIRELTRSE        (SEQ ID NO:61)
```

Fig. 15

2D6C8 Heavy Chain Variable Region

```
  ←———————— FWR1 ————————→←CDR1→←———
  EVMVVESGGGLVKPGGSLKLSCAASGFTFSGYAMSWVRQTPE
  FWR2 ———→←———— CDR2 ————→←————————
  KRLEWVATISSGGTYIYYPDSVKGRFTISRDNAKNTLYLQMSSL
  FWR3 ————————→←—— CDR3 ——→
  RSEDTAMYYCARLGGDNYYEY     (SEQ ID NO:62)
```

Fig. 16

3C2B1 Kappa Chain Variable Region

```
         FWR1                    CDR1
DIVLTQSPASLAVSLGQRATISCRASKSISTSDYNYIHWYQQK
   FWR2      CDR2              FWR3
PGQPPKLLIYLASNLESGVPARFSGSGSGTDFTLNIHPVEEED
         CDR3
AATYYCQHSRELPLTF    (SEQ ID NO:63)
```

Fig. 17

3C2B1 Heavy Chain Variable Region

<─────── FWR1 ───────> <─ CDR1 ─> <───
EVMLVESGGGLVKPGGSLKLSCAASGITFSTYTMSWVR
── FWR2 ──> <─── CDR2 ───> <────
QTPEKRLEWVATISTGGDKTYYSDSVKGRFTISRDNAK
───── FWR3 ─────> <── CDR3 ──>
NNLYLQMSSLRSEDTALYYCARGTTAMYYYAM  (SEQ ID NO:64)

Fig. 18

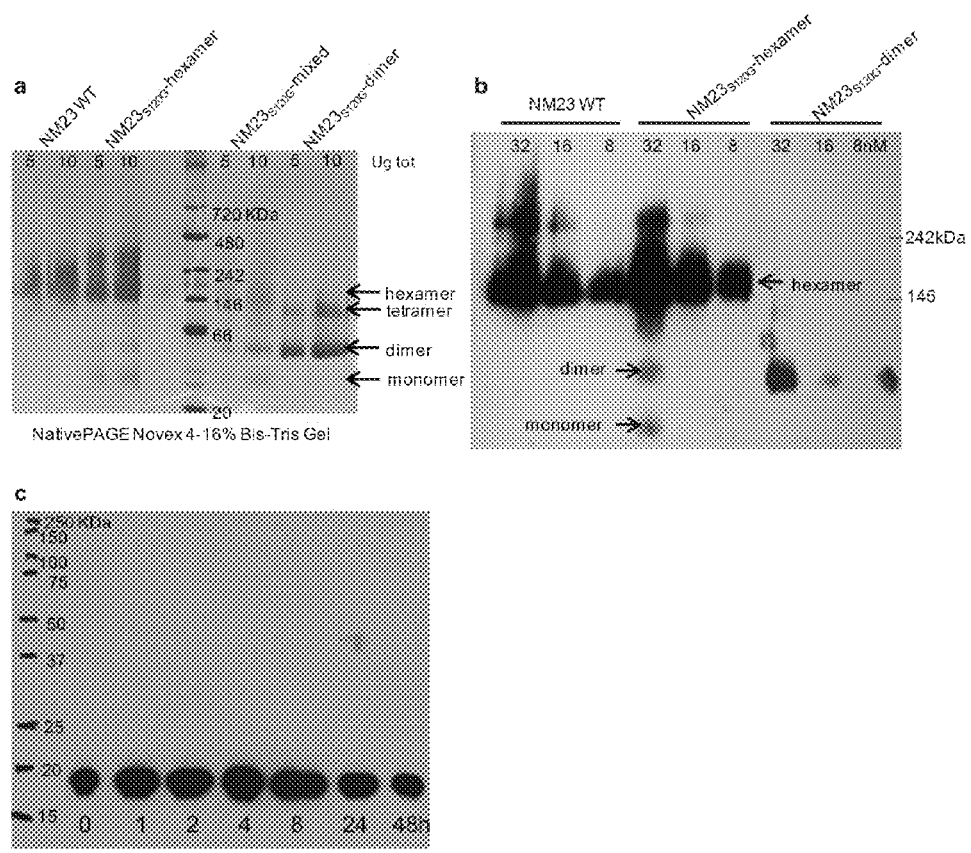
Fig. S22

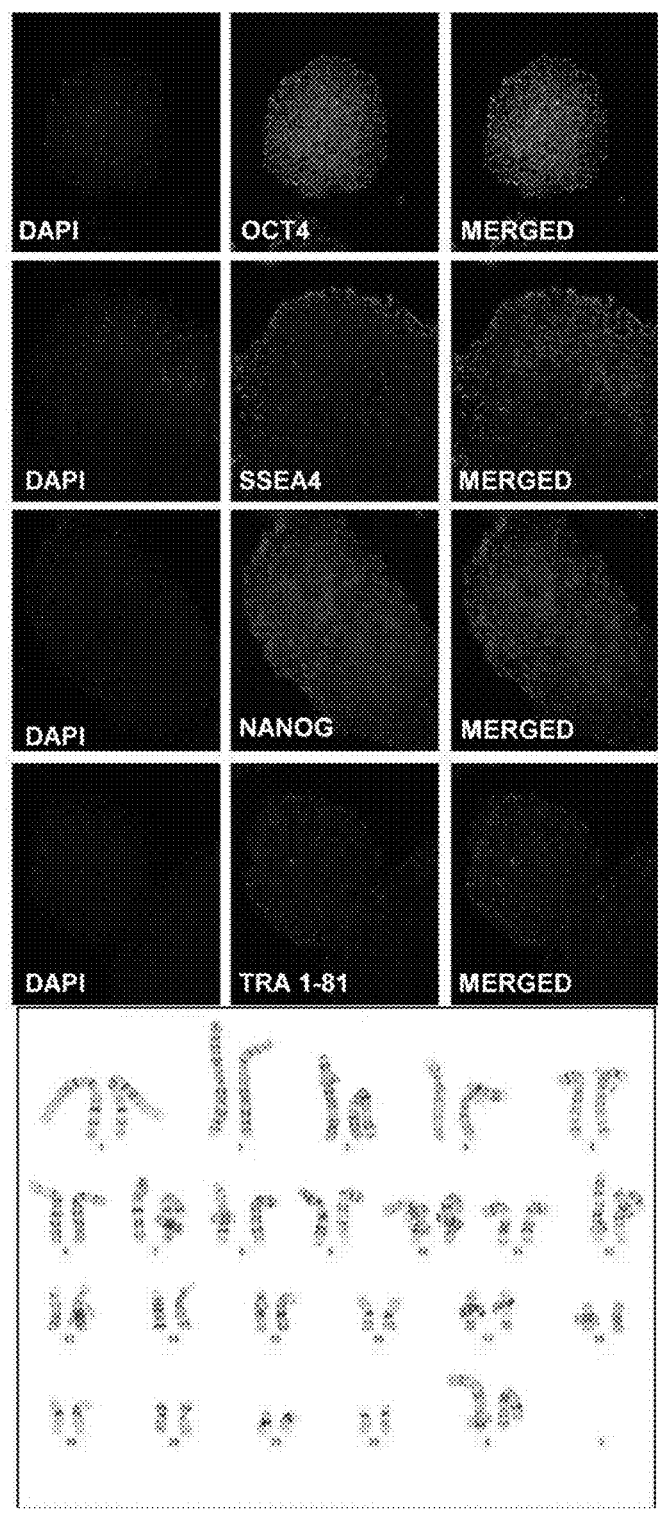
Fig. S24a

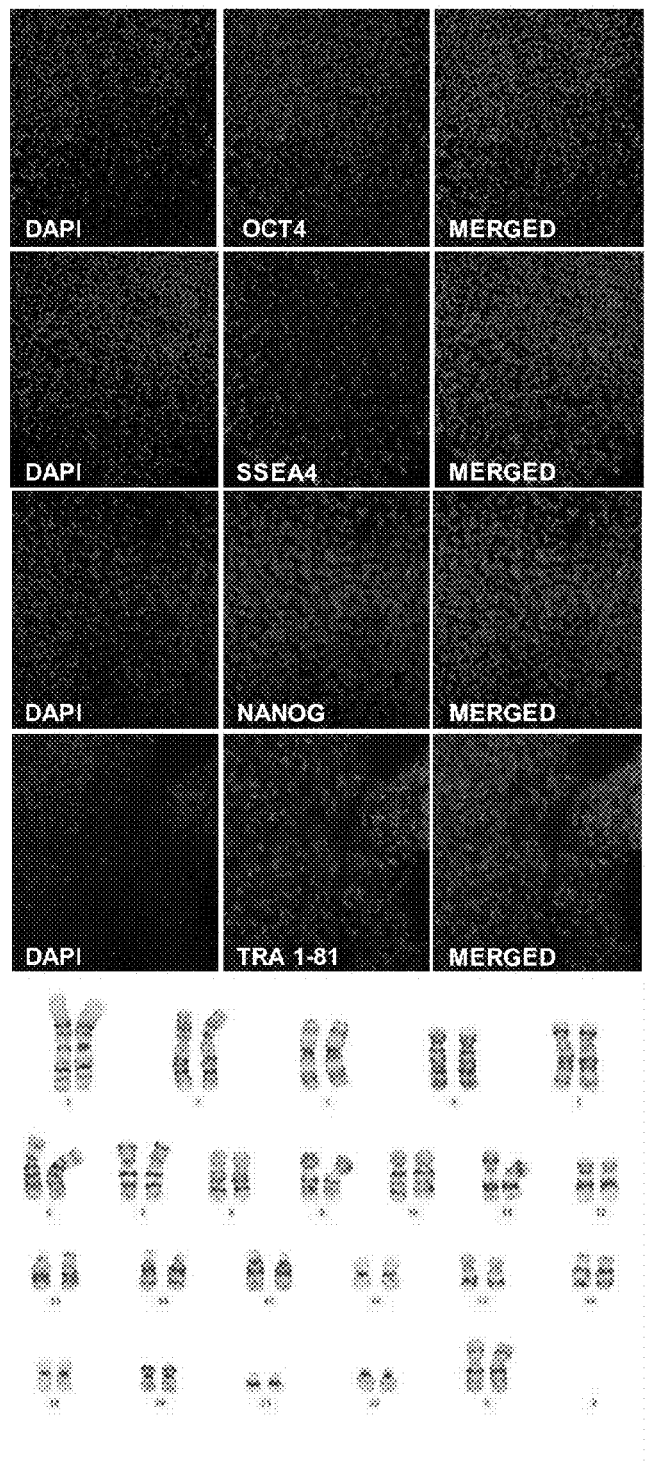
Fig. S24b

METHOD FOR MAKING PLURIPOTENT STEM CELLS

BACKGROUND OF THE INVENTION

Human stem cells have traditionally been grown over layers of feeder cells because fibroblast feeder cells secrete as yet unknown factors that increase growth and inhibit spontaneous differentiation of stem cells. Later, in an effort to develop defined surfaces that enable stem cell growth, Matrigel was identified as a surface coating that supported stem cell growth if used in conjunction with bFGF and conditioned media (cell secretions) from fibroblast feeder cells. In an improvement, the present inventor previously determined that conditioned media from feeder cells was not required for stem cell growth, on Matrigel, if the stem cell growth media contained a MUC1* activator such as bivalent anti-MUC1* antibody or NM23 in dimeric form, preferably a mutant, such as NM23-S120G that preferentially forms dimers, while resisting the characteristic formation of tetramers and hexamers.

However, although stem cell growth over a layer of Matrigel is an improvement over a cell-based surface, it is not a defined or xeno-free surface, which is the end goal for the growth of human stem cells destined for therapeutic use. Matrigel is a mixture of components that are not desirable for cells destined for human transplant. Matrigel contains among other things mouse sarcoma cells. Therefore, those in the field appreciate that what is needed is a surface for stem cell growth that is defined and preferably xeno-free (free of animal material).

Several surfaces that are defined and xeno-free have been reported and some are commercially available. Vita™ surface (ThermoFisher, USA), hydrogel coated surfaces, and recombinant Vitronectin have been reported to facilitate stem cell attachment and growth. However they still require the use of feeder cell conditioned media. In addition, the degree of stem cell attachment has in general been less than what Matrigel supports. Another problem that plagues this field is that whenever stem cell growth media or surfaces are changed, the stem cells must adapt gradually. This period of adaptation can take weeks to months to change stem cell media or growth surface.

Recent research indicates that the mechanical nature of a surface impacts a stem cell's ability to remain pluripotent. For example, rigid surfaces have been shown to induce differentiation whereas more flexible surfaces inhibit spontaneous differentiation. Pressure is another factor that affects stem cell differentiation or resistance to differentiation. In addition to the mechanical characteristics of surfaces, the chemical nature of a surface has been shown to affect differentiation. Further, it has been reported that stem cells of different stages of differentiation have different binding preferences. That is, stem cells at one stage may attach and grow on a surface having certain chemical characteristics while stem cells at another stage do not bind to the first surface but attach and grow on a second surface having different chemical makeup than the first surface.

Therefore it would be an improvement over existing methods to develop defined surfaces for human stem cell growth and maintenance that enable stem cell attachment, and also promote pluripotent stem cell growth. A further improvement to the state of the art would be if these defined growth surfaces bound to ligands known to promote pluripotency. An even further improvement would be if a surface and growth media were developed to make an entirely defined system for pluripotent stem cell growth, even more preferred if the system could be free of animal products. It would be a vast improvement over the state of the art if methods could be identified that streamline stem cell adaptation so that growth media or growth surfaces can be changed without the typical 4-8 week acclimation period.

Recently researchers (J. Nichols and A. Smith, *Cell Stem Cell* 4 (6), 487 (2009), J. Hanna, A. W. Cheng, K. Saha et al., *Proc Natl Acad Sci USA* 107 (20), 9222 (2010).) reported that human stem cells grown by conventional methods are not truly pluripotent stem cells, but have already undergone differentiation to a more mature state called "primed." Primed stem cells grow via the bFGF/TGF-beta pathway and closely resemble mouse stem cells derived from the epiblast rather than the "naïve" or "ground state" mouse stem cells that are derived from the inner cell mass. The consensus from the early research in the area of naïve versus primed human stem cells is that: 1) human naïve stem cells are not stable in the presence of bFGF; and 2) the growth factors or pathway by which human naïve stem cells grow is as yet unknown.

Research has now shown that human stem cells cultured in bFGF containing media are no longer truly pluripotent (J. Hanna, A. W. Cheng, K. Saha et al., *Proc Natl Acad Sci USA* 107 (20), 9222 (2010)). In a watershed research article, Jaenisch and colleagues describe human embryonic stem (ES) cells as being "primed" rather than being true pluripotent stem cells, which they term "Naïve". Research has now shown that human stem cells in the naïve state cannot be maintained in standard stem cell growth media wherein the major growth factor is bFGF.

By comparing human ES cells to mouse ES cells wherein both were derived from the blastocyst-stage embryos, the researchers discovered that the human ES cells were morphologically and molecularly different from the mouse stem cells. They further disclosed that the human ES cells that have been isolated thus far are not truly pluripotent and more closely resemble mouse stem cells that have been derived from the epiblast stage which is a later stage of development. These findings and others indicate that what we think of as human pluripotent ES cells are actually more mature than true pluripotent stem cells. Jaenisch and colleagues discovered molecular markers that identify naïve stem cells and markers that identify primed stem cells.

Researchers were able to temporarily make human primed stem cells revert to the naïve state by ectopic induction of Oct4, Klf4, and Klf2 factors combined with LIF and inhibitors of glycogen synthase kinase 3β (GSK3β) and mitogen-activated protein kinase (ERK1/2) pathway. Forskolin, a protein kinase A pathway agonist which can induce Forskolin, a protein kinase A pathway agonist which can induce Klf4 and Klf2 expression, transiently replaced the need for ectopic expression of those two genes. Once the human ES cells had been reverted to the naïve state, they needed to be cultured in PD/CH/LIF/FK but could only remain naïve for a few passages before they matured to primed cells. This is strong evidence that the researchers were not able to identify the growth factors that promote and maintain human ES cells in the pluripotent naïve state. In contrast to conventional human ESCs, these epigenetically converted naïve stem cells gained expression of Oct4, Nanog, Klf4, Klf2, Tbx3, Gbx2, Lin28 and SOCS3 (Naïve markers), and lost or had greatly reduced expression of Otx2, Sox17, Cer1, Foxa2, Zic1, Lhx2 and XIST (Primed markers). In addition, primed cells that were transiently reverted to the naïve state grew in sheets rather than in colonies.

However, Nichols and Smith report that the Naïve markers are Oct4, Nanog, Klf4, Klf2, Rex 1 and NrOb 1 and that naïve cells had lost or had greatly reduced expression of FGF5 and markers of X-inactivation such as XIST. The discrepancy between the lists of naïve markers and primed markers generated by these two research teams may be due differences in the naïve stem cells they were analyzing; Hanna et al analyzed primed human stem cells that they had transiently reverted to the naïve state, determined by their similarity to mouse naïve stem cells. Alternatively, genes identified by the earlier research may cause activation of the genes identified in the later, more extensive studies described in Hanna et al. Both studies agree that the naïve markers consist at least of Oct4, Nanog, Klf4 and Klf2, and the primed markers consist at least of FOXa2 and XIST.

Previous research has not been able to identify the growth pathway or the growth factor(s) that made human stem cells propagate as naïve stem cells. Further, even with ectopic expression of genes and growth in a concoction of factors, the reverted-naïve cells remained naïve for a short period of time and then progressed to the more differentiated primed stage.

It would be a significant improvement if one could identify methods for cultivating naïve stem cells. Such methods would include identification of the growth pathways that stimulate growth and maintenance of the naïve state, development of media that enables their proliferation, or identification of surfaces that naïve stem cells bind to for growth or isolation of naïve stem cells.

Therefore what is needed is a method for propagating human stem cells as naïve stem cells directly after harvest from either an embryo or from an induced pluripotent state, or a method to revert primed stem cells to the naïve state and then maintain them in that state for prolonged periods of time. What is needed is a method for stably converting primed stem cells to the naïve state, whereas current methods can only transiently hold the cells in the naïve state. Ideally, the method for maintaining human stem cells in the naïve state or converting them from the primed state to the naïve state would not involve ectopic expression of genes.

SUMMARY OF THE INVENTION

In one aspect, the present invention is directed to a method for inducing cells to gain characteristics of naïve stem cell state comprising culturing the cells in the presence of a MUC1* activator. The cells may be human cells, stem cells, human stem cells, progenitor cells, embryonic in origin or are induced to become more stem-like. The cells may be human cells derived from a blastocyst.

In this method, the MUC1* activator may be a dimeric or bivalent molecule, such as NM23 or an NM23 mutant or variant, or a bivalent antibody or antibody variant.

The cells may be cultured in the presence of human feeder cells or their secretions. The feeder cells may be fibroblasts or cancer cells, or the feeder cells are growth inactivated.

The present invention is also directed to a method for maintaining naïve stem cells in naïve stem cell state comprising culturing the cells in the presence of a MUC1* activator.

In another aspect, the present invention is directed to a method for establishing human stem cell lines comprising withdrawing cells from a blastocyst and culturing the cells in the presence of NM23 or dimeric NM23.

In yet another aspect, the present invention is directed to a method for inducing cells to gain characteristics of naïve stem cell state or maintaining the naïve stem cells in the naïve stem cell state comprising attaching the cells to be induced or cells possessing the naïve stem cell state to a stem proliferation surface lacking a feeder layer. The surface may include from at least about 0.5% Nitrogen (N), at least about a sum of Oxygen (O) and Nitrogen (N) of greater than or equal to 17.2%, and a contact angle of at least about 13.9 degrees. The surface may include 1.7-2.1% Nitrogen, 26.4-28.7% Oxygen and 28.2-30.7% Nitrogen and Oxygen combined, and wherein the surface has a contact angle of 14.3-18.8 degrees. The surface may be Vita™ surface (ThermoFisher, USA).

In yet another aspect, the invention is directed to a method for selecting for cells that have increased expression of naïve cell markers, comprising exposing a population of cells suspected of containing cells with increased expression of naïve markers to a stem proliferation surface lacking a feeder layer, and culturing the selected cells in the presence of the surface. The surface may include from at least about 0.5% Nitrogen (N), at least about a sum of Oxygen (O) and Nitrogen (N) of greater than or equal to 17.2%, and a contact angle of at least about 13.9 degrees. The surface may include 1.7-2.1% Nitrogen, 26.4-28.7% Oxygen and 28.2-30.7% Nitrogen and Oxygen combined, and wherein the surface has a contact angle of 14.3-18.8 degrees. The surface may be Vita™ surface (ThermoFisher, USA).

In any of method described above, the surface additionally may include an agent that binds to a cell surface molecule that is present on stem cells or progenitor cells. The cell surface molecule may be MUC1 or MUC1*. The cell surface molecule may be PSMGFR sequence. The agent may be an antibody. The antibody may be a polyclonal or monoclonal antibody that binds to PSMGFR. In particular, the monoclonal antibody may have the following Kappa Chain Variable Region CDR sequences:

```
                                   (SEQ ID NO: 20)
       CDR1: RSSQTIVHSNGNTYLE;

(SEQ ID NO: 21)
       CDR2: KVSNRFS;
       and (SEQ ID NO: 22)
       CDR3: FQGSHVPFT,
       or (SEQ ID NO: 26)
       CDR1: RASKSVSTSGYSYMH;

(SEQ ID NO: 27)
       CDR2: LVSNLES;
       and (SEQ ID NO: 28)
       CDR3: QHIRELTRSE.
```

According to the method above, the agent may be a polyclonal or monoclonal antibody that binds to SSEA1, SSEA4, Tra 1-60, Tra 1-81 or CD34. The mentioned agent may be NM23 or NM23 mutant or variant and is dimeric or bivalent.

In any of the above described methods, the methods may be carried out in the absence of a Rho kinase inhibitor. The methods may include trypsinizing the cells to single cells prior to plating on the surface. And the cells may be plated on the surface at a low density, such as between about $1 \times 10^3$ cells per $cm^2$ and $1 \times 10^4$ cells per $cm^2$ of a defined structure. In particular, the cells may be plated at about 5263 cells per $cm^2$ of a defined structure.

In another aspect, the methods may include plating the cells on the surface at a low volume of media, preferably a volume of media to just coat the surface, which volume of media may be between 0.1 and 0.2 mLs per cm² of a defined structure. The cells may be plated on the cells on the surface in the presence of EDTA. Further the method may include bringing the plated cells into close contact with the surface by application of force. The force may be centrifugal force.

In another aspect, the invention is directed to an article comprising a stem cell proliferation surface without feeder layer, to which is bound an agent that binds to a cell surface molecule that is present on stem cells or progenitor cells.

The surface may include from at least about 0.5% Nitrogen (N), at least about a sum of Oxygen (O) and Nitrogen (N) of greater than or equal to 17.2%, and a contact angle of at least about 13.9 degrees. The surface may be Vita or Vita-like surface. The cell surface molecule may be MUC1 or MUC1*. The cell surface molecule may be PSMGFR sequence. The agent may be an antibody. The antibody may be a polyclonal or monoclonal antibody that binds to PSMGFR. In particular, the monoclonal antibody may have the following Kappa Chain Variable Region CDR sequences:

```
                                    (SEQ ID NO: 20)?
CDR1: RSSQTIVHSNGNTYLE;

(SEQ ID NO: 21)?
CDR2: KVSNRFS;
and (SEQ ID NO: 22)?
CDR3: FQGSHVPFT,
or
                                    (SEQ ID NO: 26)?
CDR1: RASKSVSTSGYSYMH;

(SEQ ID NO: 27)?
CDR2: LVSNLES;
and
                                    (SEQ ID NO: 28)?
CDR3: QHIRELTRSE.
```

The agent may be a polyclonal or monoclonal antibody that binds to SSEA1, SSEA4, Tra 1-60, Tra 1-81 or CD34. The mentioned agent may be NM23 or NM23 mutant or variant and is dimeric or bivalent.

In another aspect, the invention include a method for identifying microRNAs signatures that are characteristic of the naïve stem cell state or the primed stem cell state comprising:

(i) culturing human embryonic stem cells or induced pluripotent stem cells in the presence of NM23 dimer or bivalent variants;

(ii) attaching the cells to a stem cell proliferation surface coated with a MUC1* antibody and allowing the cells to grow;

(iii) harvesting the cells and identifying microRNAs expressed from the stem cells of step (ii);

(iv) separately culturing human embryonic stem cells or induced pluripotent stem cells in bFGF-based media over a layer of murine feeder cells;

(v) harvesting the cells and identifying microRNAs expressed from the cells of step (iv);

(vi) comparing the microRNAs identified in step (iii) with the microRNAs identified in step (v);

(vii) identifying microRNAs unique to the naïve cell state by identifying those present or that have increased expression in step (iii) that are absent or have reduced expression in step (v); and (viii) identifying microRNAs unique to the primed cell state by identifying those present in step (v) that are absent or have reduced expression in step (iii).

The stem cell proliferation surface may be Vita or Vita-like surface.

In yet another aspect, the invention is directed to a method for identifying microRNAs signatures that are characteristic of the naïve stem cell state or the primed cell state comprising:

(i) culturing a first set and second set of human embryonic stem cells or induced pluripotent stem cells in the presence of NM23 dimer or bivalent variants;

(ii) attaching the cells to a first stem cell proliferation surface coated with a MUC1* antibody;

(iii) measuring the levels of microRNAs in the first set of cells;

(iv) harvesting the cells of the second identical set of cells, and plating the second set of cells onto second stem cell proliferation surface;

(v) allowing a period of growth over the second stem cell proliferation surface;

(vi) measuring the levels of microRNAs in the second set of cells;

(vii) identifying microRNAs unique to the naïve stem cell state comprising identifying those present or that have increased expression in the first set of cells and absent from or that have decreased expression in the second set of cells; and (viii) identifying microRNAs unique to the primed cell state by identifying those present or that have increased expression in the second set of cells and absent from or that have decreased expression in the first set of cells.

The first stem cell proliferation surface may be Vita or Vita-like surface, and the second stem cell proliferation surface may be Vitronectin.

In yet another aspect, the invention is directed to a method for inducing cells to gain characteristics of naïve stem cell state comprising introducing microRNAs that are characteristic of the naïve state to cells.

In yet another aspect, the invention is directed to a method for treating or preventing cancer in a patient, comprising administering to the patient, a protein or nucleic acid, which is upregulated when cells transition from the naïve state to a more differentiated state. The nucleic acid may be microRNA. The differentiated state of a cell may be the primed state.

In yet another aspect, the invention is directed to a method for culturing stem cells or progenitor cells on a stem cell proliferation surface comprising:

(a) obtaining a sample of the stem cells or progenitor cells;

(b) contacting the stem cells or progenitor cells to the surface; and (c) culturing the stem cells or progenitor cells in a media that contains a first agent that dimerizes MUC1*.

In yet another aspect, the invention is directed to a method for adapting stem cells or progenitor cells to bind to a surface comprising:

(a) pre-incubating the stem cells or progenitor cells in media that contains a first agent that dimerizes MUC1*; and (b) contacting the stem cells or progenitor cells to the surface.

The surface may include a second agent that dimerizes MUC1*.

The above method may further include the following steps after step (a), and before step (b), (a)(i) pelleting the stem cells or progenitor cells after incubation in the media that contains the first agent that dimerizes MUC1*;

(a)(ii) resuspending the stem cells or progenitor cells in media lacking the first agent;

(a)(iii) plating the stem cells or progenitor cells on the surface; and (a)(iv) waiting for a period of up to 48 hrs.

In yet another aspect, the invention is directed to a method for adapting stem cells to bind to a stem cell proliferation surface lacking a feeder layer, comprising pre-incubating the cells in media that contains an agent that dimerizes MUC1*, and then introducing the stem cells to the surface. The surface may include from at least about 0.5% Nitrogen (N), at least about a sum of Oxygen (O) and Nitrogen (N) of greater than or equal to 17.2%, and a contact angle of at least about 13.9 degrees.

The method above may include additional steps of:
(i) incubating the stem cells in media that contains an agent that dimerizes MUC1*;
(ii) subjecting the stem cells to a force that causes the cells to contact the surface before attaching to other cells;
(iii) resuspending the cells in media lacking the agent;
(iv) plating onto the surface;
(v) waiting period of up to 48 hrs; and
(vi) adding an agent that dimerizes MUC1*.

The surface may be Vita™ surface (ThermoFisher, USA). The force may be centrifugal force, pressure, or vacuum.

In yet another aspect, the invention is directed a kit comprising:

(i) an article comprising a stem cell proliferation surface without feeder layer, to which is bound an agent that binds to a cell surface molecule that is present on stem cells or progenitor cells; and (ii) stem cell growth media comprising minimal media with NM23.

The surface comprises from at least about 0.5% Nitrogen (N), at least about a sum of Oxygen (O) and Nitrogen (N) of greater than or equal to 17.2%, and a contact angle of at least about 13.9 degrees. The surface may be Vita™ surface (ThermoFisher, USA). The cell surface molecule may be MUC1 or MUC1*. The cell surface molecule may be PSMGFR sequence. The agent may be an antibody. The antibody may be a polyclonal or monoclonal antibody that binds to PSMGFR. In particular, the monoclonal antibody may have the following Kappa Chain Variable Region CDR sequences:

```
                             (SEQ ID NO: 20)
CDR1: RSSQTIVHSNGNTYLE;

(SEQ ID NO: 21)
CDR2: KVSNRFS;
and (SEQ ID NO: 22)
CDR3: FQGSHVPFT,
or (SEQ ID NO: 26)
CDR1: RASKSVSTSGYSYMH;

(SEQ ID NO: 27)
CDR2: LVSNLES;
and (SEQ ID NO: 28)
CDR3: QHIRELTRSE.
```

According to the method above, the agent may be a polyclonal or monoclonal antibody that binds to SSEA1, SSEA4, Tra 1-60, Tra 1-81 or CD34. The mentioned agent may be NM23 or NM23 mutant or variant and is dimeric or bivalent. The antibody may be humanized. And the minimal media may be xeno-free.

These and other objects of the invention will be more fully understood from the following description of the invention, the referenced drawings attached hereto and the claims appended hereto.

DESCRIPTION OF THE DRAWINGS

The present invention will become more fully understood from the detailed description given herein below, and the accompanying drawings which are given by way of illustration only, and thus are not limitative of the present invention, and wherein;

FIG. 1 is the experimental setup and noted results, shown in 6-well plate format, for the experiment described in Example 3 and for which images of the 6 wells are shown in FIGS. 2-4.

FIG. 5 is the experimental setup and noted results, shown in 6-well plate format, for another experiment described in Example 3 and for which images of the 6 wells are shown in FIGS. 6 and 7. The point of this experiment is to test if reducing media volume aids in the attachment of stem cells to surfaces and further if withholding MUC1* ligands from the media also aids in attachment of cells to the MUC1* antibodies on the surface.

FIG. 8 is the experimental setup and noted results, shown in 6-well plate format, for another experiment described in Example 3 and for which images of the 6 wells are shown in FIG. 9. In this experiment, 2 monoclonal anti-MUC1* antibodies are compared to a Vita surface alone. Human iPS cells from 2 different sources are tested: iPS cells that had previously been cultured in NM23-MM and iPS cells that had previously been cultured in bFGF plus MEF conditioned media, both over Matrigel.

FIG. 10 is the experimental setup and noted results, shown in 6-well plate format, for the experiment described in Example 4 and for which images of the 6 wells are shown in FIG. 11.

FIG. 13 shows amino acid sequence for the 2D6C3 Kappa Chain Variable Region. CDR1: RSSQTIVHSNGNTYLE (SEQ ID NO:20); CDR2: KVSNRFS (SEQ ID NO:21); and CDR3: FQGSHVPFT (SEQ ID NO:22).

FIG. 14 shows amino acid sequence for the 2D6C3 Heavy Chain Variable Region. CDR1: GYAMS (SEQ ID NO:23); CDR2: TISSGGTYIYYPDSVKG (SEQ ID NO:24); and CDR3: LGGDNYYEY (SEQ ID NO:25).

FIG. 15 shows amino acid sequence for the 2D6C8 Kappa Chain Variable Region. CDR1: RASKSVSTSGYSYMH (SEQ ID NO:26); CDR2: LVSNLES (SEQ ID NO:27); and CDR3: QHIRELTRSE (SEQ ID NO:28).

FIG. 16 shows amino acid sequence for the 2D6C8 Heavy Chain Variable Region. CDR1: GYAMS (SEQ ID NO:29); CDR2: TISSGGTYIYYPDSVKG (SEQ ID NO:30); and CDR3: LGGDNYYEY (SEQ ID NO:31).

FIG. 17 shows amino acid sequence for the 3C2B1 Kappa Chain Variable Region.
CDR1: RASKSISTSDYNYIH (SEQ ID NO:32); CDR2: LASNLES (SEQ ID NO:33); and CDR3: QHSRELPLTF (SEQ ID NO:34).

FIG. 18 shows amino acid sequence for the 3C2B1 Heavy Chain Variable Region. CDR1: TYTMS (SEQ ID NO:35); CDR2: TISTGGDKTYYSDSVKG (SEQ ID NO:36); and CDR3: GTTAMYYYAM (SEQ ID NO:37).

FIGS. S22a-c show gels and Western blots showing the multimerization state (a,b) of the various NM23 preparations and the stability of NM23-dimers (c).

FIGS. 23a-f show photos of experiment of Example 8 where human H9 ES cells that have been grown over Matrigel and cultured in either NM23-MM (top) or bFGF-MEF conditioned media (bottom) for 5 or more passages then allowed to differentiate by the embryoid body method, then stained for presence of the three germline markers plus the nuclear stain DAPI (blue). The figure shows that NM23 causes the stem cells to grow in such a way that they differentiate better than cells grown in bFGF as evidenced by cell morphology and their coordinated differentiation.

FIGS. 24a-l show graphs and photos of the experiments described in Example 9 showing that human ES and iPS cells undergo exponential growth on Vita-type surfaces that have been coated with an anti-MUC1* antibody and wherein the cells are cultured in a NM23-based media. Photos further show that after serial passaging, these cells differentiate down all three germlines FIGS. S24a and b show photos of immunocytocellular (ICC) staining for the presence of the pluripotency markers for the human ES (a) and iPS (b) cells shown in FIG. 24 and described in Example 9 and karyotyping analysis showing unchanged karyotype.

FIGS. 25a-d show graphs of RT-PCR experiments to measure the expression levels of naïve and primed markers for human ES cells grown under a variety of conditions which are described in Example 10.

FIGS. 26a-l show photos of human ES cells cultured in the presence or absence of a Rho kinase inhibitor (ROCi) wherein the stem cells were cultured in NM23-MN6. FIGS. 26m-t show images of human ES cells cultured in either NM23-MM or NM23-MN6 plus or minus the ROCi over a layer of Vitronectin.

Figure 27:
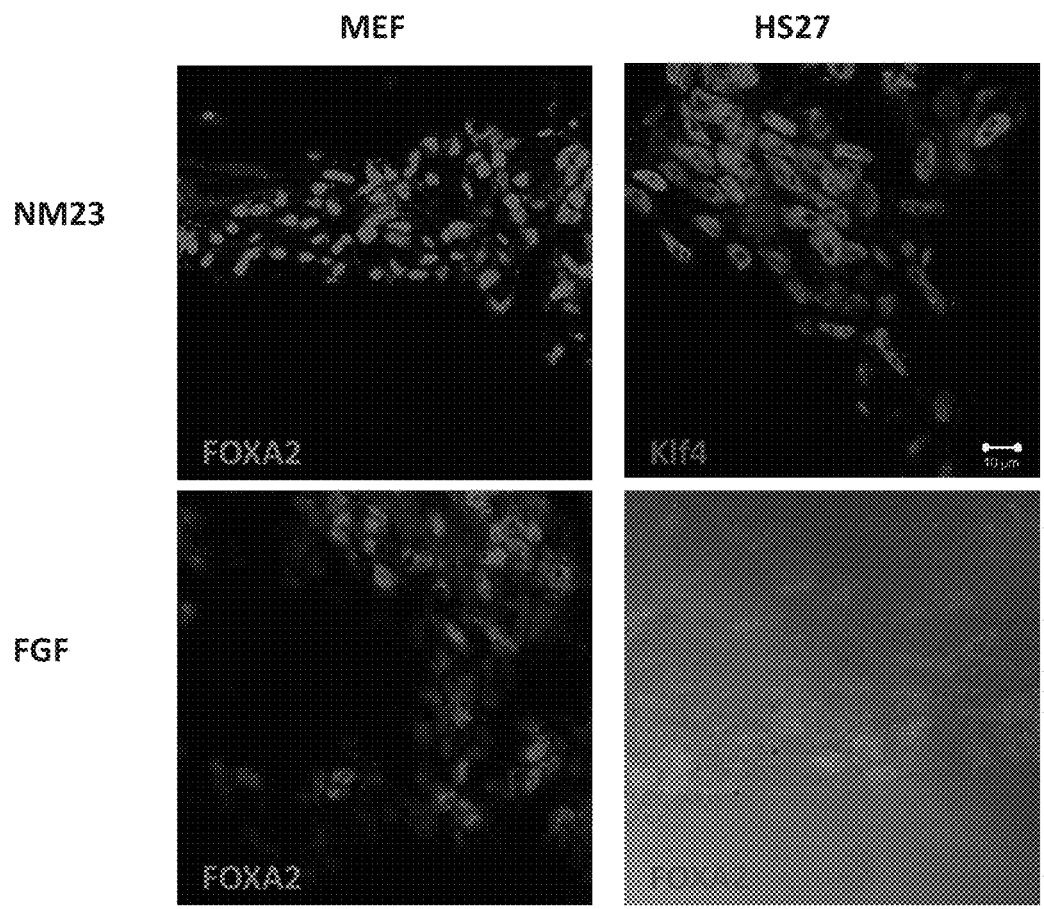

FIG. 27 shows images from a confocal microscope of H9 stem cells that have been grown in NM23-S120G over either human HS27 feeder cells or over mouse MEF feeder cells; also shows H9 stem cells that have been grown in bFGF over either human HS27 feeder cells or over mouse MEF feeder cells. Only NM23-S120G cultured cells grown over human feeders stained positive for Klf4 showing they are naïve. All other conditions produced primed stem cells and stained positive for Foxa2, a marker for primed cells.

Figure 28:
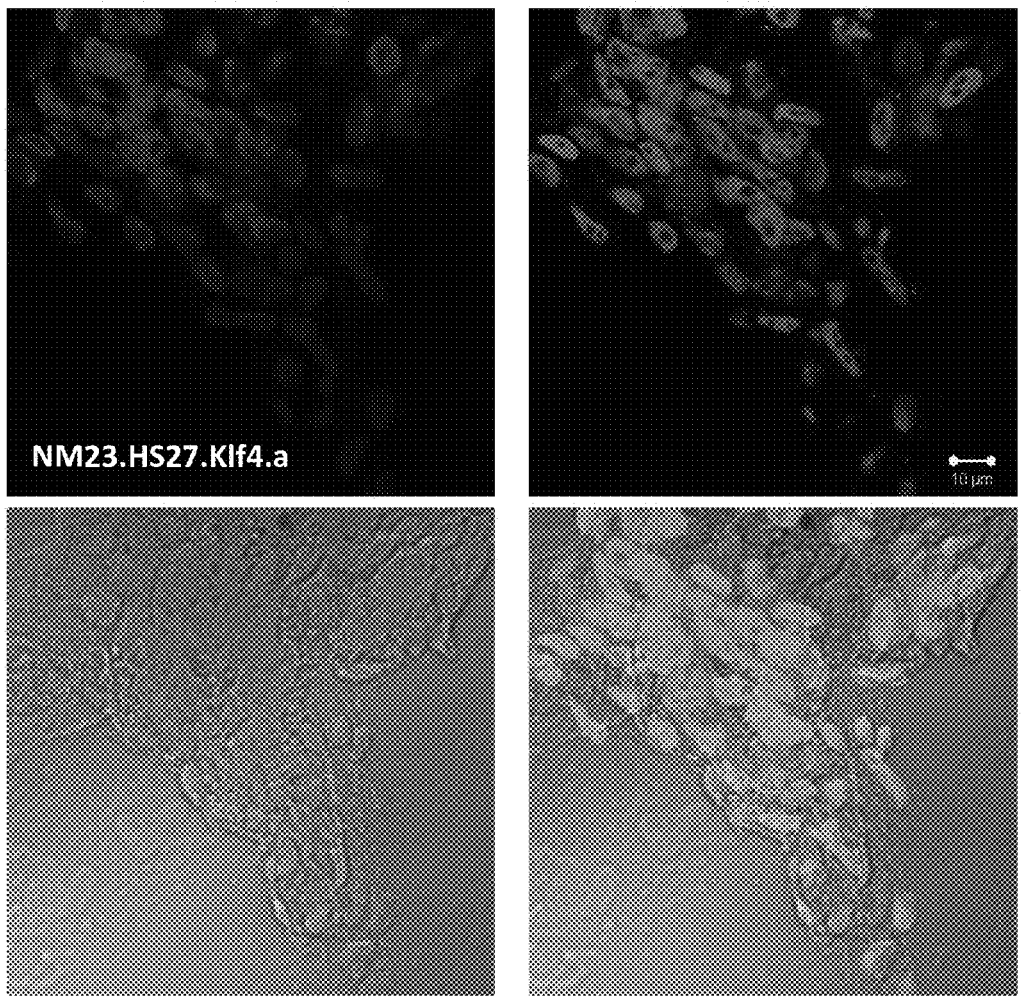

FIG. 28 is an image from a confocal microscope of H9 stem cells that have been grown in NM23-S120G over human feeder cells and stain positive for Klf4 which is a marker for naïve stem cells.

Figure 29:
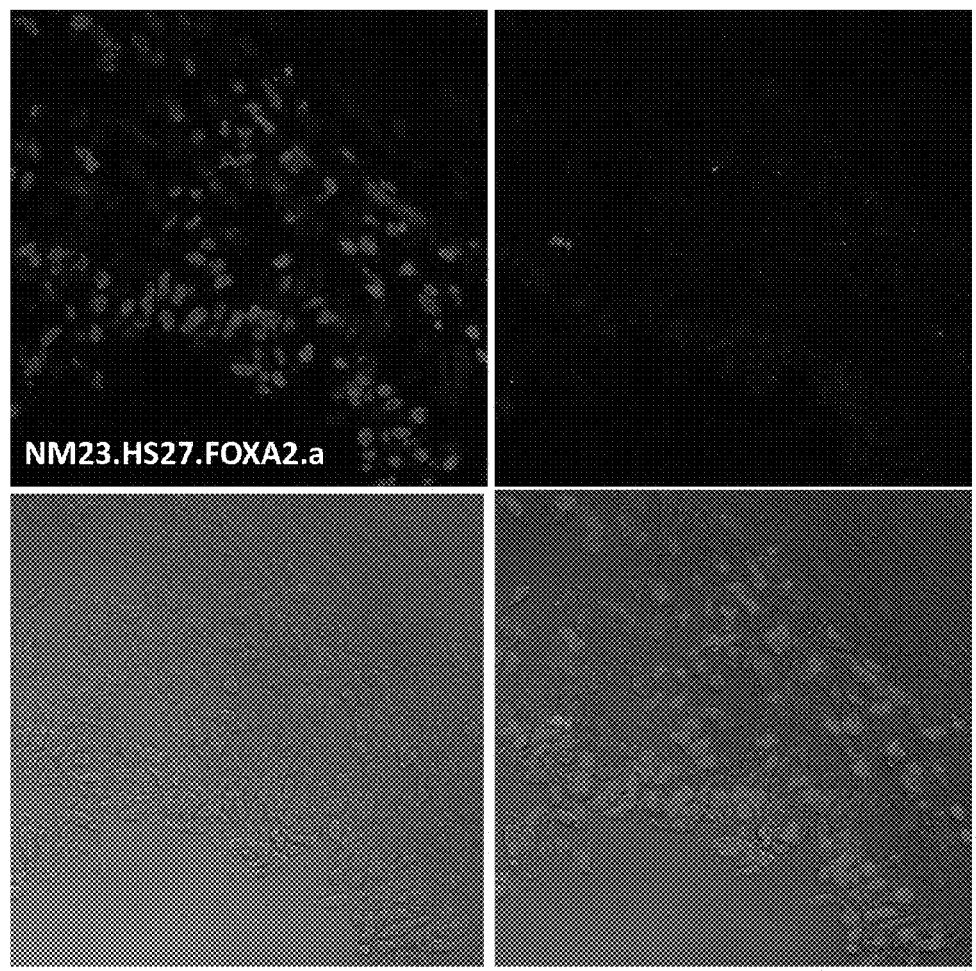

FIG. 29 is an image from a confocal microscope of H9 stem cells that have been grown in NM23-S120G over human feeder cells and shows they are negative for Foxa2 a marker for primed stem cells.

Figure 30:
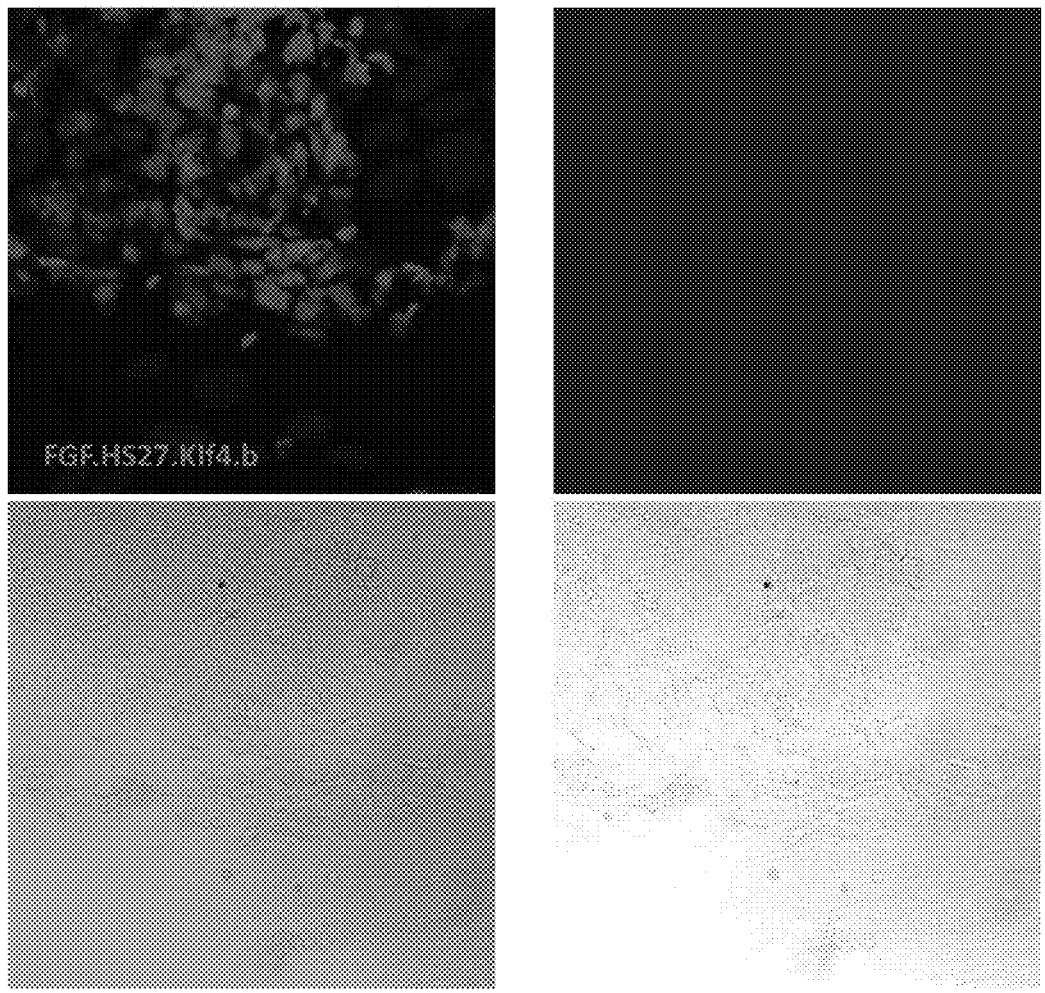

FIG. 30 is an image from a confocal microscope of H9 stem cells that have been grown in bFGF over human feeder cells and shows they are negative for Klf4 which is a marker for naïve stem cells.

Figure 31:
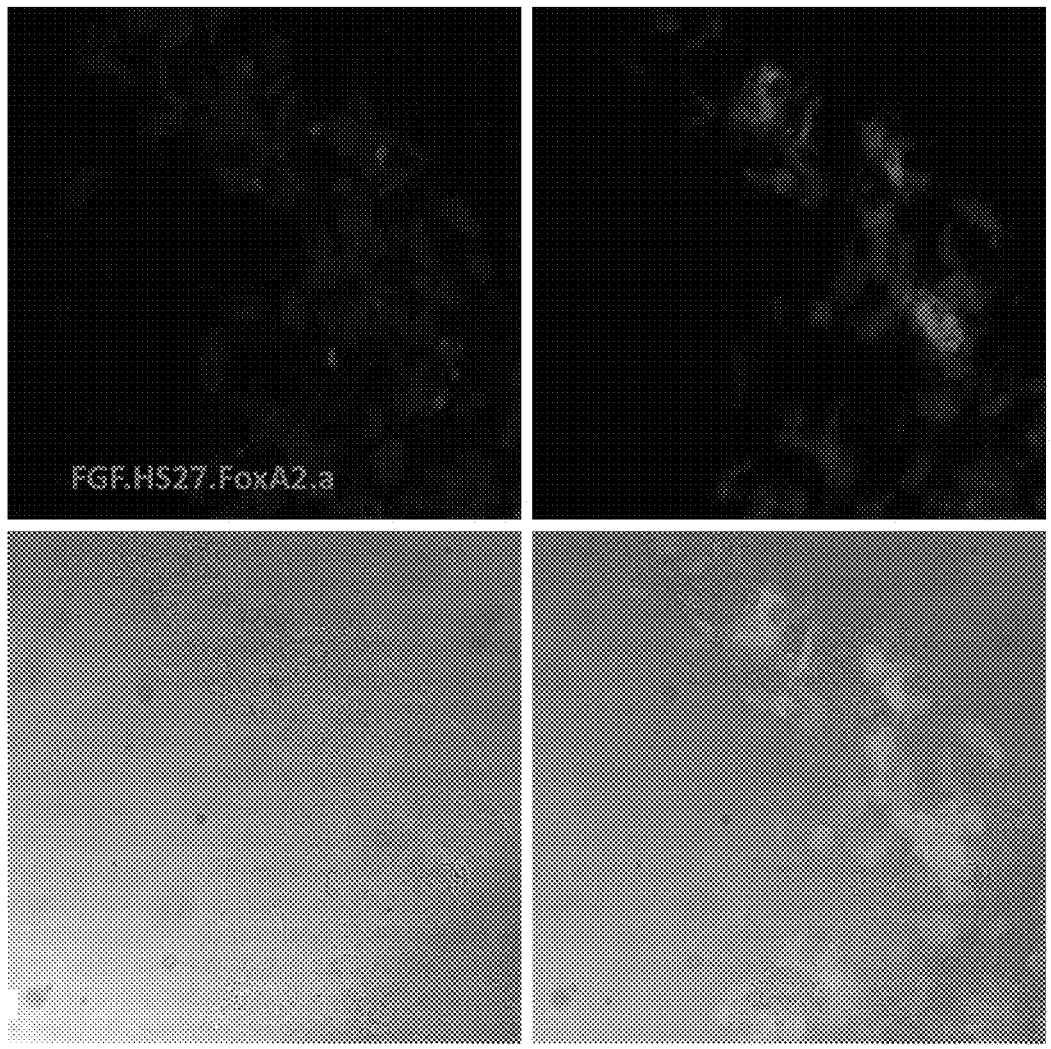

FIG. 31 is an image from a confocal microscope of H9 stem cells that have been grown in bFGF over human feeder cells and shows they are positive for Foxa2 a marker for primed stem cells.

Figure 32:
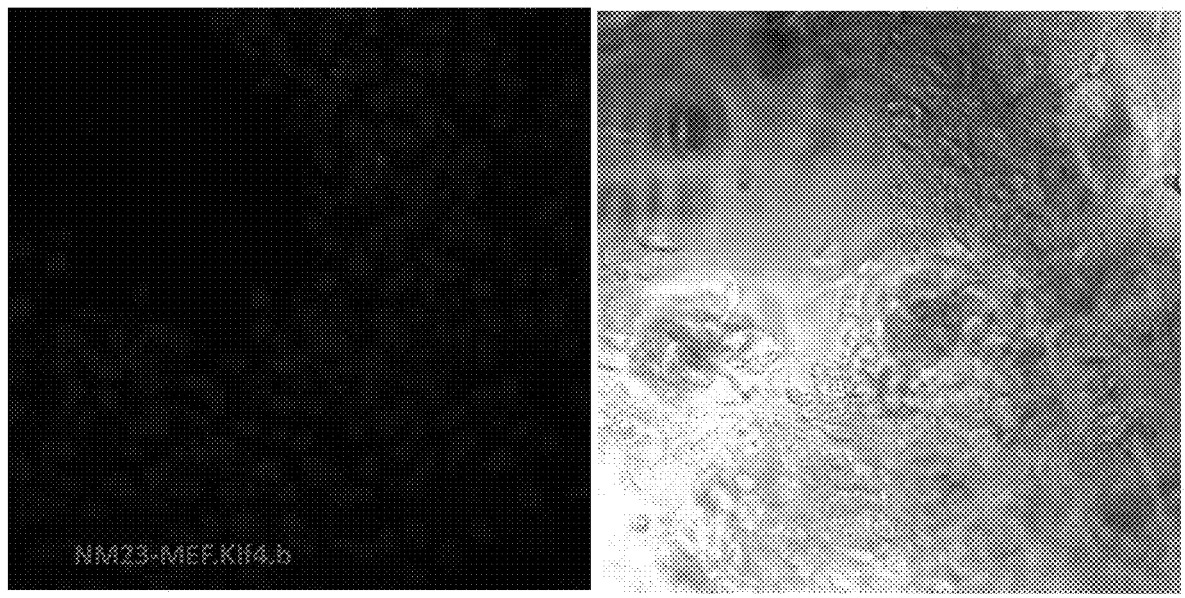

FIG. 32 is an image from a confocal microscope of H9 stem cells that have been grown in NM23-S120G over mouse feeder cells and shows they are negative for Klf4 which is a marker for naïve stem cells.

Figure 33:
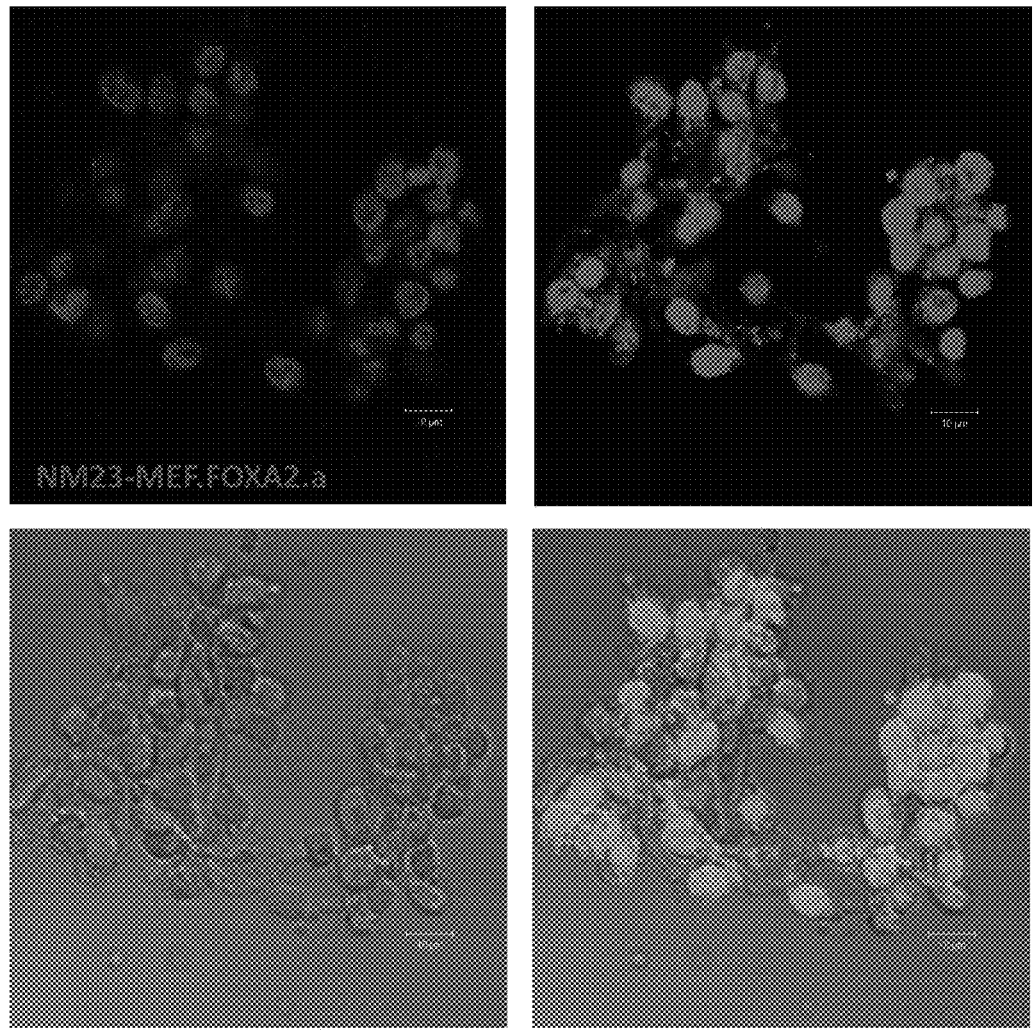

FIG. 33 is an image from a confocal microscope of H9 stem cells that have been grown in NM23-S120G over mouse feeder cells and shows they are positive for Foxa2 a marker for primed stem cells.

Figure 34:
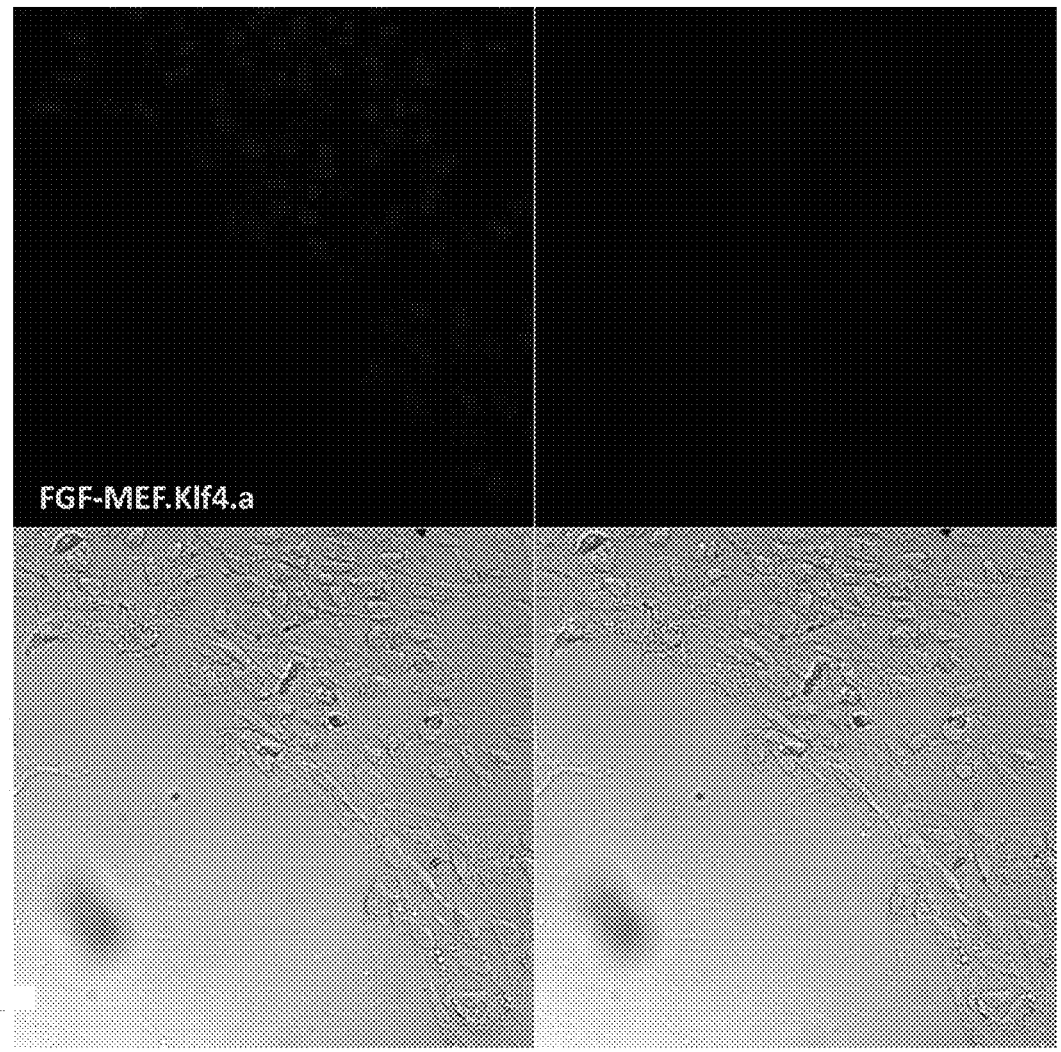

FIG. 34 is an image from a confocal microscope of H9 stem cells that have been grown in bFGF over mouse feeder cells and shows they are negative for Klf4 which is a marker for naïve stem cells.

Figure 35:
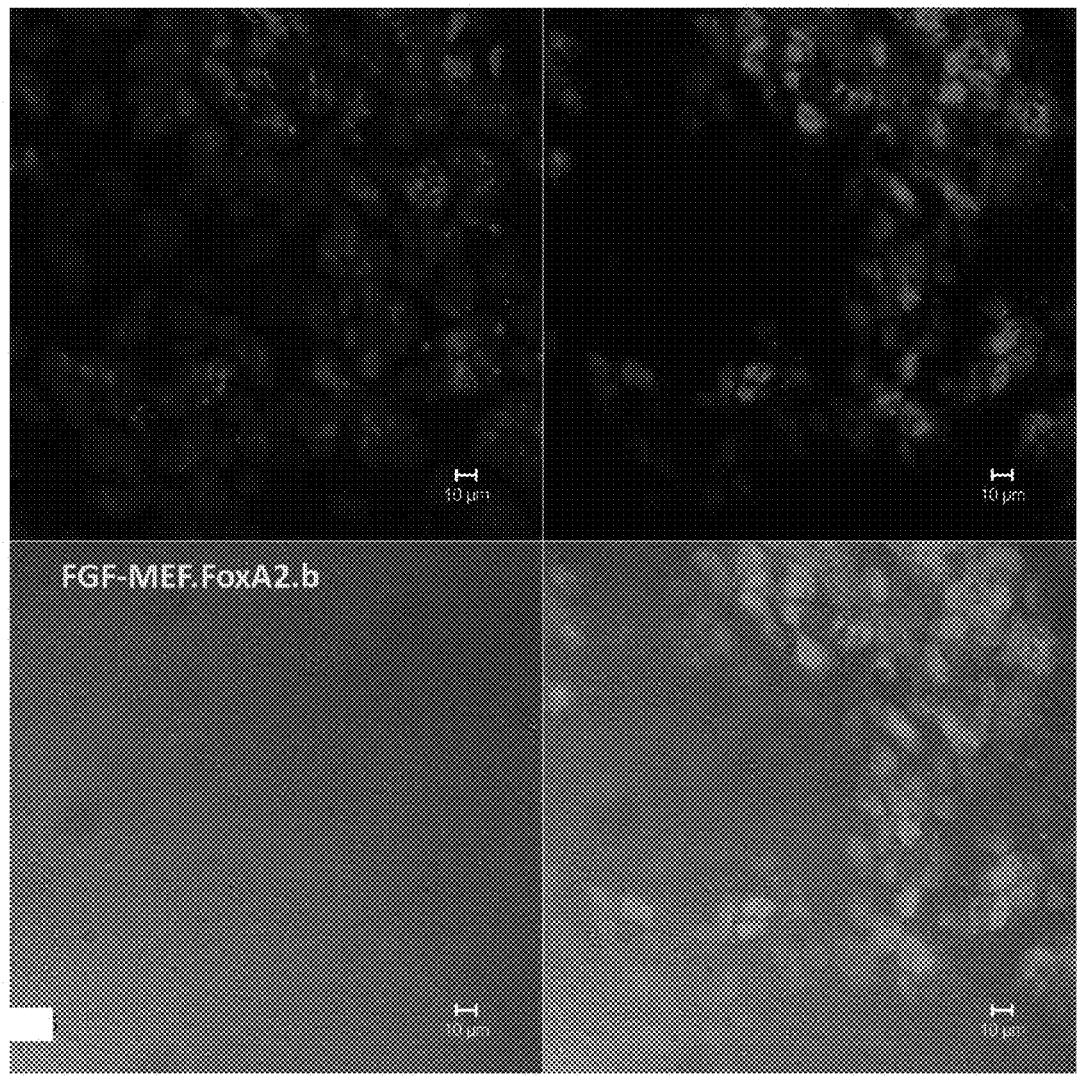

FIG. 35 is an image from a confocal microscope of H9 stem cells that have been grown in bFGF over mouse feeder cells and shows they are positive for Foxa2 a marker for primed stem cells.

Figure 36:
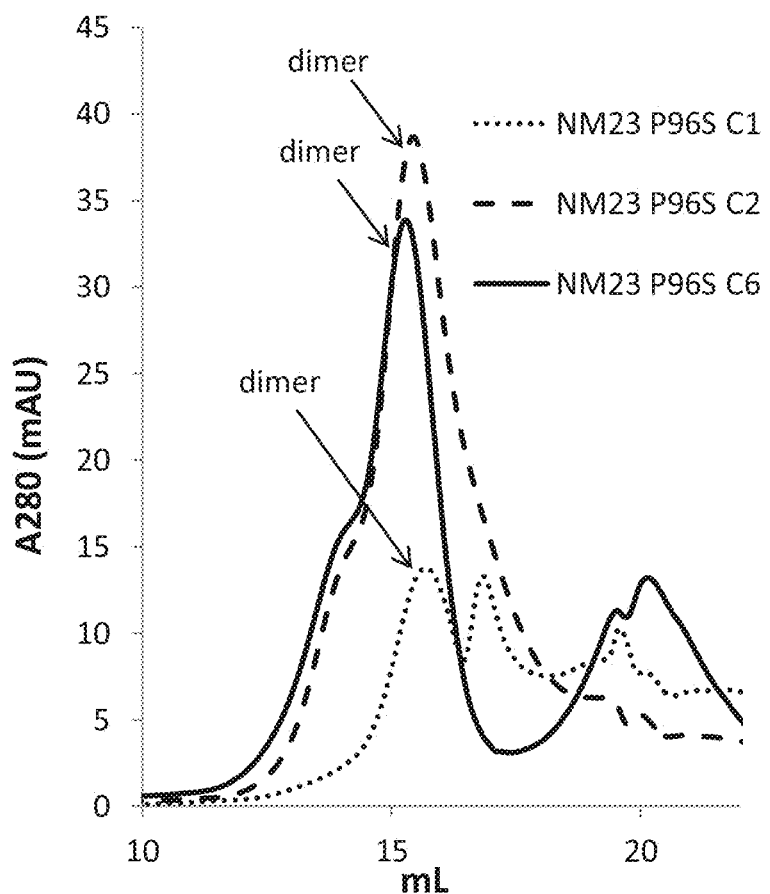

FIG. 36 is an overlay of FPLC traces of the soluble fractions of NM23-P96S mutants having 1, 2 or 6 deletions at the C-terminus, wherein the dimer peaks are indicated.

Figure 37:
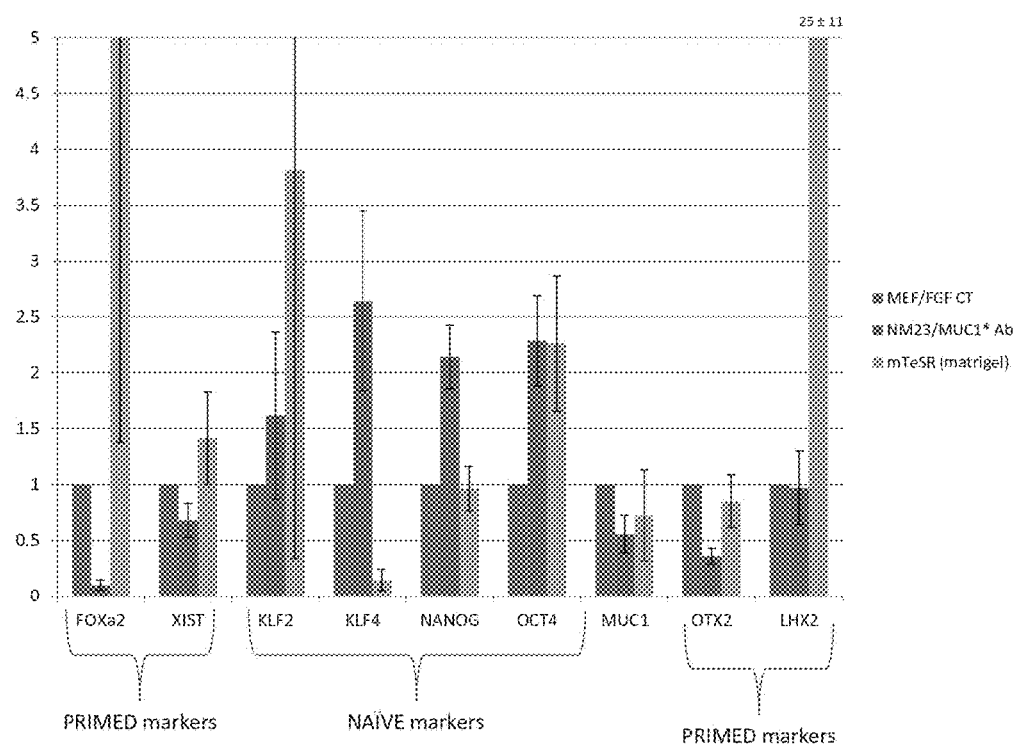

FIG. 37 shows graph of RT-PCR experiments to measure the expression levels of naïve and primed markers for human ES cells grown under a variety of conditions which are described in Example 10.

DETAILED DESCRIPTION OF THE PREFERRED EMBODIMENTS

In the present application, "a" and "an" are used to refer to both single and a plurality of objects.

The present invention relates to the field of mammalian cell culture, and particularly to the culture of immature cells such as stem cells, and provides methods and compositions for cell attachment to, cultivation on and detachment from a substrate containing from at least about 0.5% N, a sum of O and N greater than or equal to 17.2% and a contact angle of about 13.9 degrees and lacking a feeder layer. In one embodiment, the substrate also has attached thereto an antibody that binds to a cell surface receptor. In another embodiment, the cells are cultured in a media that contains a MUC1* activator. In yet another embodiment, the media also contains a Rho Kinase or a Rho inhibitor (ROCi). In yet another embodiment, the invention relates to methods for eliminating the need for a Rho kinse inhibitor. In still another embodiment, the invention relates to methods, growth factors and surfaces for the selection of, maintenance of or induction of naïve state stem cells.

Stem Cell Proliferative Surface

As used herein, a stem cell proliferation surface is any surface that may be chemically or biologically modified to enable the attachment of human stem cells, which further allows the stem cells to proliferate and from which the stem cells can be harvested. WO2009/105570 describes plasma modification of plasticware for cell culture such that the resultant surface is better for cell attachment and in particular enables the attachment of human stem cells, which are non-adherent cells. One of the surfaces described in WO2009/105570 is marketed as Vita™ surface (Thermo-Fisher, USA). In particular, surface #4 in WO '570 has been promoted for the growth of stem cells. Unfortunately, the methods required to prepare, also known as "acclimate", these cells to be able to bind to and then grow on those surfaces is very long and involved. WO '570 discloses that stem cells that are manually dissected and lifted off of another surface do not bind to their surfaces. In addition, the stem cells need to be enzymatically passaged to single cells several times, e. g., 38 times and 48 times before they will bind or grow on the disclosed surfaces. Instructions for use of the Vita™ surfaces further describe that stem cells must be cultured in the presence of a Rho kinase inhibitor, without which the stem cells will not bind to or stay bound to the surface. Another shortcoming of WO '570 is that although the disclosed surfaces are defined substrates intended to replace the use of Matrigel and feeders cells, stem cells do not grow on the surfaces unless conditioned media from mouse feeder cells is added to the standard bFGF stem cell culture media, thus defeating the purpose of a defined, animal-free surface.

In the present invention, we have shown that surfaces described in WO2009/105570, more particularly surfaces that are comprised of 1.7-2.1% Nitrogen, 26.4-28.7% Oxygen and 28.2-30.7% Nitrogen and Oxygen combined, wherein the surface has a contact angle of 14.3-18.8 degrees, can be used for the culture of stem cells in the absence of conditioned media if they are grown in the presence of a ligand that dimerizes the MUC1* receptor. Ligands that dimerize and activate the MUC1* receptor include bivalent antibodies raised against the PSMGFR peptide whose sequence corresponds to the first 45 amino acids of the MUC1 receptor that are proximal to the cell surface. Preferred are antibodies raised against peptides whose sequence corresponds to the PSMGFR peptide except lacking the 10 amino acids that are immediately adjacent to the cell surface. NM23 is a ligand of MUC1* and more particularly dimeric NM23 or mutants such as NM23-S120G, NM23-P96S which may or may not be combined with C-terminal deletions of 1-6 amino acids that prefer dimer formation over formation of teteramers and hexamers are especially preferred.

In addition to eliminating the need for conditioned media, the present invention discloses a method for minimizing the acclimation time required to adapt stem cells to growth on these and other defined surfaces. As is more fully detailed elsewhere in the present application, stem cells that have been grown in NM23 do not need a lengthy adaptation period. Further, stem cells previously cultured in FGF and conditioned media can be adapted to bind to the surfaces described in application WO2009/105570 by briefly incubating the cells in NM23 containing media before introduction to the defined surface. The contents of WO2009/105570 are incorporated by reference herein in its entirety, in particular regarding its disclosure of the material and composition of the stem cell growth surface.

In another improvement, the present invention is directed to coating the surfaces described in WO2009/105570 with ligands or antibodies that bind to the MUC1* receptor, which results in improved cell attachment, and inhibits spontaneous differentiation better than using the surfaces absent the MUC1* ligands. See FIG. 12e. The invention also contemplates the use of ligands to other stem cell surface proteins.

Naïve Cells

Recent research articles conclude that human stem cells cultured in FGF and fibroblast feeder cell conditioned media are no longer truly pluripotent (naïve or ground state) stem cells. Rather, growth in bFGF has brought the human stem cells to a more mature state called "primed." The results of work in the area of primed versus naïve human stem cells imply that primed stem cells are not able to differentiate into fully functional adult cells the way true pluripotent stem cells should. Researchers have developed methods to temporarily revert primed stem cells back to the true pluripotent state which they call "naïve". Because naïve stem cells grow via a different pathway than primed stem cells, it follows that they will bear cell surface receptors that are either different from or expressed to different levels than those expressed on the surface of primed stem cells. Therefore, primed stem cells and naïve stem cells will differ in their affinities for chemically or biochemically defined surfaces.

One of the characteristics of primed stem cells is that they cannot survive serial harvesting using enzymatic cleavage, but naïve stem cells can. Because WO2009/105570 discloses that only stem cells that are serially harvested by enzymatic cleavage will bind to their surfaces, we conclude that naïve stem cells bind to the WO '570 surfaces, in particular the surface marketed as Nunclon™ Vita™ surface (ThermoFisher, USA). Therefore, surfaces described in WO2009/105570, herein are referred to as Vita surfaces or Vita-like surfaces, can be used to select for naïve stem cells and more generally for the growth and/or maintenance of human stem cells that are in the naïve state or in a more naïve state than those cultured in the conventional bFGF media on feeder cell surfaces.

Figure 12A:
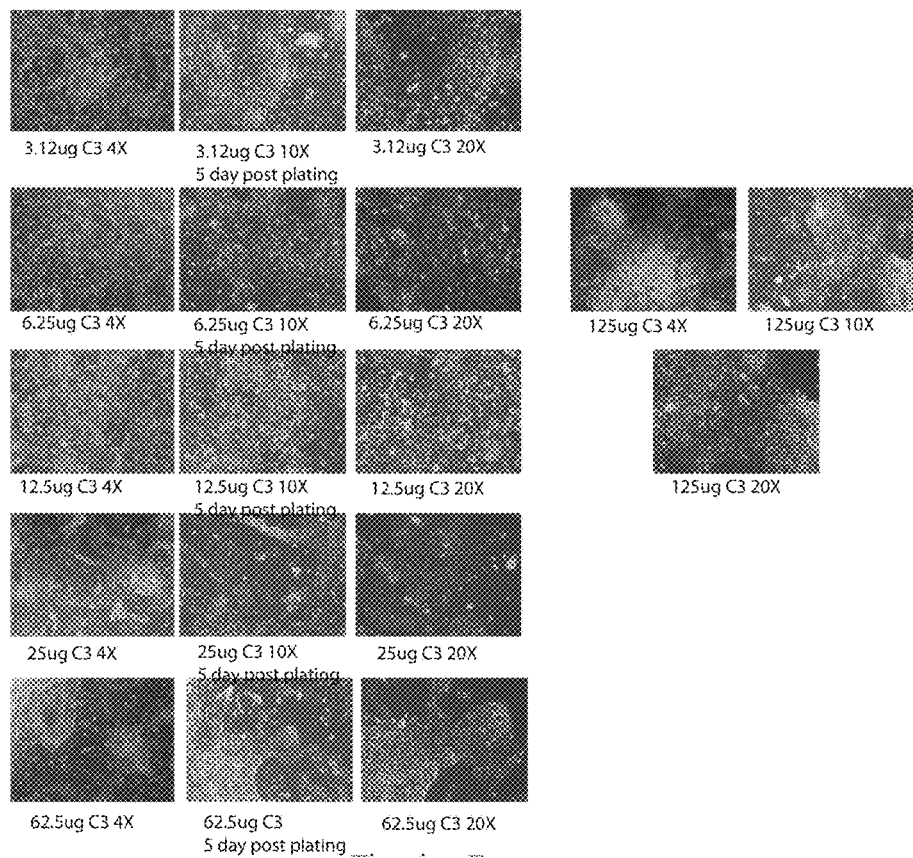
FIG. 12a-d shows photos from 4× magnification to 20× of human ES cells that have been trypsinized to single cells then plated onto Vita-type surfaces that were coated with varying amounts of monoclonal antibody 2D6C3 as indicated and cultured in NM23-MM wherein a Rho kinase inhibitor was present during the first 48 hours to aid in attachment.
Figure 12B:
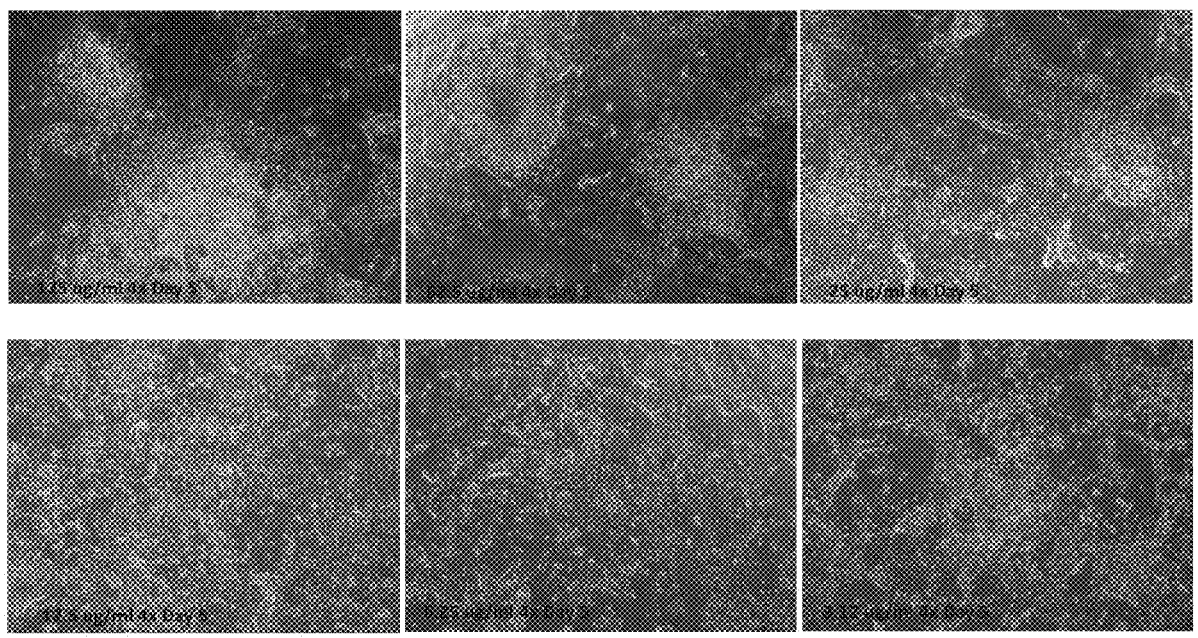
Figure 25:
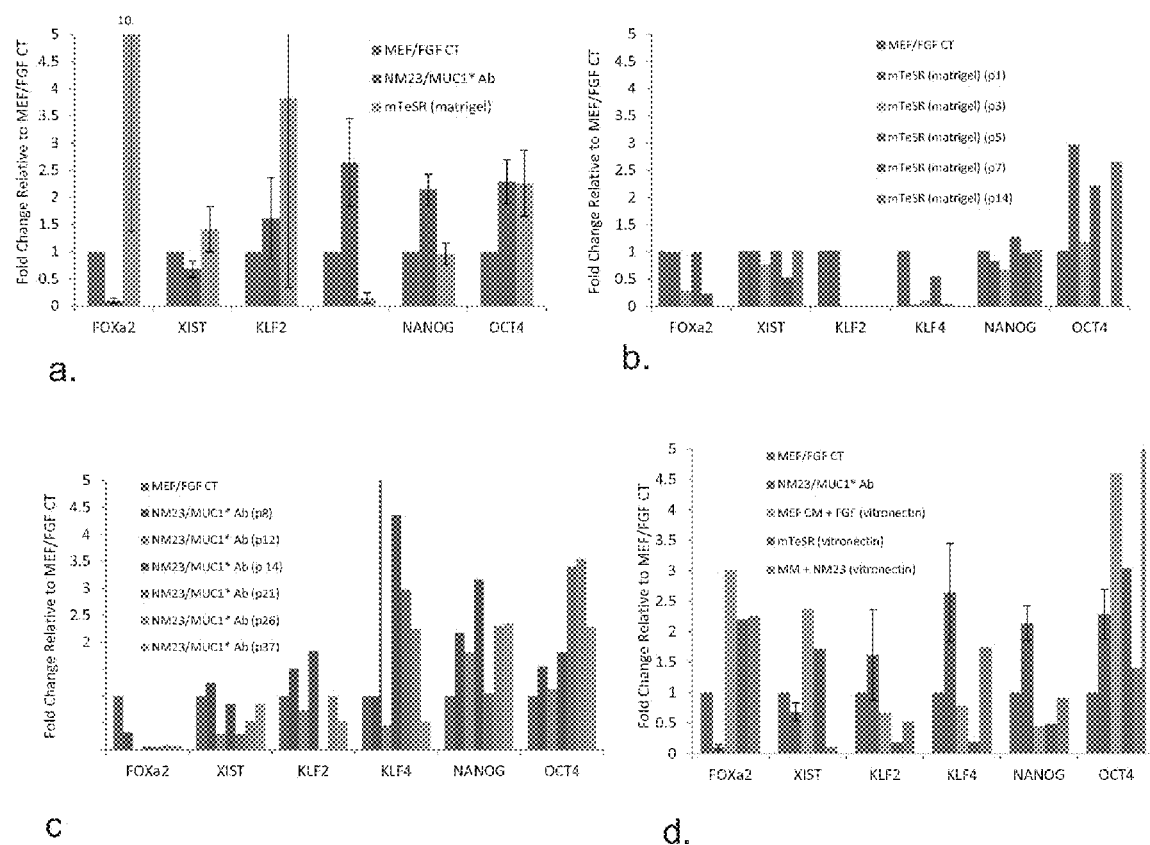

Another reported characteristic of naïve stem cells is that they have the ability to grow in sheets and not just in colony formation. We have observed that stem cells cultured with a MUC1* activator, including anti-MUC1* antibodies and NM23, also grow in sheets when grown on non-feeder cell surfaces and non-Matrigel surfaces. More particularly, human stem cells cultured with a bivalent MUC1* activator, including anti-MUC1* antibodies and dimeric NM23 or NM23 variants, and growing over a surface that has been coated with anti-MUC1* or NM23 dimers, grow in sheets rather than colonies which is characteristic of naïve human stem cells. In a preferred embodiment, anti-MUC1* antibodies are adsorbed onto a Vita or Vita-like surface and attached human stem cells are cultured in a minimal stem cell media containing NM23 or an NM23 variant wherein it is in the dimeric state. FIG. 12e showing results of Example 5 demonstrates that human stem cells grow in sheets rather than colonies when cultured in a media containing a MUC1* activator and on a Vita-like surface, optionally presenting anti-MUC1* antibodies. In an especially preferred embodiment, the MUC1* activator media does not contain bFGF or TGF-beta. FIG. 25 and the experiment of Example 10 show that human stem cells cultured in bFGF-containing media are in the primed state, whereas stem cells cultured in a MUC1* activating ligand, such as dimeric NM23, and optionally on a Vita or Vita-like surface also optionally presenting MUC1* ligands such as anti-MUC1* antibodies, are in the naïve state or in a more naïve state. In FIG. 12, RT-PCR is used to measure expression levels of naïve versus primed genes in human H9 ES (embryonic stem) cells. These cells cultured according to the standard method of 4 ng/ml bFGF added to minimal stem cell media and growing over a surface of mouse fibroblast feeder cells (MEFs), "MEF/FGF CT", have been defined as "1" and all other growth methods have been normalized to this value. In these figures "NM23/MUC1* Ab" refers to 8 nM of NM23-S120G in dimeric form in minimal stem cell media in the absence of any other growth factor, and cultured over a Vita plate coated with a MUC1* antibody (C3). FIG. 12 shows that compared to stem cells cultured by conventional methods, growth in NM23 dimers over a surface of a MUC1* antibody on a Vita plate resulted in lower expression of the primed markers and higher expression of the naïve markers.

mTeSR is a commercially available semi-defined media containing high concentrations of bFGF and TGF-beta. FIG. 12b shows the same type of stem cells cultured in mTeSR and over a layer of Matrigel, resulted in higher expression of the primed markers Foxa2 and XIST, but lower expression of the naïve markers Klf2, Klf4, and Nanog. Oct4, a pluripotency marker was on average expressed higher than the control. As can be seen from the passage number (p1-14), consecutive passaging in mTeSR over Matrigel did not improve the expression pattern of the "bad" markers.

Figure 12C:
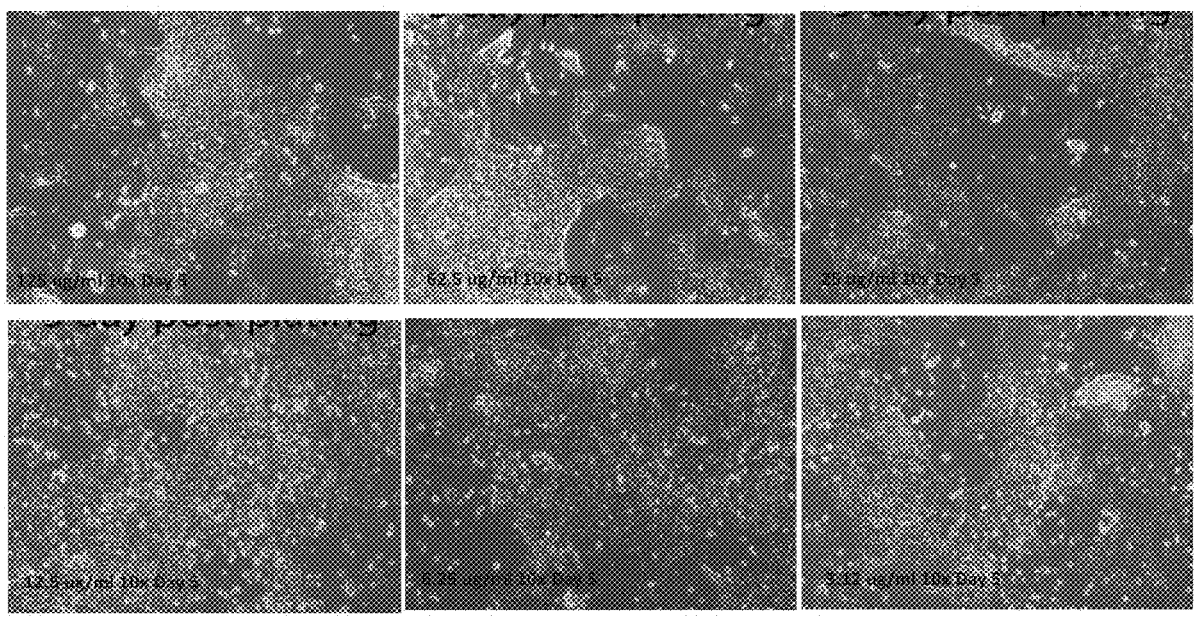

Conversely, FIG. 12c shows that culturing the stem cells in NM23 media over an anti-MUC1* antibody surface increased the expression of the naïve (good) markers and decreased the expression of the primed markers and that the pattern of naïve versus primed expression did improve with each successive passage number. Although the human integrin Vitronectin is defined and xeno-free when made as the recombinant protein, the results shown in FIG. 12d strongly argues that the interaction of Vitronectin with some antigen on the surface of stem cells signals a pathway that is not naïve. Stem cells of the same parent source were taken from growth on feeders in bFGF and for a single passage were cultured in either bFGF plus feeder cell conditioned media, mTeSR or NM23 in minimal media and all were grown over a layer of Vitronectin. The RT-PCR measurements show that although the NM23 media gave the gene expression profile that was more naïve than the others, in general, growth over Vitronectin caused an increase in expression of the primed markers and a decrease of the naïve markers.

FIG. 37 shows RT-PCR measurements of human stem cells cultured in bFGF over MEF feeders (n=3), mTeSR over Matrigel (n=5) or NM23-S120G dimers in minimal stem cell media over a Vita surface coated with 12.5 ug/ml of 2D6C3 the monoclonal anti-MUC1* antibody (n=6). In this experiment, two additional primed markers, OTX2 and LHX2, were also measured. The graph of FIG. 37 shows that consistent with other experiments, growth in NM23 over a surface presenting ligands for MUC1* increases expression of naïve markers and decreases expression of primed markers.

In a companion experiment, ICC staining was used to assess the expression of only two markers: FOXa2 (primed) and KLF4 (naïve) in response to growing human ES cells in either bFGF or NM23 (dimers in minimal stem cell media) over either mouse feeder cells or human feeder cells. FIGS. 27-35 show that only human stem cells cultured in an NM23 media over a surface of human fibroblasts expressed the naïve marker KLF4, but not the primed marker FOXa2. Conversely, the same source cells plated over a layer of mouse fibroblasts and cultured in media containing NM23 or bFGF did not express the naïve marker KLF4 but did express the primed marker FOXa2.

Taken together, these data indicate growing human stem cells over a layer of mouse cells or over a layer of Vitronectin maintains or induces the primed state and culturing human stem cells in bFGF-containing media also maintains or induces the primed state. We therefore conclude that human naïve stem cells grow by the MUC1* pathway and can be maintained or induced in media that activates this pathway. For example, in a media that contains an agent that dimerizes MUC1* and in solution or on a surface that does not activate a primed pathway and optionally activates a pluripotency pathway such as ligands that dimerize MUC1*. In a preferred embodiment, stem cells are maintained or induced to revert to a more naïve state by culturing them in a media that contains the dimeric form of NM23 and cells are attached to a Vita-like surface or a surface that is coated with an anti-MUC1* antibody. In a still more preferred embodiment, the stem cells are cultured in an NM23 dimer containing media wherein the concentration of NM23 is between 8-32 nM and the surface is a Vita surface coated with anti-MUC1* antibody 2D6C3 or 2D6C8 at a concentration of 3-125 ug/mL. In addition, antibodies that bind to MUC1*, optionally plated onto a Vita-like surface, can be used to identify and isolate naïve stem cells.

In addition, primed stem cells can be made to revert to a naïve or more naïve state by growing them under conditions in which the MUC1* pathway is activated. For example, by the introduction of nucleic acids that cause or increase expression of MUC1* or its ligands, including NM23 or NM23 variants, or agents that result in increased cleavage of MUC1 are introduced into cells, which may be adult, progenitors or primed stem cells, to make them revert to a more naïve or naïve state.

Applicant has discovered that stem cells grow better on a surface in a minimal stem cell media (MM or MN6) that contains a MUC1* activator such as bivalent anti-MUC1* or NM23, particularly dimeric NM23 or mutant that prefer dimerization such as NM23-S120G, NM23-P96S, C-terminal deletions of NM23 wherein one to six amino acid deletions may be made or NM23-S120G or NM23-P96S also with one to six amino acid deletions at the N-terminus, wherein NM23-P96S with six deletions from the C-terminus is preferred because it produces a majority of dimers in the soluble fraction. In addition, when a thin layer of anti-MUC1* antibody is applied to a surface such as plasticware, tissue culture treated plate, Vita-like surfaces or the Vita™ surface, stem cell proliferation was enhanced and spontaneous differentiation was inhibited. Further, stem cells cultured in FGF and mouse embryonic fibroblast (MEF) conditioned media (CM) showed poor attachment to the Vita surface if plated in FGF-CM. In contrast, the cells attached and grew if they were plated in and subsequently cultured in NM23-MM media rather than FGF-CM. Attachment and subsequent growth was improved when FGF-CM (conditioned media)-grown cells were harvested then briefly incubated in NM23-MM, before plating.

The performance of defined surfaces such as those described in WO2009/105570, more particularly surfaces that are comprised of 1.7-2.1% Nitrogen, 26.4-28.7% Oxygen and 28.2-30.7% Nitrogen and Oxygen combined, wherein the surface has a contact angle of 14.3-18.8 degrees, was greatly improved by adding a layer of an agent that dimerizes MUC1* receptor, including anti-MUC1* antibodies and NM23, especially mutant NM23-S120G that prefers dimer formation. The present invention is directed to attaching an agent that dimerizes MUC1* to onto the surfaces described in WO '570. In a preferred embodiment, the agent is a bivalent anti-MUC1* antibody. Especially preferred are monoclonal antibodies 2D6C3 and 2D6C8. The invention also includes coating or attaching the antibodies to a layer of protein or polymer that is in contact with a surface described in WO '570.

The present invention is also directed to generation of polymers on a surface that result in their chemical composition being the percentages of N, O and N plus O essentially the same as the planar solid substrates described in WO2009/105570, more particularly surfaces that are comprised of 1.7-2.1% Nitrogen, 26.4-28.7% Oxygen and 28.2-30.7% Nitrogen and Oxygen combined, wherein the surface has a contact angle of 14.3-18.8 degrees. Agents that dimerize MUC1* may optionally be attached to these substrates to improve growth and inhibition of differentiation of human stem cells as well as for the isolation and enhancement of populations of naïve stem cells.

A kit of the invention may consist of a vessel for cell culture in which the chemical composition of the surface is approximately comprised of 1.7-2.1% Nitrogen, 26.4-28.7% Oxygen and 28.2-30.7% Nitrogen and Oxygen combined, wherein the surface has a contact angle of 14.3-18.8 degrees and instructions to culture cells in a media containing an agent that dimerizes MUC1*, such as bi-valent anti-MUC1* or NM23 or dimer form of NM23, NM23-S120G, NM23-P96S, or those mutations and those that have one to six C-terminal amino acid deletions.

We have discovered that human naïve stem cells grow via the MUC1* pathway and not by the FGF (fibroblast growth factor receptor) pathway.

Further we discovered that primed stem cells, ES and iPS (induced pluripotent stem), can be stably converted to the naïve state by activating the MUC1* growth factor receptor pathway.

We further discovered that human stem cells progress to the primed state or cannot be reverted to the naïve state even with activation of the MUC1* pathway if they are cultured in the presence of secretions from mouse cells, such as mouse embryonic fibroblast (MEF) feeder cells. On the contrary, human stem cells cultured in minimal media plus NM23 (optionally NM23-S120G mutant) over human feeder cells such as HS27 foreskin fibroblast feeder cells, do grow as more naïve stem cells and can be maintained in that state indefinitely and through serial passaging.

In addition to activating the MUC1* growth factor receptor, it is necessary not to activate certain pathways that make mouse stem cells grow. FGF should not be added to media for culturing human stem cells in the naïve state. Similarly, human stem cells will progress to the primed state if cultured over mouse feeder cells.

In contrast, human naïve stem cells will be stably maintained and propagated in the naïve state or at least a more naïve state if they are cultured with a MUC1* activator such as NM23-S120G and grown over human (and not mouse) feeder cells, such as HS27 foreskin fibroblast cells, or over a xeno-free surface. Xeno-free surfaces that do not secrete factors that would influence the cells to mature to the primed state include standard plasticware, cell culture treated plates, substrates with a high binding capacity such as Vita or Synthemax, all of which can optionally be derivatized with an antibody to a stem cell surface antigen such as anti-MUC1*, anti-Tra 1-81/1-60 or anti-SSEA3/4.

The MUC1* growth factor receptor pathway is activated by NM23 and in particular NM23 dimers. We typically activated naïve stem cell growth by culturing cells in a minimal stem cell media plus NM23-S120G mutant which is a mutant that prefers dimerization and does not form the higher order multimers that do not activate the MUC1* receptor. Other MUC1* activators include bivalent antibodies that bind to portions of MUC1* that dimerize it. For example, an antibody raised against the 45 amino acids of the MUC1* extra cellular domain dimerize and activate the MUC1* growth factor receptor and support stem cell growth.

The discoveries disclosed herein have far-reaching implications. First, most human stem cells today are grown in FGF over mouse feeder layers or over Matrigel and fed with FGF plus conditioned media from the mouse feeder cells. The findings presented herein show that both FGF and mouse feeder cells corrupt human stem cells and induce their progression into the primed state which may be a non-productive state from which they are not able to mature into functional adult cells. Therefore, in order to obtain adult functional cells from human stem cells, the starting cells must be in the naïve state. A major problem in the stem cell field is that many cells cannot be made to mature into functional adult cells and when they are coerced into doing so, it is a rare event. These studies are evidence that a major problem is that human stem cells that are in use today have been corrupted by exposure to pathways that are not human. Therefore, to obtain stem cells that are able to mature into functional adult cells, they must be cultured in a MUC1* activator, e. g. NM23 in dimeric form and if feeder cells are used at any time, they must be human.

Implications of Previous Characterization of Human Stem Cells that were all "Primed"

The discoveries disclosed herein show that many of the current "discoveries" based on work with corrupted stem cells are also corrupted. Data obtained from studies of stem cells grown by FGF pathway and/or on mouse feeder cells or their conditioned media is a mixture of pertinent and irrelevant data with no way of determining which findings apply to humans and which do not. For example, an emerging approach to the treatment of cancer is to suppress the cancer cell's ability to self-renew by inducing differentiation. Studies were done in which microRNAs of cancer cells were compared to the microRNAs of stem cells, especially newly differentiating stem cells, to determine which regulatory factors were missing in the cancer cells. The theory was that the missing microRNAs that induce differentiation could be introduced to the cancer cells to "reprogram" them so that they would behave more like healthy cells. The problem with this previous body of work is that the micro RNAs that were analyzed were from stem cells grown with FGF and over mouse feeder cells. Mounting evidence supports the theory that bFGF is the growth factor that makes mouse stem cells grow, but not human pluripotent stem cells. We now know that both bFGF and mouse feeder cells secrete factors that make human stem cells leave their natural naïve state and become "primed" or "mouse-human chimeras." The primed state is characterized by gene expression patterns, and consequently microRNA expression patterns, that are very different from those expressed in naïve stem cells. Therefore, many if not the vast majority of the microRNAs that were identified as signaling the onset of differentiation, and therefore useful in potential cancer treatments, may only signal the onset of mouse stem cell differentiation or may not be related at all to the natural state in which human naïve stem cells propagate via the MUC1* pathway and can only differentiate normally from the naïve state. Therefore, microRNAs previously identified as being those that signal human stem cell's exit from pluripotency may only be microRNAs that signal departure from an unnatural state of pseudo pluripotency and therefore would be of no use for the treatment of human cancers. Therefore, to accurately identify microRNA profiles that induce differentiation, which could be used to treat cancers, one would need to use naïve stem cells, which is the natural pluripotent state for human stem cells, cultured in growth factors that stimulate the human and not the mouse stem cell pathway. An accurate way to identify microRNAs that regulate differentiation of human stem cells or progenitors is to perform the differential analyses on human naïve stem cells that are allowed to differentiate from the naïve state. MicroRNAs that are upregulated when the naïve stem cells initiate differentiation are then identified and can be used for the treatment of cancers. In a preferred embodiment, the naïve cells are obtained by culturing human stem cells in NM23, dimeric form, on surfaces coated with anti-MUC1* antibodies. In a more preferred embodiment the surfaces coated with anti-MUC1* antibodies are Vita-like surfaces. In other embodiments, naïve-like stem cells may be cultured in NM23 dimers over a layer of inactivated human feeder cells or over a layer of human cancer cells or in the presence of their secretions. microRNAs present in newly differentiating naïve stem cells but missing from the cancer cells are identified and used as anti-cancer therapeutic agents.

In a previous patent application WO 2011/159960, the inventors put forward evidence that cancer cells are cells that have become trapped in a stem cell proliferation plateau. We noted that some kinds of cancer cells can be co-cultured while others cannot. We stated that the cancer cells that can be co-cultured are trapped in the same stem cell proliferation plateau and their growth is being regulated by the same signature of microRNAs. Cancer cells that can be co-cultured belong to the same type of cancer which is independent of organ of origin. The identity of the individual microRNAs in each signature that regulates each cancer type can be determined using techniques such as Deep Sequencing and total transcriptome analysis. Once the microRNA signatures of the different sub-types of cancer have been identified, cancers can be treated or prevented by mixing together one or more microRNA signatures of a different cancer type than the one that has affected the patient. In an alternative approach, the microRNA signature that maintains human naïve stem cells in various proliferation plateaus could be determined, then these different microRNA signatures could be mixed to create a cancer vaccine.

MUC1

MUC1 comprises several regions termed herein as follows, recited in an order starting from the C-terminus and extending through the cell membrane and out into the extracellular domain. The basic structure of the MUC1 receptor comprises: 1) cytoplasmic tail; 2) transmembrane section; 3) MGFR; 4) IBR, 5) Unique Region, 6) repeats, and N-terminus region comprising a signal peptide. For a detailed description of MUC1 and its function in normal and tumor cells, see PCT/US2005/032821, which is incorporated by reference herein, in its entirety for its description of the function and activity of cleaved MUC1 on the cell surface.

The term "MUC1 Growth Factor Receptor" (MGFR) is a functional definition meaning that portion of the MUC1 receptor that interacts with an activating ligand, such as a growth factor or a modifying enzyme such as a cleavage enzyme, to promote cell proliferation. The MGFR region of MUC1 is that extracellular portion that is closest to the cell surface and is defined by most or all of the PSMGFR, as defined below. The exact cleavage site of MUC1 is not known and further, enzymes that cleave the protein can cleave at one or more locations. It also appears that the MUC1* growth factor receptor form, which is a cleavage product, may be cleaved at varying locations based on the cell type. The MGFR is inclusive of both unmodified peptides and peptides that have undergone enzyme modifications, such as, for example, phosphorylation, glycosylation, etC. Results of the invention are consistent with a mechanism in which this portion is made accessible to the ligand upon MUC1 cleavage at a site associated with tumorigenesis that causes release of the some or all of the IBR from the cell. MGFR is also known as MUC1*.

As used herein, "anti-PSMGFR" refers to any antibody that recognizes a region of the MGFR and optionally any portion of PSMGFR. Antibody to nat-PSMGFR is exemplified and preferred in the application, but is not meant to be limited to an antibody made against this specific sequence, as other fragments of MGFR and PSMGFR are also contemplated.

An anti-MUC1* antibody refers to any antibody that recognizes a MUC1 protein, present on stem cells, progenitor cells or cancer cells, wherein the MUC1 protein is devoid of the tandem repeat domain. The term "Primary Sequence of the MUC1 Growth Factor Receptor" (PSMGFR) is a peptide sequence that defines most or all of the MGFR in some cases, and functional variants and fragments of the peptide sequence, as defined below. The PSMGFR is defined as SEQ ID NO:10 listed below in Table 1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus A "functional variant or fragment" in the above context refers to such variant or fragment having the ability to specifically bind to, or otherwise specifically interact with, ligands that specifically bind to, or otherwise specifically interact with, the peptide of SEQ ID NO:10. One example of a PSMGFR that is a functional variant of the PSMGFR peptide of SEQ NO: 10 (referred to as nat-PSMGFR—for "native") is SEQ NO: 12 (referred to as var-PSMGFR), which differs from nat-PSMGFR by including an —SPY- sequence instead of the native —SRY- (see bold text in sequence listings). Var-PSMGFR may have enhanced conformational stability, when compared to the native form, which may be important for certain applications such as for antibody production. The PSMGFR is inclusive of both unmodified peptides and peptides that have undergone enzyme modifications, such as, for example, phosphorylation, glycosylation, etC.

TABLE 1

Peptide sequences (listed from N-terminus to C-terminus):

Full-length MUC1 Receptor (Mucin 1 precursor, Genbank Accession number: P15941)
MTPGTQSPFF LLLLLTVLTV VTGSGHASST PGGEKETSAT

QRSSVPSSTE KNAVSMTSSV LSSHSPGSGS STTQGQDVTL

APATEPASGS AATWGQDVTS VPVTRPALGS TTPPAHDVTS

APDNKPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

TABLE 1-continued

Peptide sequences (listed from N-terminus to C-terminus):

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDNRPALGS TAPPVHNVTS

ASGSASGSAS TLVHNGTSAR ATTTPASKST PFSIPSHHSD

TPTTLASHST KTDASSTHHS SVPPLTSSNH STSPQLSTGV

SFFFLSFHIS NLQFNSSLED PSTDYYQELQ RDISEMFLQI

YKQGGFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL (SEQ ID NO: 1)

N-terminal MUC-1 signaling sequence for directing MUC1 receptor and truncated isoforms to cell membrane surface. Up to 3 amino acid residues may be absent at C-terminal end as indicated by variants in SEQ ID NOS:2, 3 and 4.

(SEQ ID NO: 2)
MTPGTQSPFFLLLLLTVLT.

(SEQ ID NO: 3)
MTPGTQSPFFLLLLLTVLT VVTA (SEQ ID NO: 4)
MTPGTQSPFFLLLLLTVLT VVTG

A truncated MUC1 receptor isoform having nat-PSMGFR at its N-terminus and including the transmembrane and cytoplasmic sequences of a full-length MUC1 receptor ("nat-PSMGFRTC isoform"—An example of "PSMG-FRTC"—shown excluding optional N-terminus signal sequence, which may be cleaved after translation and prior to expression of the receptor on the cell surface):

(SEQ ID NO: 5)
```
G TINVHDVETQ FNQYKTEAAS RYNLTISDVS

VSDVPFPFSA QSGAGVPGWG IALLVLVCVL VALAIVYLIA

LAVCQCRRKN YGQLDIFPAR DTYHPMSEYP TYHTHGRYVP

PSSTDRSPYE KVSAGNGGSS LSYTNPAVAA ASANL
```

A truncated MUC1 receptor isoform having nat-PSMGFR and PSIBR at its N-terminus and including the transmembrane and cytoplasmic sequences of a full-length MUC1 receptor ("CM isoform"—shown excluding optional N-terminus signal sequence, which may be cleaved after translation and prior to expression of the receptor on the cell surface):

(SEQ ID NO: 6)
```
GFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL
```

A truncated MUC1 receptor isoform having nat-PSMGFR+PSIBR+Unique Region at its N-terminus and including the transmembrane and cytoplasmic sequences of a full-length MUC1 receptor ("UR isoform"—shown excluding optional N-terminus signal sequences):

(SEQ ID NO: 7)
```
ATTTPASKST PFSIPSHHSD TPTTLASHST KTDASSTHHS

TVPPLTSSNH STSPQLSTGV SFFFLSFHIS NLQFNSSLED

PSTDYYQELQ RDISEMFLQI YKQGGFLGLS NIKFRPGSVV

VQLTLAFREG TINVHDVETQ FNQYKTEAAS RYNLTISDVS

VSDVPFPFSA QSGAGVPGWG IALLVLVCVL VALAIVYLIA

LAVCQCRRKN YGQLDIFPAR DTYHPMSEYP TYHTHGRYVP

PSSTDRSPYE KVSAGNGGSS LSYTNPAVAA ASANL
```

A truncated MUC1 receptor isoform including the transmembrane and cytoplasmic sequences of a full-length MUC1 receptor ("Y isoform"—shown excluding optional N-terminus signal sequence, which may be cleaved after translation and prior to expression of the receptor on the cell surface):

(SEQ ID NO: 8)
```
GSGHASSTPG GEKETSATQR SSVPSSTEKN AFNSSLEDPS

TDYYQELQRD ISEMFLQIYK QGGFLGLSNI KFRPGSVVVQ

LTLAFREGTI NVHDMETQFN QYKTEAASRY NLTISDVSVS

DVPFPFSAQS GAGVPGWGIA LLVLVCVLVA LAIVYLIALA

VCQCRRKNYG QLDIFPARDT YHPMSEYPTY HTHGRYVPPS

STDRSPYEKV SAGNGGSSLS YTNPAVAATS ANL
```

A truncated MUC1 receptor isoform having nat-PSMGFR+PSIBR+Unique Region+Repeats at its N-terminus and including the transmembrane and cytoplasmic sequences of a full-length MUC1 receptor ("Rep isoform"— shown excluding optional N-terminus signal sequence, which may be cleaved after translation and prior to expression of the receptor on the cell surface):

(SEQ ID NO: 9)
```
LDPRVRTSAP DTRPAPGSTA PQAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DTRPAPGSTA

PPAHGVTSAP DTRPAPGSTA PPAHGVTSAP DNRPALGSTA

PPVHNVTSAS GSASGSASTL VHNGTSARAT TTPASKSTPF

SIPSHHSDTP TTLASHSTKT DASSTHHSSV PPLTSSNHST

SPQLSTGVSF FFLSFHISNL QFNSSLEDPS TDYYQELQRD

ISEMFLQIYK QGGFLGLSNI KFRPGSVVVQ LTLAFREGTI

NVHDVETQFN QYKTEAASRY NLTISDVSVS DVPFPFSAQS

GAGVPGWGIA LLVLVCVLVA LAIVYLIALA VCQCRRKNYG

QLDIFPARDT YHPMSEYPTY HTHGRYVPPS STDRSPYEKV

SAGNGGSSLS YTNPAVAAAS ANL
```

Native Primary Sequence of the MUC1 Growth Factor Receptor (nat-PSMGFR—an example of "PSMGFR"):

(SEQ ID NO: 10)
```
GTINVHDVETQFNQYKTEAASRYNLTISDVSVSDVPFPFSAQSGA
```

Native Primary Sequence of the MUC1 Growth Factor Receptor (nat-PSMGFR—An example of "PSMGFR"), having a single amino acid deletion at the N-terminus of SEQ ID NO:10):

(SEQ ID NO: 11)
```
TINVHDVETQFNQYKTEAASRYNLTISDVSVSDVPFPFSAQSGA
```

"SPY" functional variant of the native Primary Sequence of the MUC1 Growth Factor Receptor having enhanced stability (var-PSMGFR—An example of "PSMGFR"):

(SEQ ID NO: 12)
```
GTINVHDVETQFNQYKTEAASPYNLTISDVSVSDVPFPFSAQSGA
```

"SPY" functional variant of the native Primary Sequence of the MUC1 Growth Factor Receptor having enhanced stability (var-PSMGFR—An example of "PSMGFR"), having a single amino acid deletion at the C-terminus of SEQ ID NO:12):

Truncated PSMGFR receptor (TR) (having "SPY" sequence of var-PSMGFR):

```
                                        (SEQ ID NO: 13)
TINVHDVETQFNQYKTEAASPYNLTISDVSVSDVPFPFSAQSGA
```

Extended Sequence of MUC1 Growth Factor Receptor (ESMGFR) (having "SPY" sequence of var-PSMGFR):

```
                                        (SEQ ID NO: 14)
GTINVHDVETQFNQYKTEAASPYNLTISDVSVS
```

Tumor-Specific Extended Sequence of MUC1 Growth Factor Receptor (TSESMGFR) (having "SPY" sequence of var-PSMGFR):

```
                                        (SEQ ID NO: 15)
VQLTLAFREGTINVHDVETQFNQYKTEAASPYNLTISDVSVSDVPFPF
```

Primary Sequence of the Interchain Binding Region) (PSIBR):

```
                                        (SEQ ID NO: 16)
SVVVQLTLAFREGTINVHDVETQFNQYKTEAASPYNLTISDVSVSDVPFP

FSAQSGA
```

Truncated Interchain Binding Region) (TPSIBR):

```
                                        (SEQ ID NO: 17)
GFLGLSNIKFRPGSVVVQLTLAFRE
```

Repeat Motif 2 (RM2):

```
                                        (SEQ ID NO: 18)
SVVVQLTLAFREG
```

```
(SEQ ID NO: 19)
PDTRPAPGSTAPPAHGVTSAPDTRPAPGSTAPPAHGVTSA
```

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1.1

Stem Cell Minimal Media "MM"

Minimal Medium ("MM") 500 mL includes the following: 400 ml DME/F12/GlutaMAX I (Invitrogen #10565-018), 100 ml Knockout Serum Replacement (Invitrogen#10828-028), 5 ml 100×MEM Non-essential Amino Acid Solution (Invitrogen#11140-050), 0.9 ml (0.1 mM) beta-mercaptoethanol (55 mM stock, Invitrogen#21985-023), and optionally may contain 2.5 ml PSA (penicillin, streptomycin, amphotericin) MP Biochem (#1674049) for minimizing contamination risk.

Example 1.2

Stem Cell Defined Media—"MN6"

The 6-component minimal media, "MN6" consists of DMEM/F12/GlutaMAX or similar base media suitable for cell culture, supplemented with 1% non-essential amino acids, 64 mg/L ascorbic acid (Sigma), 14 ug/L sodium selenium (Sigma), 19.4 mg/L insulin (Sigma), 543 mg/L sodium bicarbonate (Sigma) and 10.7 mg/L transferrin (Sigma).

Example 1.3

Polyclonal Anti-MUC1* Antibodies that Facilitate Stem Cell Attachment to Surfaces Coated with the Antibody Rabbit polyclonal antibodies were generated by immunizing animals with the Primary Sequence of the MUC1 Growth Factor Receptor (PSMGFR) peptide. Sera was collected according to standard methods and then purified over an affinity column to which was bound either the PSMGFR peptide or a PSMGFR peptide missing the last ten (10) C-terminal amino acids, "C-10 peptide". The purified antibodies (SDIX-anti-FLR and SDIX-anti-C-10, respectively) were then coated directly onto plastic cell culture plates (Vita plates, ThermoFisher; or BD Falcon #353046) and shown to facilitate stem cell attachment. To coat surfaces with the antibody, concentrations between 1 ug/mL and 300 ug/mL in a volume of PBS that allowed for complete surface coverage was incubated at 4 degrees C. overnight or at room temperature for approximately 3 hours. Human stem cells bound to these anti-PSMGFR surfaces and the amount of attachment corresponded to the concentration of antibody coated onto the surface; a control antibody did not cause any stem cell attachment, see FIGS. 24a-c. Human stem cells H9s (WiCell) and BGO1V/hOG cells (Life Technologies) attached and proliferated as undifferentiated stem cells when cultured in minimal stem cell media, "MM", alone, in the presence of low nanomolar concentrations of NM23-H1 in the dimeric form, or in MM plus 4 ng/mL of bFGF supplemented with 50% conditioned media from either human or mouse fibroblast feeder cells. We concluded that the bivalent anti-PSMGFR antibody attached to the plate surface caused dimerization of the MUC1* receptor and thus acted as the growth factor. However, cells proliferated faster when NM23 (dimers) were added into the media.

Example 2

Development of Monoclonal Antibodies, 2D6C8 and 2D6C3 (Also Referred to Here as C3 and C8) that Facilitate Human Stem Cell Attachment to Surfaces MUC1* monoclonal antibodies were identified that preferentially bound to the portion of the MUC1* extra cellular domain that is more distal from the cell surface and these monoclonals were shown to better facilitate the attachment of human ES and iPS cells to surfaces. Mice were immunized with a peptide that is defined by the PSMGFR sequence. Supernatants of hybridoma clones were tested by ELISA for their ability to bind to the PSMGFR peptide and by FACS to determine which bound to live, MUC1* positive cells. Hybridomas were further selected if they preferentially bound to the PSMGFR peptide lacking 10 C-terminal amino acids, but did not bind if the peptide lacked the 10 N-terminal peptides. In addition, hybridomas were screened for their ability to facilitate stem cell attachment to a surface such as a plastic cell culture plate. Of these clones two, 2D6C8 and 2D6C3 were selected that when coated onto a surface captured stem cells and facilitated their growth.

FIG. 13 shows amino acid sequence for the 2D6C3 Kappa Chain Variable Region. CDR1: RSSQTIVHSNGNTYLE (SEQ ID NO:20); CDR2: KVSNRFS (SEQ ID NO:21); and CDR3: FQGSHVPFT (SEQ ID NO:22).

FIG. 14 shows amino acid sequence for the 2D6C3 Heavy Chain Variable Region. CDR1: GYAMS (SEQ ID NO:23); CDR2: TISSGGTYIYYPDSVKG (SEQ ID NO:24); and CDR3: LGGDNYYEY (SEQ ID NO:25).

FIG. 15 shows amino acid sequence for the 2D6C8 Kappa Chain Variable Region. CDR1: RASKSVSTSGYSYMH (SEQ ID NO:26); CDR2: LVSNLES (SEQ ID NO:27); and CDR3: QHIRELTRSE (SEQ ID NO:28).

FIG. 16 shows amino acid sequence for the 2D6C8 Heavy Chain Variable Region. CDR1: GYAMS (SEQ ID NO:29); CDR2: TISSGGTYIYYPDSVKG (SEQ ID NO:30); and CDR3: LGGDNYYEY (SEQ ID NO:31).

FIG. 17 shows amino acid sequence for the 3C2B1 Kappa Chain Variable Region.
CDR1: RASKSISTSDYNYIH (SEQ ID NO:32); CDR2: LASNLES (SEQ ID NO:33); and CDR3: QHSRELPLTF (SEQ ID NO:34).

FIG. 18 shows amino acid sequence for the 3C2B1 Heavy Chain Variable Region. CDR1: TYTMS (SEQ ID NO:35); CDR2: TISTGGDKTYYSDSVKG (SEQ ID NO:36); and CDR3: GTTAMYYYAM (SEQ ID NO:37).

Example 2.1

Monoclonal Antibodies 2D6C8 or 2D6C3 Coated onto Plasticware Facilitate Attachment of Human ES and iPS Cells Monoclonal antibodies 2D6C8 or 2D6C3 were coated onto a variety of plastic cell culture plates and tested for their ability to capture human stem cells from a variety of sources. Approximately 1 mL of antibody at concentrations ranging from 3 ug/mL to 125 ug/mL was coated onto regular plasticware or tissue culture treated plasticware from a variety of vendors. It was observed that tissue culture treated plates were marginally better than untreated polystyrene for the purpose of attaching antibody and subsequently stem cells to the surface. As in the previous examples, it was observed that growth in minimal stem cell media, MM, alone gave rise to proliferating stem cells, but that proliferation was vastly improved if low nanomolar concentrations of NM23-H1 (dimers) or a bivalent anti-PSMGFR antibody were present in the media.

Example 3

Figure 2:
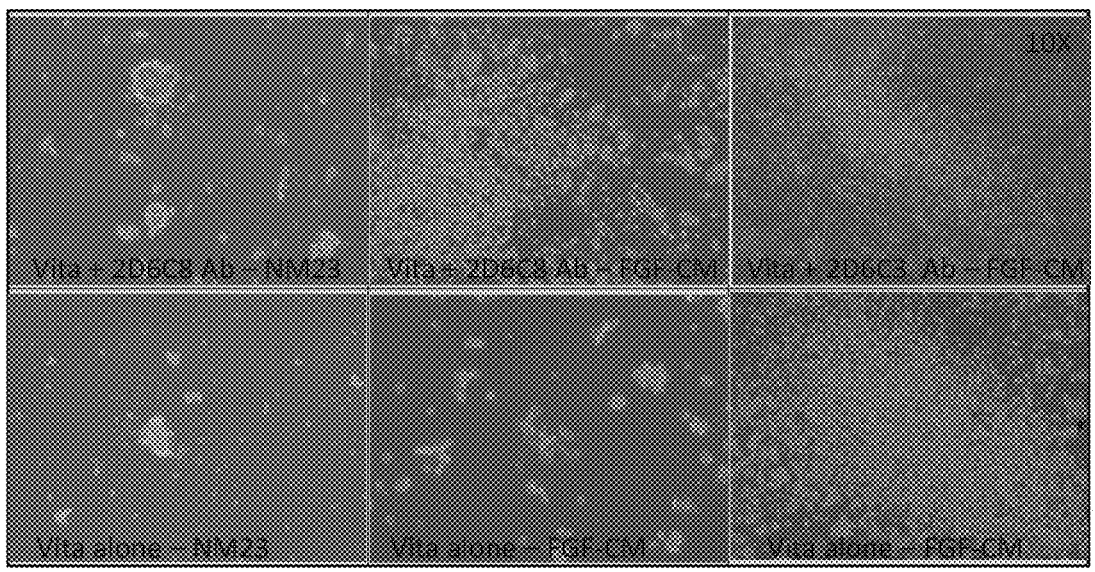
FIG. 2 shows photos of the experiments shown in FIG. 1 of human ES H9 cells plated onto various surfaces and cultured in either NM23 based media or bFGF-media. Images were taken on Day 2 prior to media change and show that only human stem cells plated over the Vita surface or Vita surface coated with an anti-MUC1* antibody and cultured in NM23-based media supported stem cell attachment.
Figure 3:
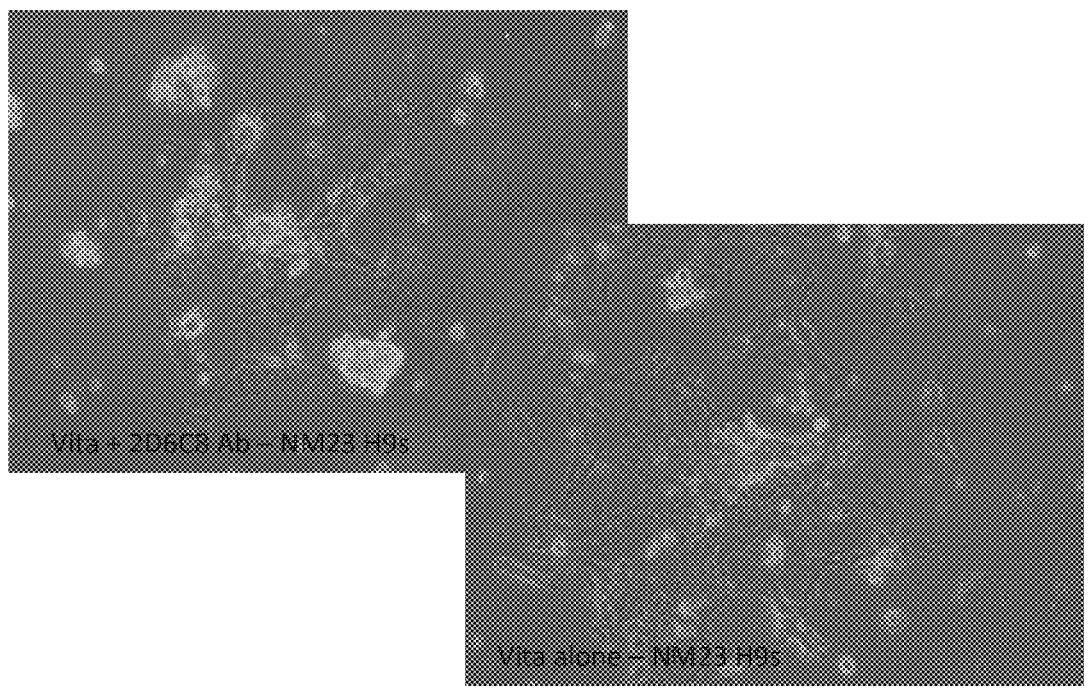
FIG. 3 shows 20× magnification of wells with Vita surface or Vita surface coated with an anti-MUC1* antibody and cultured in NM23-based media on Day 3, and showing pluripotent stem cell growth.
Figure 4:
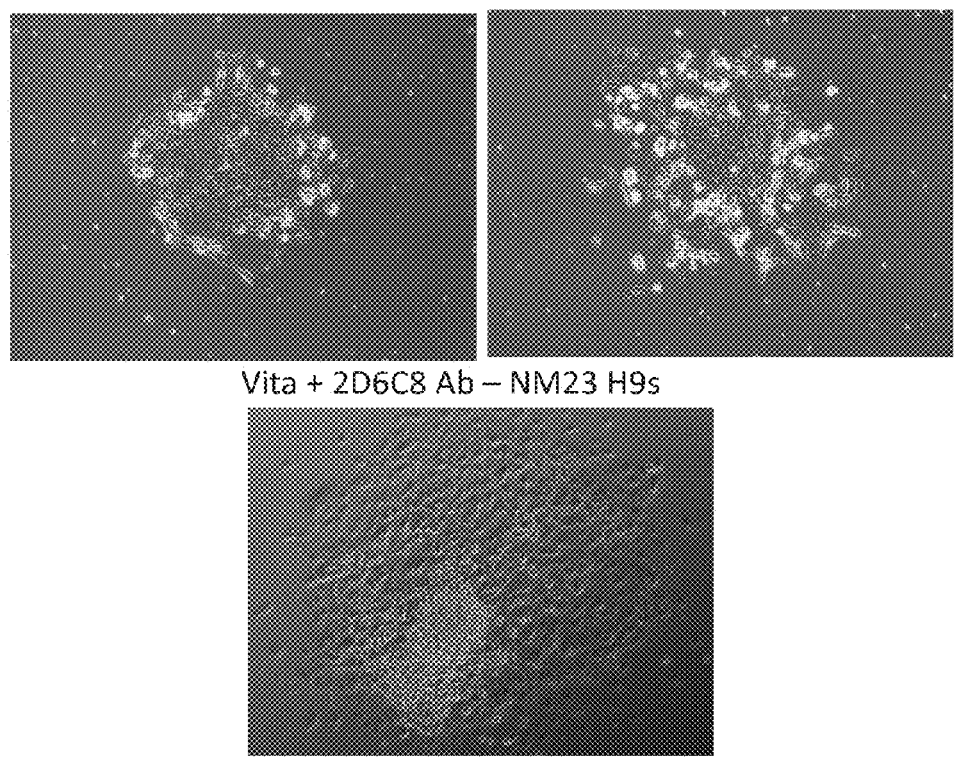
FIG. 4 shows photos of the only 3 colonies that survived as pluripotent stem cells by Day 5, which occurred in well that had a Vita surface coated with monoclonal anti-MUC1* antibody and cultured in NM23-Minimal Media (MM).
Figure 6:
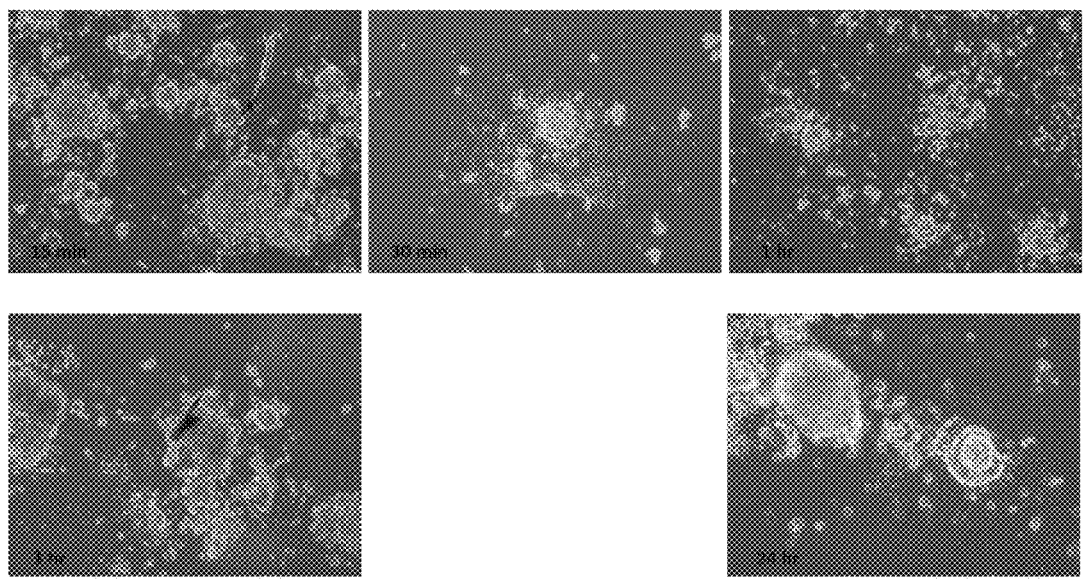
FIG. 6 is a photo showing that human stem cell colony pieces attach better to surfaces if the volume containing the cells is minimized Times noted in the figure refers to the amount of time that elapsed before NM23 was added to the minimal media (MM).
Figure 7:
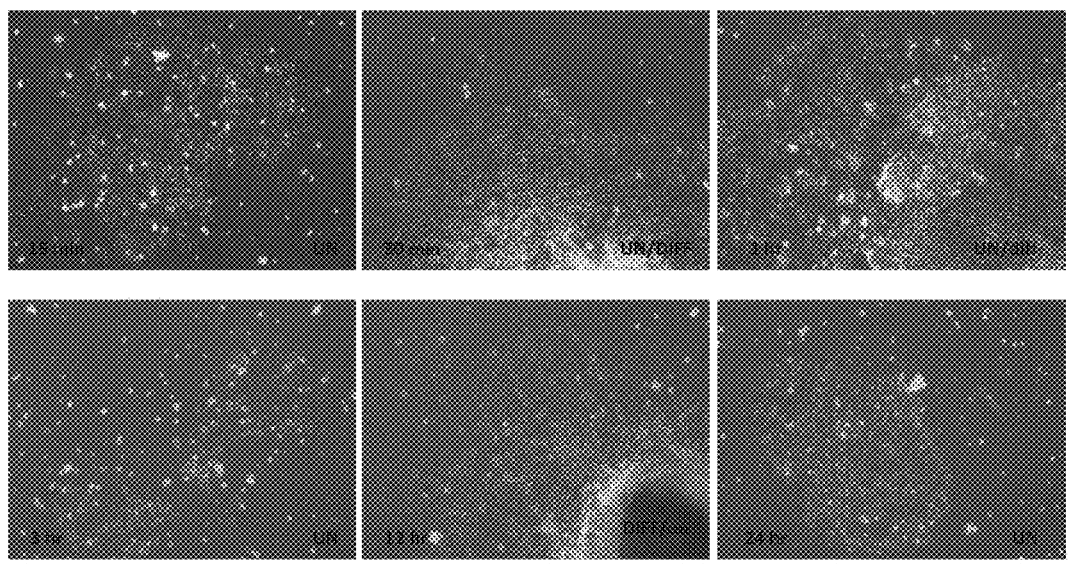
FIG. 7 shows Day 7 photos of the experiment described in FIG. 5 and documents enhanced cellular attachment due to reduced plating volume.

Vita Plates Coated with 2D6C8 or 2D6C3 Facilitate Attachment of Both ES and iPS Cell Growth Vita plates (ThermoFisher), bare or coated with 125 ug of either 2D6C8 or 2D6C3 monoclonal anti-MUC1* antibody, were tested for their ability to facilitate stem cell attachment and subsequent growth. Embryonic stem (ES) cells (H9s) that had been grown on MEF feeder cells and cultured in Minimal stem cell Media (MM) plus 8 nM NM23-S120G were manually harvested and colony pieces were plated onto either Vita alone or Vita coated with 2D6C8 mab or Vita+ 2D6C3 mab. A second source of stem cells was plated over identical surfaces. These were H9 ES cells grown on Matrigel and cultured in 4 ng/ml bFGF+50% conditioned media from mouse embryonic fibroblast (MEF) feeder cells. Undifferentiated colonies were manually dissected and harvested, then plated onto Vita alone or Vita plus an anti-MUC1* antibody. After plating, the stem cells were cultured in whichever media the cells had previously been grown in: 8 nM NM23 in dimeric form or 4 ng/mL bFGF plus 50% conditioned media from mouse feeder cells. Stem cells cultured in NM23-MM attached to both Vita alone and Vita+2D6C8 but, surprisingly, stem cells cultured in bFGF-MEF-CM showed poor attachment and the few cells that did attach differentiated after 1-2 days into fibroblast-like cells or died. The NM23-MM stem cells that bound to the Vita alone surface differentiated more quickly than those on the Vita+2D6C8 antibody surface. By Day 8 post-plating, undifferentiated colonies remained where the source cells had been cultured in NM23 and wherein the surface was a Vita plate coated with an anti-PSMGFR antibody (2D6C8). These colonies were harvested and passaged onto fresh Vita+2D6C8 surfaces, where they continued to grow without reduction in growth rate and as undifferentiated colonies for an additional 5 days. The experimental setup and results are shown in FIG. 1. FIG. 2 shows photographs of the wells as in the experimental setup of FIG. 1, but at Day 2, prior to media change. The cells in the wells cultured in bFGF and conditioned media have not attached and were lost with the first media change. The cells in wells in the left-most column that were cultured in NM23-MM both formed undifferentiated stem cell colonies (FIGS. 2, 3). However, only the surface coated with 2D6C8 antibody produced colonies that remained undifferentiated until Day 5 (FIG. 4), so could be serially passaged. In conclusion, the Vita surface alone did not support human stem cell growth as well as the Vita surface coated with an anti-PSMGFR antibody such as 2D6C8 or 2D6C3. Further, stem cells plated onto a Vita surface, with or without the antibody coating, did not facilitate stem cell growth if cultured in bFGF plus feeder cell conditioned media. The experimental setup of FIG. 5 and images of FIGS. 6 (Day 2) and 7 (Day 7) show that if the volume that the stem cells are in is reduced when cells are plated onto antibody coated surfaces, cell attachment and colony formation is more than tripled. Plating cells in 1 mL, rather than in 4 mL, resulted in up to 14 colonies formed compared to 3 colonies attaching from the larger volume. The times noted in FIGS. 6 and 7 correspond to time between plating cells in MM alone and the time when NM23 in the dimer form was added, which appears to be optimal between 0 minutes and 3 hours post plating.

Figure 9:
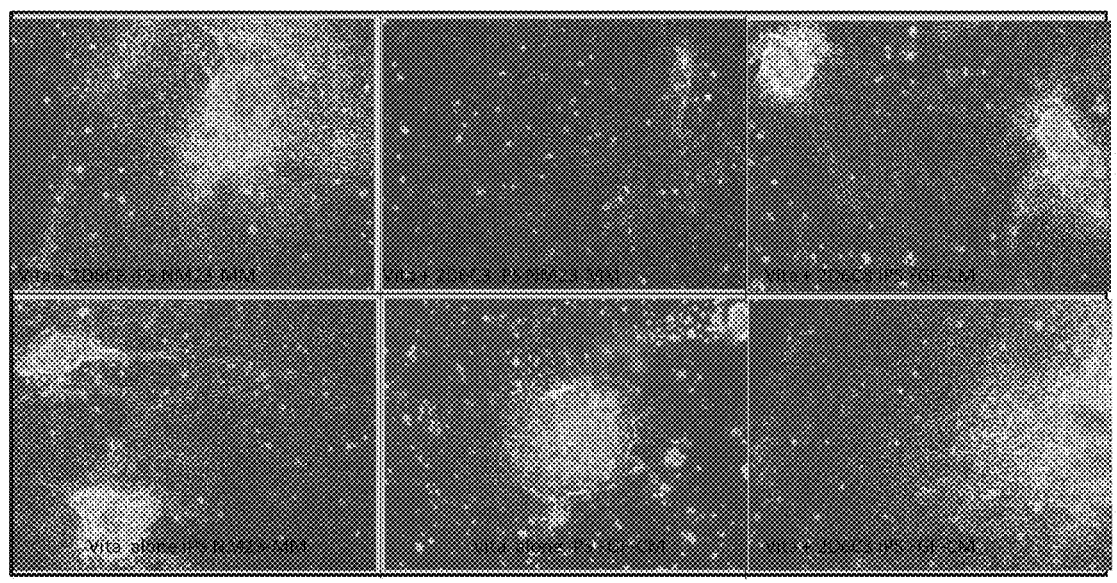
FIG. 9 shows Day 7 photos of human iPS colony pieces from source cells that had previously been grown in either NM23-MM or in bFGF plus MEF conditioned media. In addition, monoclonal antibodies 2D6C3 and 2D6C8 are compared to a Vita surface alone. These iPS cells were first pre-incubated with NM23-MM for 30 minutes prior to plating and were plated in 1 mL MM for 3 hours before volume was increased to 4 mLs in NM23-MM.

Induced pluripotent human stem cells (iPS) cells were assayed according to the experimental setup of FIG. 8 and results shown in FIG. 9. iPS cells from two sources were tested: a) previously cultured in 8 nM NM23-dimers over Matrigel; or b) previously cultured in 4 ng/mL bFGF over mouse fibroblast feeder cells. After plating the stem cell colony pieces in 1 mL of 8 nM NM23 (dimers) in minimal media (MM) and waiting 3 hours, the volume was increased to 4 mLs per well of a 6-well plate. Media was changed every 48 hours. Cells were allowed to grow until Day 7, when cells were becoming overgrown and beginning to differentiate, which allowed for assessing which conditions were best for overall attachment, proliferation and/ or inhibition of differentiation. In conclusion, both MUC1* antibodies make Vita surfaces better at inhibiting differentiation for longer periods of time. The Vita plus antibody surfaces had colonies that 100% undifferentiated at Day 5 and by Day 7 were showed the most cells and the least differentiation.

Example 4

Optimization of Protocol for Stem Cell Growth on Anti-PSMGFR Antibody Coated Surfaces and in NM23 (Dimer) Containing Media Several factors were identified that improved the efficiency of human ES and iPS cell attachment and proliferation: 1) trypsinized (or otherwise single) stem cells work better than colony pieces when using anti-PSMGFR antibody coated surfaces, especially if the base surface is a surface with atomic composition similar to the Vita surface; 2) cells that were previously cultured in low nanomolar concentrations of dimeric NM23 on other surfaces such as feeder cells or Matrigel, fared better than cells cultured in bFGF, however, this effect could be minimized by a 30 minute incubation in low nanomolar dimer NM23 just prior to plating; and 3) the use of a Rho kinase inhibitor for the first 24 hours after plating improved stem cell attachment, but did not affect stem cell survival. Further, it was noted that decreasing the volume of stem cell growth media from 4 mLs per well of a 6-well plate to 2 mLs or 1 mL enhanced stem cell attachment. Additionally, changing the cell growth media every 24 hours rather than every 48 hours, but using 2 mLs of media rather than 4 mLs was an improvement for the maintenance of some cell types.

Example 4.1

The Effect of Rho Kinase Inhibitor on Stem Cell Culture

In the previous experiments, there was significant loss of stem cells during passaging due to poor attachment or due to cells attaching in clumps. In this experiment we compared attachment, growth and differentiation for both iPS cells and ES H9 cells on either Vita surface plus Rho Kinase inhibitor (ROCi: Y-27632, Calbiochem) or Vita plus anti-MUC1* antibody without ROCi or a Vita surface plus anti-MUC1* antibody plus ROCi. To minimize the cell clumping, undifferentiated stem cell colony pieces were first trypsinized to yield single cells. (Trypsin used at 0.05%, which is 0.5 g/L or 21.45 µM, supplied as 50 ml of a 1× solution, Mediatech, InC. Cat. No: 25-052.)

Figure 11:
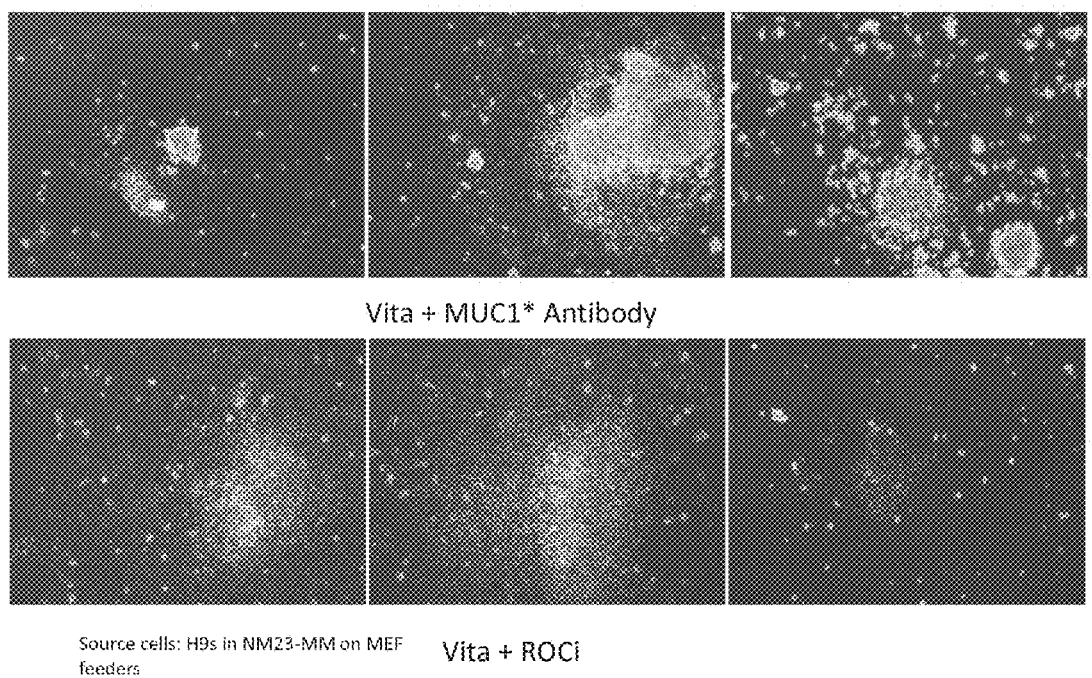
FIG. 11 shows photos of stem cells in an experiment that compared the Vita surfaces alone but with a Rho kinase inhibitor (ROCi) to Vita surface coated with an anti-MUC1* antibody but in the absence of a ROCi.
Figure 12D:
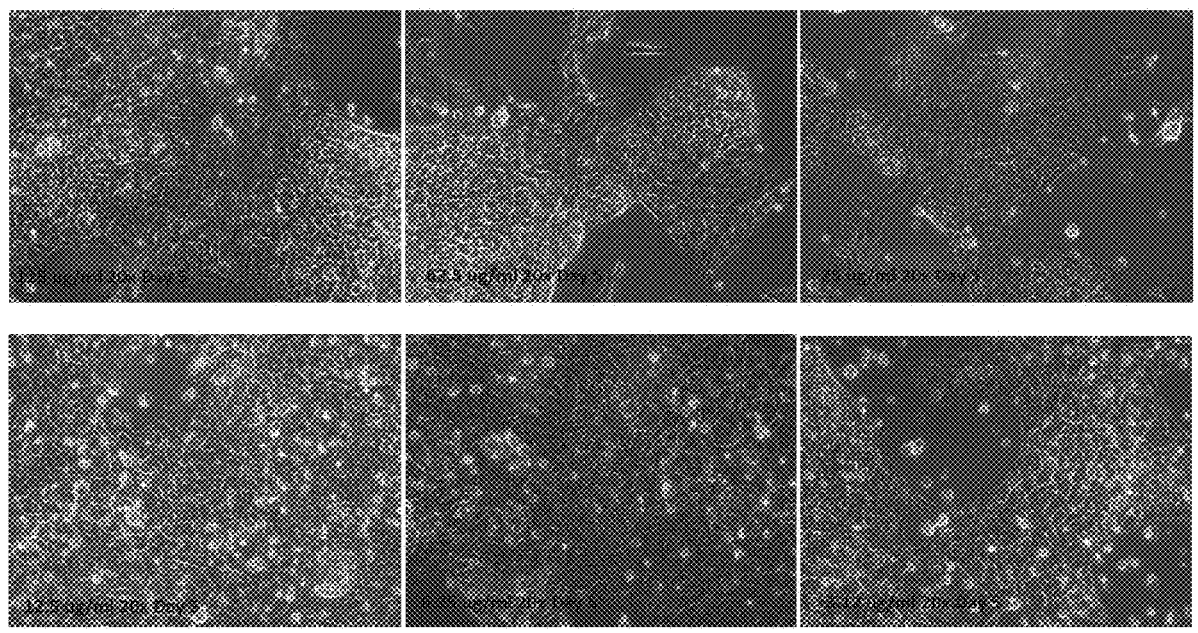
Figure 12E:
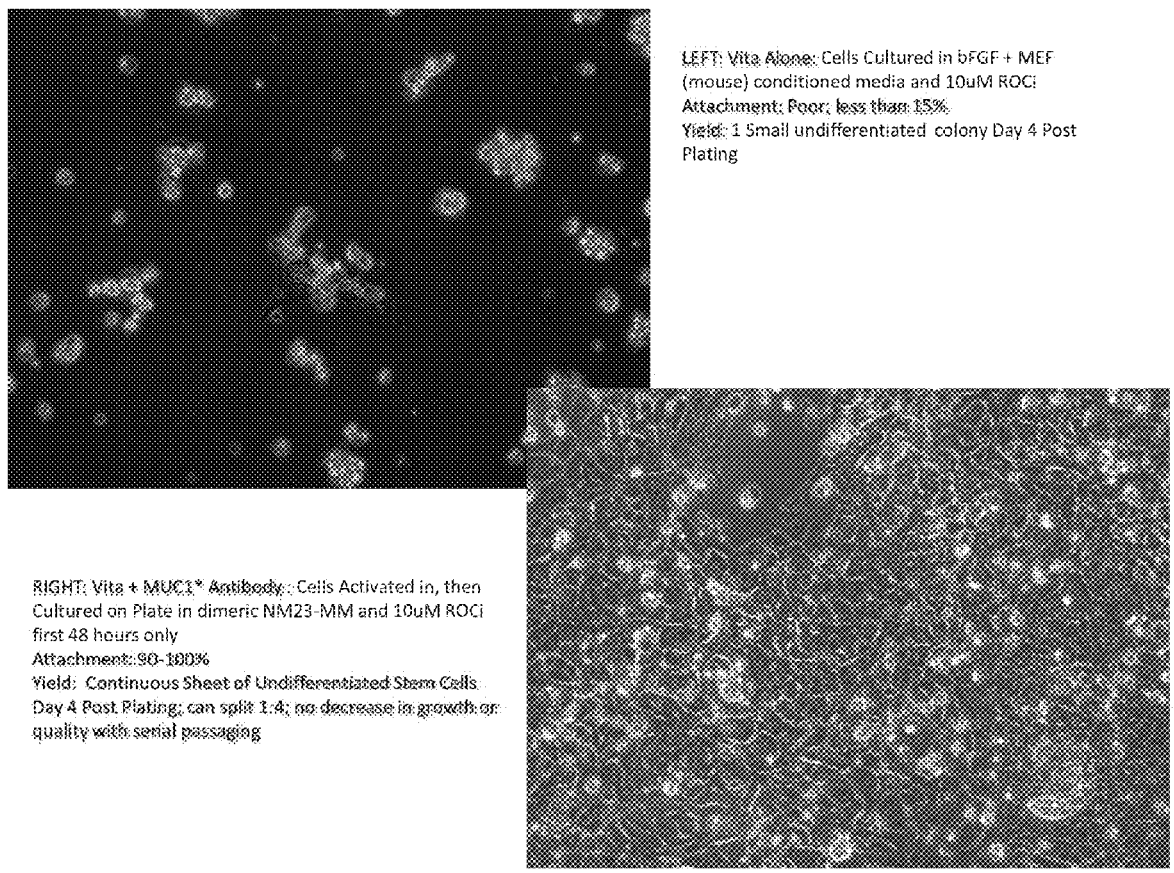
FIG. 12e shows images of human ES cells that were plated onto a Vita surface (no antibody coating) and cultured in standard bFGF plus MEF conditioned media and in the presence of ROCi (upper) compared to the same source cells plated onto a Vita plate coated with an anti-MUC1* antibody and cultured in 8 nM NM23-MM in the presence of ROCi for the first 48 hours only. Images taken Day 4 post plating, see Example 5.

The first part of the experimental setup is shown in FIG. 10. The harvested cells were first pre-incubated in NM23-MM for 15 minutes then rinsed and plated in 1 mL MM per well. 8 nM NM23-S120G was added to a final volume of 4 mLs per well after only 15 minutes. As can be seen in FIG. 11, the Rho kinase inhibitor (ROCi) prevents the clustering of stem cells in solution before they attach to the surface. Although at the end of the experiment, there were comparable numbers of colonies of comparable quality, these results indicate that more colonies would have arisen from a Vita plus antibody surface with ROCi added to NM23-MM at least for the first 24-48 hrs. In fact when ES or iPS cells from any source are trypsinized to single cell suspensions, pre-incubated in low nanomolar concentrations of NM23 in dimer form for at least 15 minutes if previously cultured in bFGF, and plated onto a surface coated with an anti-PSMGFR antibody then cultured in low nanomolar NM23dimers plus a ROCi for the first 24-48 hours, stem cell attachment and proliferation in the undifferentiated state was increased by at least 10-100 times. FIG. 12a shows human ES H9 cells that were harvested from culture in 8 nM NM23dimers-MM over mouse embryonic fibroblast (MEF) feeders, plated onto a Vita surface coated with D26C3 anti-PSMGFR antibody at varying concentrations and in 10 uM ROCi for the first 48 hours only and imaged at DayS post plating. FIGS. 12b-d are magnified photos of these cells.

Example 5

Improvement to Vita Surface Technology

In this experiment, we compared human stem cell attachment, growth and resistance to spontaneous differentiation for human ES cells, previously cultured in bFGF on MEF feeder cells, then plated as single cells onto: a) a Vita surface, then cultured in 4 ng/mL bFGF, 50% MEF conditioned media and 10 uM ROCi (Y-27632, Calbiochem); or b) Vita plate coated with 12.5 ug/mL D26C3 anti-PSMGFR antibody then cultured in 8 nM NM23dimers-MM with 10 uM ROCi present for the first 48 hours only. The comparison, shown in FIG. 12e shows improvement over the state of the art, which did not include coating the surface with anti-PSMGFR antibody or culturing cells in NM23dimers-MM.

Example 6

The Need for Rho Kinase Inhibitor can be Eliminated

In a direct comparison of stem cell attachment in the presence or absence of the ROCi, we observed that in the absence of ROCi, the stem cells clumped up before they attached to the surface. Some colonies formed beneath the clumps of cells, but more often the cell clumping was inhibitory to the process of stem cell attachment to the surface. It appeared that the improvement we observed for stem cell attachment in the presence of a ROCi was that it kept the cells separate as single cells until they attached to the surface. Alternatively, good stem cell attachment was achieved by trypsinizing the stem cells prior to plating. The addition of EDTA (we used 0.1 to 1.0 mM EDTA) also increased stem cell adhesion to the surfaces. In another method, centrifuging the plates with the stem cells in solution brought the cells in contact with the surface and resulted in stem cell attachment and subsequent growth that was indistinguishable from cases in which 10 uM ROCi was present for the first 24-48 hrs after plating.

Figure 19:
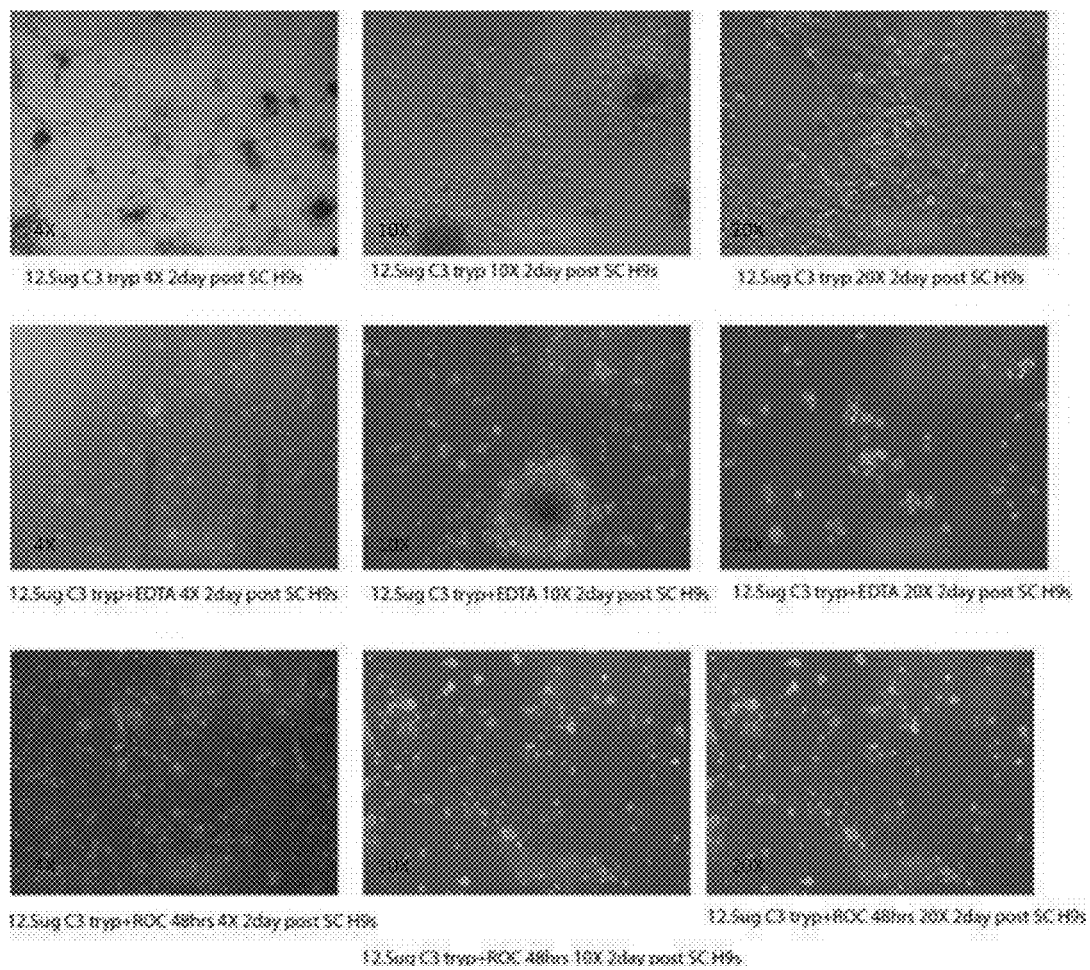
FIG. 19 shows photos of the experiment described in Example 6 comparing attachment of stem cells to surfaces when stem cells were trypsinized prior to plating and in the presence or absence of EDTA or ROCi.
Figure 20:
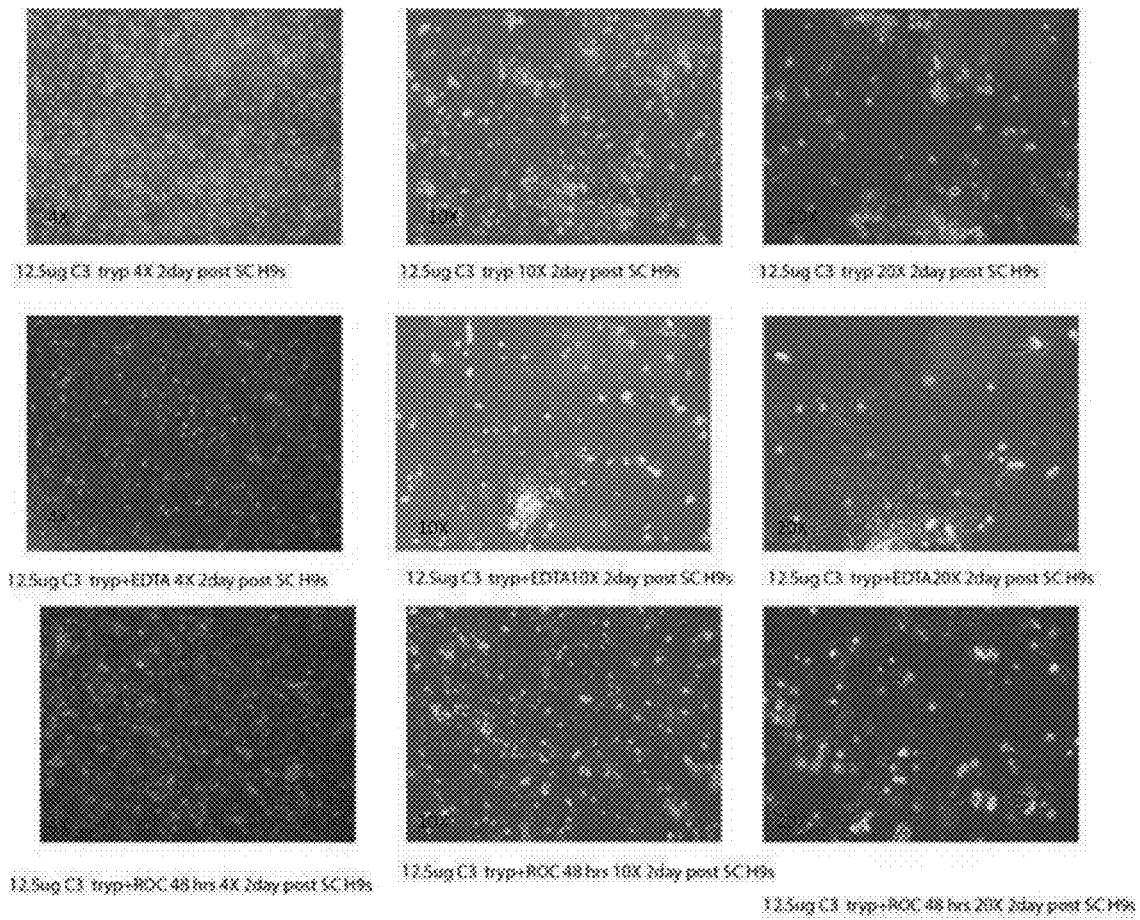
FIG. 20 shows photos of the same experiment described in Example 6 and shown in FIG. 19 with the exception that force was used to bring cells into contact with the surface by centrifuging the plate after cells were plated. Images show that trypsinization plus application of force eliminated need for a Rho kinase inhibitor.

In a model experiment, human ES H9 cells were plated onto a Vita surface coated with an anti-PSMGFR antibody (2D6C3) and the cells were in NM23-MM; the cells were either trypsinized (top row), trypsinized and in 1 mM EDTA (middle), or trypsinized and in presence of 10 uM ROCi (bottom row). As can be seen in FIG. 19, trypsin alone still results in clumping of cells and poor attachment to the surface, trypsin plus EDTA improved cellular attachment but caused the cells to differentiate into neuronal-like phenotype. FIG. 20 shows that under the same conditions, centrifuging the plates greatly improved the attachment of stem cells to the surface. After cells were plated, the plates were centrifuged using a swinging bucket centrifuge at 1200 RPMs for 3-5 minutes. As FIG. 20 shows, physically bringing the cells to the surface eliminated cell clumping and eliminated the need for Rho kinase inhibitor. Similar results can be attained by applying pressure to the cell containing media or any or method that results in an increased probability that the cells will physically meet the surface rather than with a neighboring cell.

Figure 21:
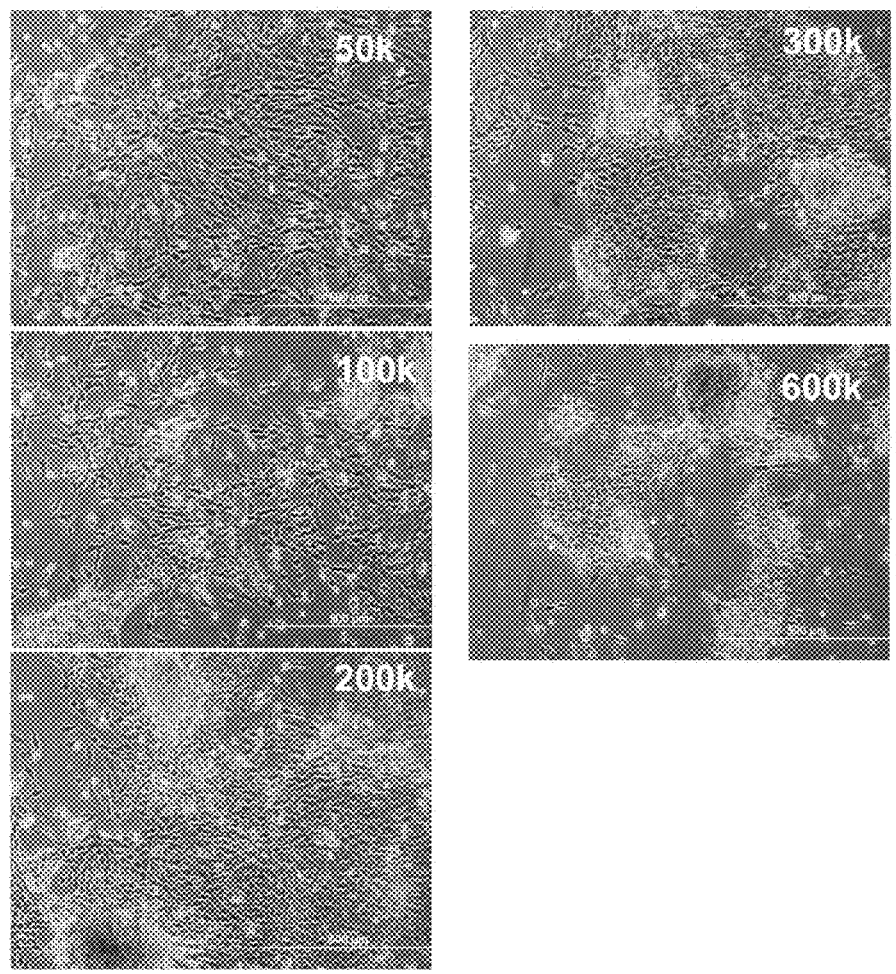
FIG. 21 shows photos of human ES cells plated in the presence or absence of a ROCi and shows that plating trypsinized cells at very low density eliminates the need for a Rho kinase inhibitor to facilitate cellular attachment.

In an alternative method, we found that the use of a Rho Kinase inhibitor could also be eliminated by simply decreasing the plating density of the cells. Cells plated at 25,000 or 50,000 cells per well of a 6-well plate in NM23-MM alone (no ROCi) attached to the surface are proliferated normally and as well as if ROCi had been present. In the experiment shown in FIG. 21, BGO1V/hOG cells were trypsinized, counted and plated at either 25,000 or 50,000 cells per well of a 6-well plate and cultured for 7 days in NM23-MM. No ROCi was used and the cells attached and proliferated indistinguishably from those in which ROCi had been present.

Figure 26:
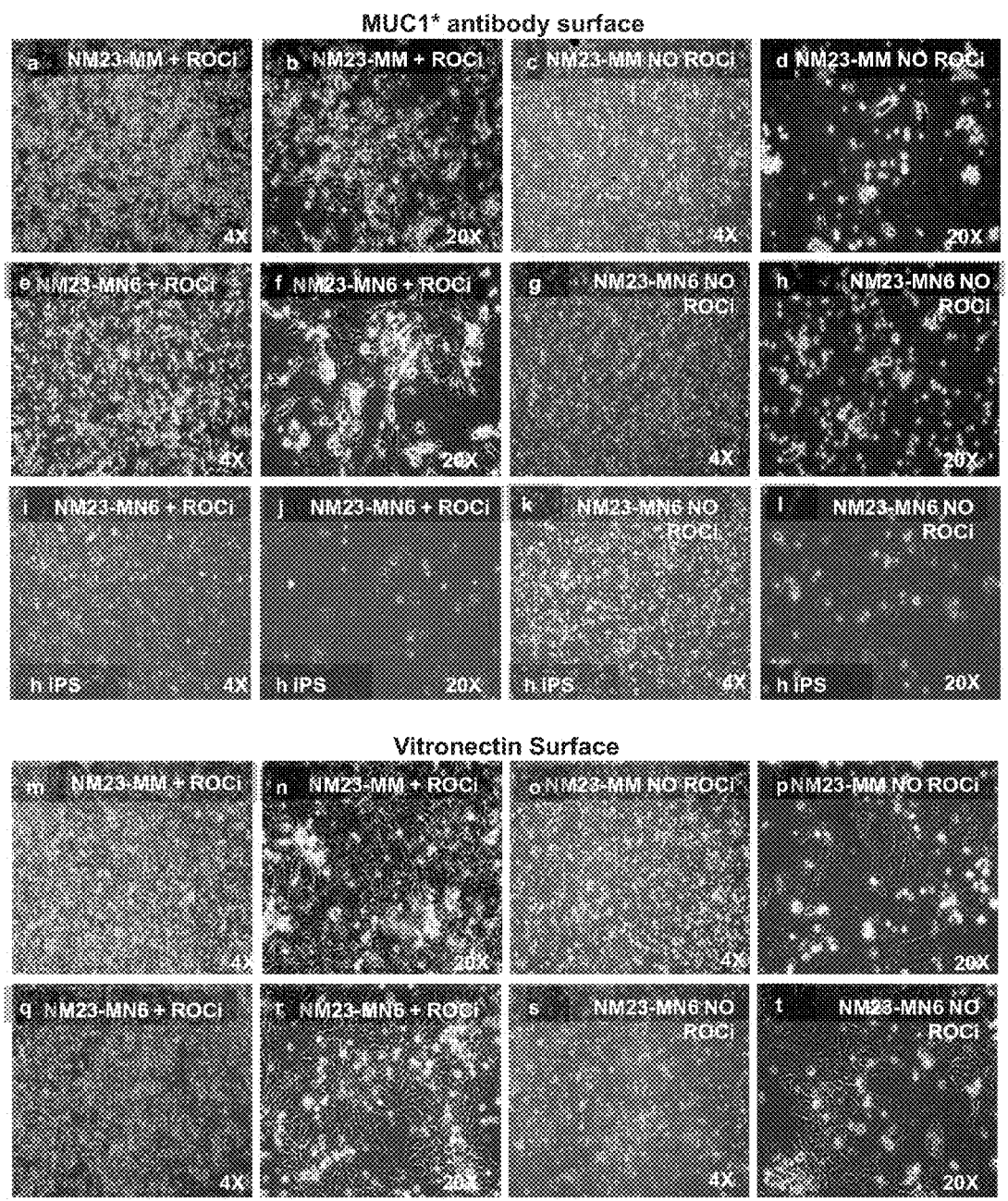

In yet another method, the need for a rho kinase inhibitor is eliminated by simplifying the composition of the base media. Media that contained low nanomolar concentrations of dimeric NM23 but did not contain serum albumin or beta mercaptoethanol eliminated the need for ROCi. For example, human H9 cells cultured in NM23-MN6 (DMEM/F12/GlutaMAX or similar base media suitable for cell culture, supplemented with 1% non-essential amino acids, 64 mg/L ascorbic acid (Sigma), 14 ug/L sodium selenium (Sigma), 19.4 mg/L insulin (Sigma), 543 mg/L sodium bicarbonate (Sigma) and 10.7 mg/L transferrin (Sigma)) did not require the use of a ROCi for 70-90% attachment of stem cells and optimal cell survival. FIG. 26.

Example 7

Different NM23 Multimers are Generated and Assayed for Function

Example 7.1

Cloning of Recombinant NM23-wt and NM23-S120G

WT NM23-H1 cDNA was amplified by polymerase chain reaction (PCR) using the following primer: 5'-atc gat gga tcc gat ggc caa ctg tga gcg tac c-3' (SEQ ID NO:38) and 5'-gtg gtg ctc gag ttc ata gat cca gtt ctg agc-3' (SEQ ID NO:39). After digestion with BamHI and XhoI restriction enzymes (New England Biolabs), the purified fragment was cloned into the pET2 1b vector (Novagen) digested with the same restriction enzymes. We then generated the NM23-H1 mutant S120G (serine #120 mutated to a glycine) using the GeneTailor™ Site-directed mutagenesis system (Life Technologies) following the manufacturer instructions using the following primers: 5'-gcaggaacattatacatggcggtgattctg-3' (SEQ ID NO:40) and 5'-gccatgtataatgttcctgccaacttgtat-3' (SEQ ID NO:41). After sequence confirmation, the WT and mutant NM23-H1 constructs were transformed into BL21 (DE3) cells (Life Technologies) for recombinant protein expression.

NM23 S120G - DNA sequence
(SEQ ID NO: 42)
atggccaactgtgagcgtaccttcattgcgatcaaaccagatggggtcca gcggggtcttgtgggagagattatcaagcgttttgagcagaaaggattcc gccttgttggtctgaaattcatgcaagcttccgaagatcttctcaaggaa cactacgttgacctgaaggaccgtccattctttgccggcctggtgaaata catgcactcagggccggtagttgccatggtctgggaggggctgaatgtgg tgaagacgggccgagtcatgctcggggagaccaaccctgcagactccaag cctgggaccatccgtggagacttctgcatacaagttggcaggaacattat acatggcggtgattctgtggagagtgcagagaaggagatcggcttgtggt ttcaccctgaggaactggtagattacacgagctgtgctcagaactggatc tatgaactcgagcaccaccaccaccaccactga NM23 S120G - amino acid sequence
(SEQ ID NO: 43)
MANCERTFIAIKPDGVQRGLVGEIIKRFEQKGFRLVGLKFMQASEDLLKE

HYVDLKDRPFFAGLVKYMHSGPVVAMVWEGLNVVKTGRVMLGETNPADSK

PGTIRGDFCIQVGRNIIHGGDSVESAEKEIGLWFHPEELVDYTSCAQNWI

YELEHHHHHH

Example 7.2

Recombinant NM23-Wt and NM23-S120G Expression/Purification

LB broth (Luria-Bertani broth) was inoculated with ⅒ of an overnight culture and cultured at 37° C. until OD600 reached ~0.5. At this point, recombinant protein expression was induced with 0.4 mM Isopropyl-β-D-thio-galactoside (IPTG, Sigma) and culture was stopped after 4 h. After harvesting the cells by centrifugation (6000 rpm for 10 min at 4° C.), cell pellet was resuspended with running buffer: PBS pH7.4, 360 mM NaCl and 80 mM imidazole. Then lysozyme (1 mg/mL, Sigma), $MgCl_2$ (0.5 mM) and DNAse (0.5 ug/mL, Sigma) was added. Cell suspension was incubated on a rotating platform (275 rpm) for 30 min at 37° C. and sonicated on ice for 5 min. Insoluble cell debris was removed by centrifugation (20000 rpm for 30 min at 4° C.). The cleared lysate was then applied to a Ni-NTA column (Qiagen) equilibrated with the running buffer. The column was washed before eluting the protein off the column with the running buffer supplemented with 420 mM imidazole. The elution fractions were analyzed on a non-reducing SDS-PAGE and fractions containing the protein were combined. All components were from Sigma unless otherwise stated.

Example 7.3

Protein Refolding

NM23 H1 S120G was denatured with denaturing buffer: 100 mM Tris pH 8.0 and 8M urea. The denatured protein was then subjected to refolding by dialysis. The protein was dialyzed successively for 24 h against: 1) 100 mM Tris pH8.0, 4M urea, 0.2M imidazole, 0.4M L-Arginine, 1 mM EDTA (Fluka) and 5% glycerol (Acros), 2) 100 mM Tris pH8.0, 2M urea, 0.2M imidazole, 0.4M L-Arginine, 1 mM EDTA and 5% glycerol and 3) 100 mM Tris pH8.0, 1M urea, 0.2M imidazole, 0.4M L-Arginine, 1 mM EDTA and 5% glycerol. The protein was then dialysed against 100 mM Tris pH8.0, 0.2M imidazole, 0.4M L-Arginine, 1 mM EDTA and 5% glycerol for 9 h and against 25 mM Tris pH8.0, 0.2M imidazole, 0.1M L-Arginine, 1 mM EDTA and 5% glycerol overnight. Finally, the protein was dialyzed against PBS pH7.4, 0.2M imidazole, 1 mM EDTA and 5% glycerol for 24 h with four buffer changes. All components were from Sigma unless otherwise stated. Insoluble aggregate was removed by centrifugation (20000 rpm for 30 min at 4° C.) and the dimer (~37 KDa) was purified by size exclusion chromatography on a Superdex 200 10/300 GL column (GE healthcare) using PBS pH7.4 as running buffer. The peak fractions were analyzed on a non-reducing SDS-PAGE and fractions containing the dimer were combined.

Example 7.4

Protein Oligomerization State

The oligomerization state of the NM23 proteins was estimated by size exclusion chromatography using a Superdex 200 10/300 GL column (GE healthcare) calibrated with gel filtration standards (Bio-Rad). A significant feature of NM23 function is its multimerization state, wherein the dimeric form of NM23 is the active form that promotes pluripotency and cell growth.

Figure 22:
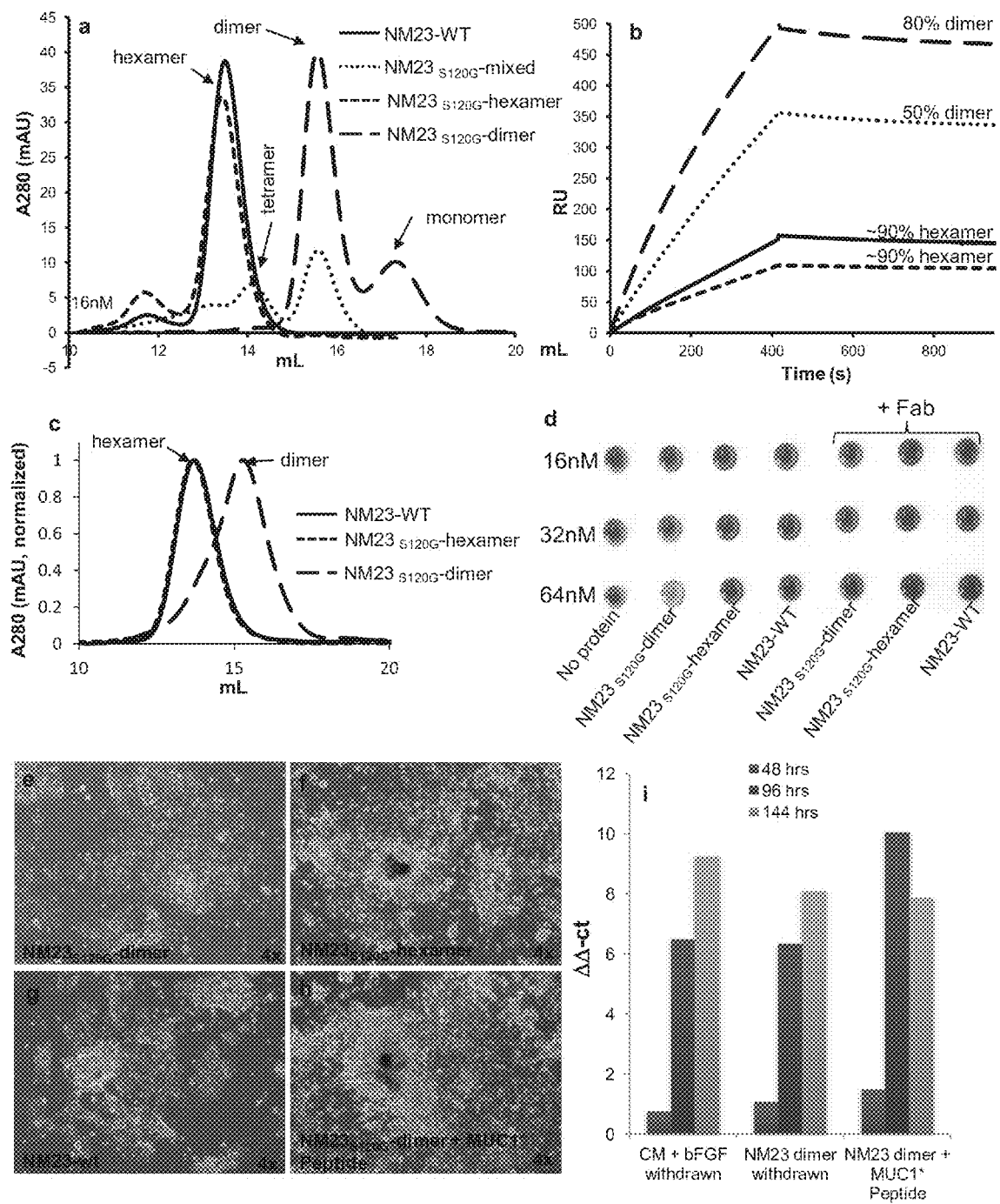
FIGS. 22a-i show the results of the experiments described in Example 7. a) is an overlay of FPLC traces showing the multimerization state of recombinant NM23 wild type (wt), NM23-S120G-hexamer which was the soluble fraction of the expressed protein, the NM23-S120G-dimer that was denatured and refolded according to Example 7 to produce mostly dimers, and NM23-S120G-mixed which was a mixture of the hexamers, tetramers and dimers was generated such that it contained ~50% dimer. b) is an overlay of Surface Plasmon Resonance (SPR) traces from experiments that tested the ability of the NM23 preparations shown in part (a) to determine their ability to bind to a synthetic MUC1* extra cellular domain (ecd) peptide (PSMGFR). The amount of NM23 binding to the MUC1* peptide corresponds to the concentration of dimer present in each sample. c) is an overlay of FPLC traces characterizing recombinant NM23-wt, $NM23_{S120G}$-hexamer and $NM23_{S120G}$-dimer containing the Strep-tag II. d) is a photograph of a nanoparticles experiment testing the ability of the various NM23 multimers to bind to the $MUC1*_{ecd}$ peptide (PSMGFR-His tagged) that was immobilized onto gold NTA-Ni-SAM-coated nanoparticles. A nanoparticle color change from pink to blue/gray indicates binding. (e-h) shows the functional effect of the various NM23 multimers on stem cell pluripotency. Loss of pluripotency is seen as dark or thickened areas of cells. i) is a graph of the measured amounts of microRNA-145 in response to withholding bFGF, NM23-dimers or competitively inhibiting the NM23-dimer-UC1* interaction. An increase in miR-145 signals the cell's exit from pluripotency and onset of differentiation.

NM23 H1 isoform was expressed as both the wild type protein (wt) and also bearing the single point mutation, S120G. Analysis by size exclusion chromatography (FIG. 22a), native gel, and Western blot (FIG. S22) indicated that, at concentrations from 8 nM to 13 uM, soluble NM23-wt and soluble NM23-S120G was predominantly hexameric ($NM23_{S120G}$-hexamer). However, using the protein refolding method given above, $NM23_{S120G}$ was denatured and refolded to produce a population consisting primarily of dimer, and which was further purified by size exclusion chromatography to recover a stable population of essentially all dimer ($NM23_{S120G}$-dimer). Thus, we produced NM23-wt and S120G mutant that were both comprised of hexamers and refolded, FPLC purified $NM23_{S120G}$ that was essentially all dimer (FIG. 22a and FIG. S22a-b).

We tested the ability of NM23 hexamers and dimers to bind to the MUC1*$_{ecd}$ peptide in a direct binding assay using Surface Plasmon Resonance, in a Biacore 3000 instrument. A synthetic MUC1*$_{ecd}$ peptide (PSMGFR-HIS$_6$ $_{tag}$) was immobilized onto a gold chip. NM23-wt, $NM23_{S120G}$-dimer, $NM23_{S120G}$-hexamer, or a sample containing 50% of $NM23_{S120G}$ dimers were separately flowed over the peptide surfaces. The amount of NM23 that bound to the peptide surface was a function of the amount of dimer present in each sample (FIG. 22b). $NM23_{S120G}$-dimers showed robust binding to the immobilized MUC1* peptide, while NM23-wt and $NM23_{S120G}$-hexamer, which are mainly hexamers, showed minimal binding. Note that the SPR signal is directly proportional to the mass of the molecular species bound at the solution-peptide surface interface. Therefore, if the hexameric form of NM23 bound to the MUC1* peptide surface, the greater mass of the hexamer should result in 3-times more resonance units (RUs) than the dimer. The fact that the amount of hexamer binding was minimal is consistent with the idea that NM23 hexamers do not bind to the MUC1* receptor.

A nanoparticle assay was used to characterize the binding of NM23 dimers versus hexamers. A MUC1*$_{ecd}$ peptide (QFNQYKTEAASRYNLTISDVSVSDVPFPFSAQSGAH-HHHHH) (SEQ ID NO:44) was immobilized on NTA-SAM-coated gold colloids. NM23-wt, $NM23_{S120G}$-dimer and $NM23_{S120G}$-hexamer were expressed and purified with the Strep-tag II (FIG. 22c). The addition of $NM23_{S120G}$-dimer induced a pink to blue solution color change, indicating a specific binding, which was then inhibited by the addition of an anti-MUC1* Fab. Conversely, the addition of NM23-wt or $NM23_{S120G}$-hexamer did not induce a color change, indicating that the hexamers do not bind to the MUC1* receptor (FIG. 22d).

The different NM23 multimers were tested for their ability to maintain pluripotent stem cell growth. Human H9 ES cells were cultured in minimal media (MM) with either NM23-wt, $NM23_{S120G}$-dimer or $NM23_{Ss120G}$-hexamer. $NM23_{S120G}$-dimers, produced completely undifferentiated stem cells (FIG. 22e), but $NM23_{S120G}$-hexamer and NM23-wt (mostly hexamers) rapidly differentiated (FIG. 22f, g). To further demonstrate that it is the specific interaction of NM23-dimers with MUC1* extra cellular domain that promotes pluripotent growth, we added the synthetic MUC1*$_{ecd}$ peptide (PSMGFR) to stem cells growing in NM23-dimers in minimal media to competitively inhibit this interaction. Disruption of the NM23 dimer-MUC1* interaction resulted in the highest degree of differentiation (FIG. 22h).

Example 7.5 miR-145 Spikes when NM23-MUC1* Interaction is Inhibited

An increase in miR-145 expression signals the stem cells' exit from pluripotency. When growth factor is withheld from stem cell media, which is the standard method for inducing differentiation, there is a corresponding spike in miR-145 expression. RT-PCR measurements showed that competitive inhibition of the $NM23_{S120G}$-dimer-MUC1* interaction by the free MUC1*$_{ecd}$ peptide resulted in an earlier and larger spike in the expression of miR-145 than that caused by allowing cells to differentiate by simply withholding the growth factor $NM23_{S120G}$-dimer or bFGF (FIG. 22i). These results demonstrate that it is the specific interaction of $NM23_{S120G}$-dimer binding to the extra cellular domain of the MUC1* growth factor receptor that promotes pluripotency.

Total RNA was extracted from the samples using the mirVana™ kit (Applied Biosystem, P/N: AM1561) per manufacturer's instructions. For each total RNA sample, two cDNA samples were synthesized using the TaqMan® MicroRNA Reverse Transcription Kit (Applied Biosystems, P/N: 4366596) and two different stem-loop primers specific for miR-145 and the small nuclear RNA U6B (RNU6B), which served as an endogenous control. Quantification of miR-145 and RNU6B in the cDNA samples was performed using TaqMan® MicroRNA Assays (Applied Biosystems, P/N: 4427975) per manufacturer's instructions. The real-time PCR data were analyzed using the comparative $C_t$ method. The relative amount of miR-145 in each sample was obtained by computing the difference between the miR-145 $C_t$ and the corresponding RNU6B $C_t$ ($\Delta C_t$). A second normalization was performed by subtracting the smallest $\Delta C_t$ from all the others in the data set ($\Delta \Delta C_t$).

FIG. 22a shows recombinant NM23 wild type and NM23-S120G mutant were expressed using different protocols that resulted in the formation of different multimerization states and characterized, then purified by size exclusion chromatography. The NM23-S120G mutant was denatured and refolded using a protocol that produces a stable population of dimers. A mixture of the hexamers, tetramers and dimers was generated such that it contained ~50% dimer. FIG. 22b shows that NM23-S120G or wild type multimers were tested by Surface Plasmon Resonance (SPR) to determine their ability to bind to a synthetic MUC1* extra cellular domain (ecd) peptide. The amount of NM23 binding to the MUC1* peptide corresponds to the concentration of dimer present in each sample. FIG. 22c shows recombinant NM23-wt, NM23$_{S120G}$-hexamer and NM23$_{S120G}$-dimer containing the Strep-tag II were characterized by size exclusion chromatography. FIG. 22d shows nanoparticles presenting the MUC1*$_{ecd}$ peptide were mixed with NM23-wt, NM23$_{S120G}$-dimers or -hexamers containing the Strep-tag II. A nanoparticle color change from pink to blue/gray indicates binding. NM23 dimers bind to the MUC1*$_{ecd}$ peptide at 64 nM while the hexamers, whether wild type or S120G mutant, do not. The interaction was competitively inhibited by an anti-MUC1* Fab, showing that the color change was due to the specific interaction between NM23-dimers and MUC1*$_{ecd}$. H9 hES cells were cultured in NM23$_{S120G}$-dimers (FIG. 22e), NM23$_{S120G}$-hexamers (FIG. 22f), wild type (FIG. 22g) or NM23$_{S120G}$-dimers plus a synthetic MUC1*$_{ecd}$ peptide (FIG. 22h). Only NM23$_{S120G}$-dimers supported pluripotent stem cell growth. Hexamers or inhibition of the NM23$_{S120G}$-dimers-MUC1* interaction resulted in immediate differentiation. FIG. 22i shows that H9 hES cells were cultured in either bFGF plus conditioned media or in NM23$_{S120G}$-dimers, then allowed to differentiate by withholding the growth factor. Some cells cultured in NM23$_{S120G}$-dimers continued to receive the growth factor but were also given the MUC1*$_{ecd}$ peptide to competitively inhibit the NM23-MUC1* interaction. miR-145, a marker for exit from pluripotency, is measured by RT-PCR as a function of time.

FIG. S22 shows protocol developed that produces recombinant NM23 as a stable population of dimers. FIG. 22a shows recombinant NM23-wt or S120G mutants that had been purified from the soluble portion, denatured then refolded to form a dimer population or preparation that resulted in an approximate 50/50 mix of dimers and hexamers were analyzed on a native gel to determine which protocols produced which multimers. Protein was loaded at 5 ug and Mug total protein per well. FIG. 22b shows that Western blot was performed on a native gel in which the various preparations of NM23-wt or S120G mutant were loaded at very low concentrations comparable to those used in our stem cell culture (8, 16 and 32 nM). FIG. 22c shows that The stability of NM23$_{S120}$-dimer under culture conditions was tested. NM23$_{S120G}$-dimer was added to cell culture media and kept in a CO$_2$ incubator for up to 48 hours, then analyzed by SDS-PAGE, which showed that no denaturation occurred within the time frame required for use in stem cell culture.

Example 8

Figure 23:
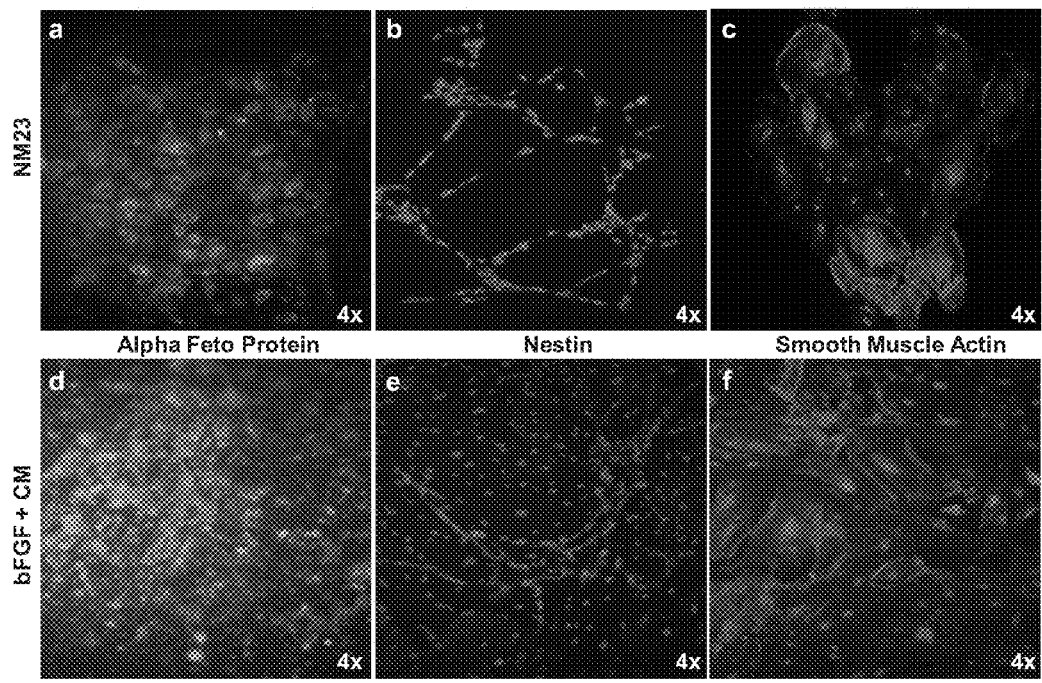
Figure 24:
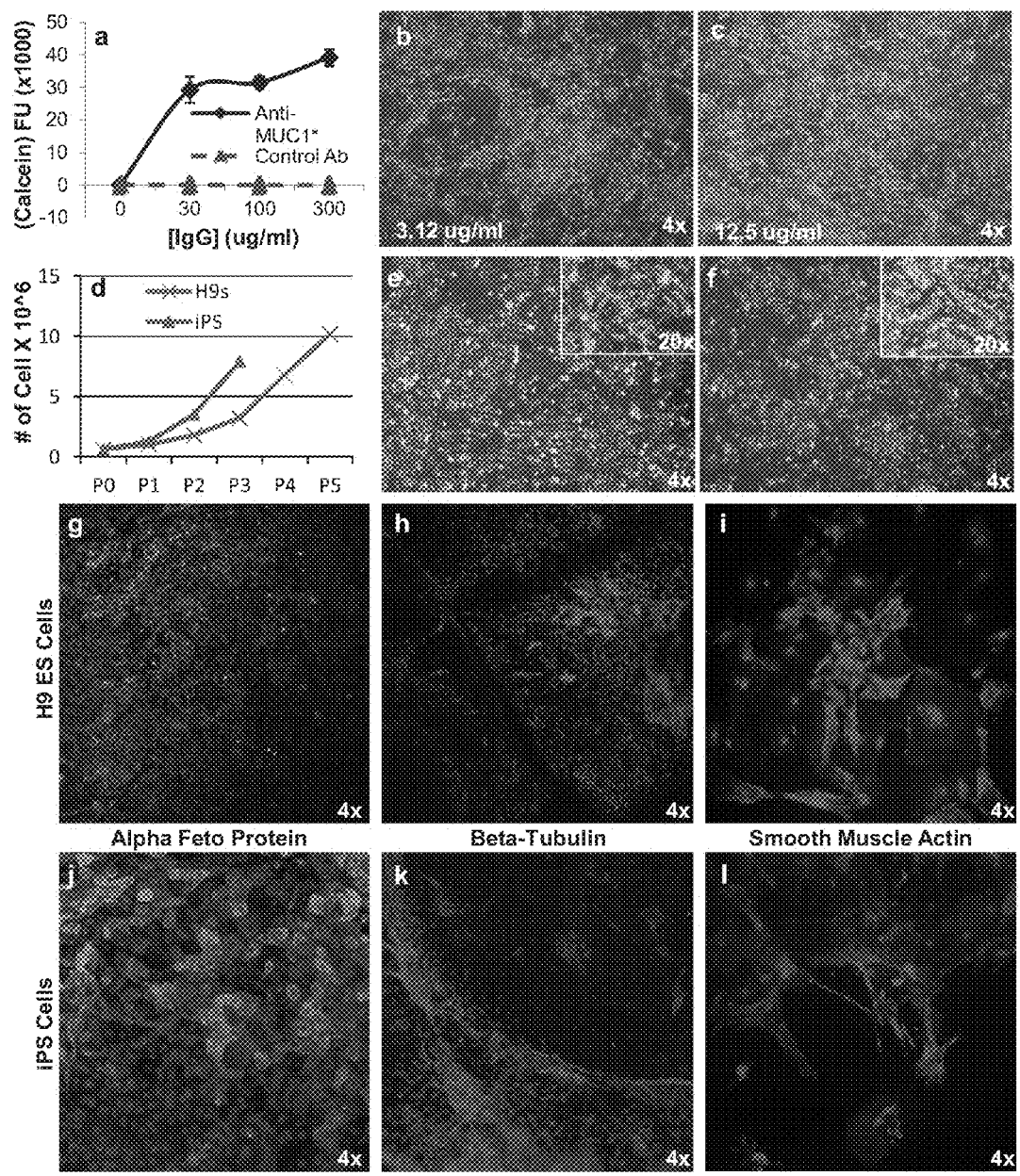

Human ES cells cultured long-term in NM23-MM differentiate normally down all three germlines and in most cases displayed coordinated differentiation. H9 hES cells on Matrigel were cultured for six passages in either 8 nM NM23 dimers in MM (minimal stem cell media) or in 4 ng/mL bFGF in MM plus MEF conditioned media, then allowed to differentiate by the embryoid body method. Subsequent staining with nuclear marker DAPI and antibodies against markers of the three germlines: FIG. 23a shows endoderm—alpha feto protein, FIG. 23b shows ectoderm—nestin, and FIG. 23c shows mesoderm—smooth muscle actin. Stem cells cultured in NM23-MM differentiated down all three germlines, wherein most cells in a single cluster stained positive for the same marker. Stem cells cultured in bFGF and MEF conditioned media also differentiated down all three germlines but more often did not display coordinated differentiation, wherein nuclei of nearest neighbors stain negative for the germ line marker being tested (FIGS. 23d-23f).

Example 9

MN-C3 (2D6C3), a Monoclonal Anti-MUC1* Antibody Coated onto Plastic Cell Culture Plates Fully Supports Pluripotent Stem Cell Growth in Combination with Our NM23-Minimal Media 2D6C3 or 2D6C8 monoclonal antibody was coated onto the surfaces of tissue culture treated plates at concentrations from 3.25 to 125 ug/mL and incubated at room temperature for 3 hours or at 4 degrees C. overnight. Human ES and iPS cells readily attached and could be serially passaged on these antibody-coated surfaces. The resultant stem cells were pluripotent as evidenced by ICC staining and RT-PCR for the pluripotency markers.

Example 9.1

Stem Cell Growth Surface

A Vita surface was coated with a monoclonal MUC1*$_{ecd}$ antibody (D26C3) that functions as both a method for stem cell attachment and for stimulating growth by dimerizing the MUC1* receptor. FIGS. 24a-c show that stem cells attached and proliferated as a function of the D26C3 antibody coating density, whereas no stem cell attachment was observed when control antibodies were used. Stem cells proliferated on these MUC1* antibody surfaces even when cultured in minimal stem cell media alone, in the absence of any growth factor—NM23 or bFGF—due to the dimerization of MUC1* from the surface-immobilized antibodies. However, the growth rate was vastly improved by the use of NM23 in the minimal media. In some cases, a Rho kinase inhibitor was present during the first 48 hours, which increased attachment to the surfaces, but did not affect survival. ES and iPS cells were serially passaged on these MUC1* antibody surfaces in NM23-MM for more than 20 passages without a decrease in growth rate or pluripotency. Furthermore, stem cells growing on MUC1* antibody surfaces in NM23-MM undergo a dramatic increase in growth rate with each consecutive passage. By the fourth passage, 600,000 iPS cells plated increased 13-fold to 7.9M undifferentiated stem cells in four days. Similarly, by the fifth passage, H9 cells increased 17-fold (FIGS. 24d-f). ICC staining for the typical pluripotency markers confirmed that the cells were pluripotent and had normal karyotype (FIG. S24a and S24b). In addition, the resultant ES and iPS cells were able to differentiate down all three germlines (FIG. 24g-l). In summary, growth in NM23-MM on D26C3 antibody surfaces produced more undifferentiated stem cells, in less time, with no manual dissection.

FIG. 24a shows that an anti-MUC1* rabbit polyclonal antibody or a control IgG antibody were adsorbed at varying concentrations onto a tissue culture treated surface. BGO1V/hOG hES cells were plated onto the surfaces and allowed to grow for 96 hours. A Calcein assay to quantify cell number was performed. BGO1V/hOG hES cells were cultured for 20 passages in NM23-MM without a decrease in pluripotency or change in karyotype. H9 hES cells were plated onto Vita surfaces coated with 3.12 ug FIG. 24b or 12.5 ug FIG. 24c of a monoclonal anti-MUC1* antibody, MN-C3. Cells attached and proliferated as a function of antibody concentration. FIG. 24d shows the growth rate of human H9 ES cells or iPS cells increased exponentially after being plated onto the antibody coated surfaces and cultured in NM23-MM. We grew human ES and iPS cells on MN-C3 coated Vita™ plates and cultured them in NM23-MM. At the start of each passage 600,000 cells were plated and then counted after a growth period of 4-6 days. This was repeated for 5-6 passages, each time starting with 600,000 cells from the previous passage. By the fourth passage, 600,000 iPS cells plated increased 13-fold to 7.9M undifferentiated stem cells in four days. By the fifth passage, H9 cells increased 17-fold. It was noted that after three (3) passages on the MN-C3 surfaces, both ES and iPS cells grew to nearly 100% confluency by Day 4 with essentially no differentiation. Photos were taken of the iPS cells (FIG. 24e) and H9 ES cells (FIG. 24f) cultured in NM23-MM on MN-C3 antibody surfaces after passage 4. After 6 passages, resultant cells were allowed to differentiate by embryoid body method. Staining with nuclear marker DAPI and antibodies against markers of the three germlines, endoderm—alpha feto protein (FIGS. 24g and 24j), ectoderm—beta-tubulin (FIGS. 24h and 24K)), and mesoderm—smooth muscle actin (FIGS. 24i and 24l) show that the cells differentiate normally after serial passaging in NM23-MM on anti-MUC1*-coated surfaces.

FIG. S24a shows that hES cultured in NM23-MM on a novel and defined surface for at least 7 passages express typical pluripotency markers. H9s cells on a monoclonal anti-MUC1* antibody (MN-C3) surface were assayed for the presence of the typical pluripotency markers after seven passages. Cells stained positive for typical pluripotency markers and had normal karyotype.

FIG. S24b shows that iPS cultured in NM23-MM on a novel and defined surface for at least 7 passages express typical pluripotency markers. iPS cells (iPS FTD19 clone 42) on a monoclonal anti-MUC1* antibody (MN-C3) surface were assayed for the presence of the typical pluripotency markers after seven passages. Cells stained positive for typical pluripotency markers and had normal karyotype.

Example 10

Human Stem Cells Cultured in NM23-MM Over MUC1* Antibody Surfaces Express Higher Levels of Naïve Cell Markers and Lower Levels of Primed Cell Markers Example 10.1

Naïve or Primed Cells

To further assess the quality of stem cells cultured in NM23-MM on MUC1* antibody surfaces, we measured expression levels of genes that are indicators of human stem cells being in the "naïve" or ground state. Klf4 and Klf2 are usually high in naïve stem cells, while FoxA2 and XIST (an indicator of X-inactivation) are very low or not expressed. The reverse pattern of gene expression happens when cells are in the "primed" state, which is a more differentiated state. We compared expression levels of these genes in stem cells that were cultured in either NM23-MM on MUC1* antibody surfaces, bFGF on MEF feeder cells or mTeSR on Matrigel. Stem cells cultured in NM23-MM on MUC1* antibody surfaces expressed higher levels of the naïve markers and lower levels of the primed markers than cells cultured in bFGF on MEFs. Cells cultured in mTeSR on Matrigel expressed higher levels of Foxa2 and XIST, which are indicators of the primed state, and lower levels of some of the naïve markers compared to cells cultured in bFGF over MEFs (FIG. 25a).

With successive passage number, a trend toward the naïve state was noted when NM23-MM was used (FIG. 25c), but not when mTeSR was used (FIG. 25b). FIG. 37 shows RT-PCR measurements of human stem cells cultured in bFGF over MEF feeders (n=3), mTeSR over Matrigel (n=5) or NM23-S120G dimers in minimal stem cell media over a Vita surface coated with 12.5 ug/ml of 2D6C3 the monoclonal anti-MUC1* antibody (n=6). In this experiment, two additional primed cell markers, OTX2 and LHX2, were also measured. The graph of FIG. 37 shows that consistent with other experiments, growth in NM23 over a surface presenting ligands for MUC1* increases expression of naïve markers and decreases expression of primed markers.

To assess the contribution of surface alone, we plated ES cells that had been growing for 45 passages in bFGF on MEFs onto a layer of recombinant Vitronectin. The cells were then cultured in either NM23-MM, bFGF plus MEF conditioned media or mTeSR for a single passage then assayed for expression of a subset of the naïve and primed markers. Although cells cultured in NM23-MM showed higher expression of the naïve markers and lower expression of the primed markers than either bFGF or mTeSR, growth on Vitronectin resulted in decreased expression of naïve markers and increased expression of primed markers for all the media tested (FIG. 25d). These results show that growth on Vitronectin drives human stem cells to the primed state and negatively impacts the integrity of stem cells.

Example 10.2

Real Time PCR Method for Quantifying Naïve or Primed Gene Expression

Cells grown in different conditions were collected. The cells were pelleted and frozen at −70° C. until time of analysis. Total RNA was extracted from the samples using TRIzol® Reagent (Life Technologies) per manufacturer's instructions. Quantification of FOXa2 (Applied Biosystems, Assay ID: Hs00232764_m1), KLF4 (Applied Biosystems, Assay ID:Hs00358836_m1), NANOG (Applied Biosystems, Assay ID: Hs02387400_g1), KLF2 (Applied Biosystems Assay ID: Hs00360439_g1), XIST (Applied biosystems Assay ID: Hs01079824_m1), OCT4 (POU class 5 homeobox 1) (ABI assay ID Hs00999634_gH) and GAPDH (Applied Biosystems, P/N: 4310884E), in the RNA samples was performed using TaqMan® One Step RT-PCR Master Mix Reagents (Applied Biosystems, P/N: 4309169) per manufacturer's instructions. The real-time PCR data were analyzed using the comparative $C_t$ method. The relative amount of each transcript in each sample was obtained by computing the difference between the target $C_t$ and the corresponding GAPDH ($\Delta C_t$). A second normalization was performed by subtracting the MEF/FGF sample $\Delta C_t$ from all the others in the data set ($\Delta\Delta C_t$).

FIG. 25 shows that RT-PCR was used to quantify expression of a subset of naïve markers that included OCT4, NANOG, KLF4 and KLF2, which should be high in the naïve state, and a subset of primed markers that included XIST and FOXA2, which are high in the primed state. Measurements were normalized to housekeeping gene GAPDH and expressed as fold change to H9 ES cells cultured in 4 ng/ml bFGF over MEFs (control). FIG. 25a shows that H9 ES cells cultured in NM23-MM on MUC1* antibody (MN-C3) surfaces, on average, showed increased expression of naïve markers and decreased expression of primed markers (n=6). Conversely, H9 cells cultured in mTeSR over Matrigel showed decreased expression of naïve markers and increased expression of primed markers (n=5). Individual measurements of the subset of naïve or primed markers are plotted as a function of passage number for NM23-MM over anti-MUC1* antibody surfaces (FIG. 25b) and for mTeSR over Matrigel (FIG. 25c). The trend toward the naïve state increased with successive passage in NM23-MM but not with mTeSR. FIG. 25d shows that to correct for differences due to passage number or surfaces, H9 cells that had been serially passaged in bFGF on MEFs for 45 passages were used as the cell source. Cells were plated onto a layer of vitronectin and cultured in either bFGF plus MEF conditioned media, mTeSR, or NM23-MM for a single passage. All values were expressed as fold change to the control of H9 ES cells cultured in 4 ng/ml bFGF over MEFs and values for NM23-MM over MUC1* antibody surface is added for comparison. Overall, expression of naïve markers decreased and primed markers increased after plating onto vitronectin.

Example 11

NM23 in 6-component Defined and Xeno-free Media Supports Pluripotent Stem Cell Growth on MUC1* Antibody Surfaces We tested the ability of NM23 to support ES and iPS cell growth as the single growth factor in a fully defined, xeno-free 6-component media (MN6). Our results show that NM23-MN6 fully supported serial passaging of pluripotent stem cells on our MUC1* antibody surfaces as well as on other surfaces such as Vitronectin at 12.5 ug per well (FIG. 26a-f). Surprisingly, the use of the MN6 media with NM23 appears to eliminate the need for a Rho Kinase inhibitor in the first 24-48 hours (FIG. 26g-l).

FIG. 26 shows that hES and hiPS cells were serially cultured in NM23 in a 6-component media (MN6) that is fully defined-xeno-free on either a MUC1* antibody surface or on a layer of Vitronectin. FIGS. 26a-26h shows that hES H9s cultured in NM23-MN6 on MN-C3 antibody surface coated onto a Vita™ plate in the presence or absence of a Rho kinase inhibitor (ROCi) for the first 48 hours. FIGS. 26i-26l iPS cells cultured in NM23-MN6 on MN-C3 antibody surface coated onto a Vita™ plate. FIGS. 26m-26t show hES H9 cells cultured in NM23-MN6 on Vitronectin surface coated onto tissue culture treated plates in the presence or absence of a Rho kinase inhibitor (ROCi). The helping effect of a Rho kinase inhibitor for the first 48 hours was minimized when cells were cultured in NM23-MN6 on MN-C3 antibody surfaces.

Example 12

Human Stem Cells Cultured in Either NM23 or FGF Over Human or Mouse Feeder Cells are Probed for the Presence of Markers of Either NaïVe State or Primed State We started with H9 embryonic stem cells that were primed. They had been cultured in bFGF and over mouse MEF feeder cells for approximately 30 passages. A first set of cells was continued to be cultured in bFGF over MEFs. A second group was transitioned onto human feeder cells (HS27s) but still cultured in 4 ng/ml of bFGF. A third set of cells was cultured in NM23-S120G but remained on the mouse MEF feeder cells. A fourth set of the cells was transitioned onto human feeder cells (HS27s) and cultured in NM23-S120G. All cells were cultured according to these conditions for an additional 6 passages. The cells were then stained for the presence of Klf4 which is a marker for naïve stem cell state and Foxa2 which is a marker for the primed stem cell state. FIGS. 27-35 show that only cells cultured in NM23 and exposed to human feeder cells expressed naïve stem cell marker Klf4 and did not express any Foxa2 which is the primed stem cell marker.

Example 13

NM23 Mutants that Preferentially Form Dimers and Resist Formation of Inactive Tetramers and Hexamers NM23 mutants that prefer dimer formation have been identified in human cancers. Some of these mutants resist the formation of tetramers and hexamers that do not bind to MUC1* and do not promote pluripotency. Mutants such as NM23-S20G prefer dimer formation over the wild type (wt) protein, but to obtain a solution in which a high concentration of hexamers does not induce differentiation, the S120G mutant is optionally denatured, refolded and the dimer fraction is purified using methods such as FPLC. Mutant NM23-P96S also prefers dimer formation and is more soluble when expressed as the recombinant protein than the S120G mutant. NM23 was generated by typical methods such that it contained the P96S mutation plus 0, 1, 2 or 6 amino acid deletions at the C-terminus FIG. 36 is an overlay of FPLC traces of the soluble fraction of the expression of the recombinant proteins. FIG. 36 shows that NM23-P96S plus 2 or 6 C-terminal deletions has significant fraction of NM23 in the dimeric form, suitable for MUC1* activation. Preferred is NM23-P96S plus 6 C-terminal deletions because it is predominantly in dimer form as the soluble protein.

Example 14

NM23 P96S and Deletion Constructs

We generated the NM23-H1 mutant P96S (proline #96 mutated to a serine) using the QuickChange site-directed mutagenesis kit (Agilent) following the manufacturer instructions using the following primers: 5'-tcggggagaccaactctgcagactccaag-3' (SEQ ID NO:45) and 5'-cttggagtctgcagagttggtctccccga-3' (SEQ ID NO:46). After sequence confirmation, the deletion constructs were generated by PCR. NM23 P96S ΔC1 was amplified using the following primers: 5'-atcgatcatatggccaactgtgagcgtaccttc-3' (SEQ ID NO:47) and 5'-gtggtgaccggtatagatccagttctgagcaca-3' (SEQ ID NO:48). NM23 P96S ΔC2 was amplified using the following primers: 5'-atcgatcatatggccaactgtgagcgtaccttc-3' (SEQ ID NO:49) and 5'-gtggtgaccggtgatccagttctgagcacagct-3' (SEQ ID NO:50). NM23 P96S ΔC6 was amplified using the following primers: 5'-atcgatcatatggccaactgtgagcgtaccttc-3' (SEQ ID NO:51) and 5'-gtggtgaccggtagcacagctcgtgtaatctacca-3' (SEQ ID NO:52). The resulting fragments were purified, digested (NdeI, AgeI) and cloned between NdeI and AgeI restriction sites of the expression vector pET21b. The pET21b was previously modified by replacing the XhoI restriction by AgeI.

After sequence confirmation, all constructs were transformed into BL21 (DE3) cells (New England Biolabs) for recombinant protein expression.

NM23 P96S - DNA sequence
(SEQ ID NO: 53)
atggccaactgtgagcgtaccttcattgcgatcaaaccagatggggtcca gcggggtcttgtgggagagattatcaagcgttttgagcagaaaggattcc gccttgttggtctgaaattcatgcaagcttccgaagatcttctcaaggaa cactacgttgacctgaaggaccgtccattctttgccggcctggtgaaata catgcactcagggccggtagttgccatggtctgggaggggctgaatgtgg tgaagacgggccgagtcatgctcggggagaccaactctgcagactccaag cctgggaccatccgtggagacttctgcatacaagttggcaggaacattat acatggcagtgattctgtggagagtgcagagaaggagatcggcttgtggt ttcaccctgaggaactggtagattacacgagctgtgctcagaactggatc tatgaactcgagcaccaccaccaccaccactga NM23 P96S - amino acid sequence
(SEQ ID NO: 54)
MANCERTFIAIKPDGVQRGLVGEIIKRFEQKGFRLVGLKFMQASEDLLKE

HYVDLKDRPFFAGLVKYMHSGPVVAMVWEGLNVVKTGRVMLGETNSADSK

PGTIRGDFCIQVGRNIIHGSDSVESAEKEIGLWFHPEELVDYTSCAQNWI

YELEHHHHHH

NM23 P96S ΔC2 - DNA sequence
(SEQ ID NO: 55)
atggccaactgtgagcgtaccttcattgcgatcaaaccagatggggtcca gcggggtcttgtgggagagattatcaagcgttttgagcagaaaggattcc gccttgttggtctgaaattcatgcaagcttccgaagatcttctcaaggaa cactacgttgacctgaaggaccgtccattctttgccggcctggtgaaata catgcactcagggccggtagttgccatggtctgggaggggctgaatgtgg tgaagacgggccgagtcatgctcggggagaccaactctgcagactccaag cctgggaccatccgtggagacttctgcatacaagttggcaggaacattat acatggcagtgattctgtggagagtgcagagaaggagatcggcttgtggt ttcaccctgaggaactggtagattacacgagctgtgctcagaactggatc accggtcaccaccaccaccactga NM23 P96S ΔC2 - amino acid sequence
(SEQ ID NO: 56)
MANCERTFIAIKPDGVQRGLVGEIIKRFEQKGFRLVGLKFMQASEDLLKE

HYVDLKDRPFFAGLVKYMHSGPVVAMVWEGLNVVKTGRVMLGETNSADSK

PGTIRGDFCIQVGRNIIHGSDSVESAEKEIGLWFHPEELVDYTSCAQNWI

TGHHHHHH

NM23 P96S ΔC6 - DNA sequence
(SEQ ID NO: 57)
atggccaactgtgagcgtaccttcattgcgatcaaaccagatggggtcca gcggggtcttgtgggagagattatcaagcgttttgagcagaaaggattcc gccttgttggtctgaaattcatgcaagcttccgaagatcttctcaaggaa cactacgttgacctgaaggaccgtccattctttgccggcctggtgaaata catgcactcagggccggtagttgccatggtctgggaggggctgaatgtgg tgaagacgggccgagtcatgctcggggagaccaactctgcagactccaag cctgggaccatccgtggagacttctgcatacaagttggcaggaacattat acatggcagtgattctgtggagagtgcagagaaggagatcggcttgtggt ttcaccctgaggaactggtagattacacgagctgtgctaccggtcaccac caccaccactga NM23 P96S ΔC6 - amino acid sequence
(SEQ ID NO: 58)
MANCERTFIAIKPDGVQRGLVGEIIKRFEQKGFRLVGLKFMQASEDLLKE

HYVDLKDRPFFAGLVKYMHSGPVVAMVWEGLNVVKTGRVMLGETNSADSK

PGTIRGDFCIQVGRNIIHGSDSVESAEKEIGLWFHPEELVDYTSCATGHH

HHHH

NM23 P96S ΔC1 - DNA sequence
(SEQ ID NO: 65)
atggccaactgtgagcgtaccttcattgcgatcaaaccagatggggtcca gcggggtcttgtgggagagattatcaagcgttttgagcagaaaggattcc gccttgttggtctgaaattcatgcaagcttccgaagatcttctcaaggaa cactacgttgacctgaaggaccgtccattctttgccggcctggtgaaata catgcactcagggccggtagttgccatggtctgggaggggctgaatgtgg tgaagacgggccgagtcatgctcggggagaccaactctgcagactccaag cctgggaccatccgtggagacttctgcatacaagttggcaggaacattat acatggcagtgattctgtggagagtgcagagaaggagatcggcttgtggt ttcaccctgaggaactggtagattacacgagctgtgctcagaactggatc tataccggtcaccaccaccaccactga NM23 P96S ΔC1 - amino acid sequence
(SEQ ID NO: 66)
MANCERTFIAIKPDGVQRGLVGEIIKRFEQKGFRLVGLKFMQASEDLLKE

HYVDLKDRPFFAGLVKYMHSGPVVAMVWEGLNVVKTGRVMLGETNSADSK

PGTIRGDFCIQVGRNIIHGSDSVESAEKEIGLWFHPEELVDYTSCAQNWI

YTGHHHHHH

Below is a comparative amino acid sequences of various NM23 variants.

```
NM23_S120G     MANCERTFIAIKPDGVQRGLVGEIIKRFEQKGFRLVGLKFMQASEDLLKEHYVDLKDRPF    60
NM23_P96S      MANCERTFIAIKPDGVQRGLVGEIIKRFEQKGFRLVGLKFMQASEDLLKEHYVDLKDRPF    60
NM23_P96S_01   MANCERTFIAIKPDGVQRGLVGEIIKRFEQKGFRLVGLKFMQASEDLLKEHYVDLKDRPF    60
NM23_P96S_02   MANCERTFIAIKPDGVQRGLVGEIIKRFEQKGFRLVGLKFMQASEDLLKEHYVDLKDRPF    60
NM23_P96S_06   MANCERTFIAIKPDGVQRGLVGEIIKRFEQKGFRLVGLKFMQASEDLLKEHYVDLKDRPF    60

NM23_S120G     FAGLVKYMHSGPVVAMVWEGLNVVKTGRVMLGETNPADSKPGTIRGDFCIQVGRNIIHGS   120
NM23_P96S      FAGLVKYMHSGPVVAMVWEGLNVVKTGRVMLGETNSADSKPGTIRGDFCIQVGRNIIHGS   120
NM23_P96S_01   FAGLVKYMHSGPVVAMVWEGLNVVKTGRVMLGETNSADSKPGTIRGDFCIQVGRNIIHGS   120
NM23_P96S_02   FAGLVKYMHSGPVVAMVWEGLNVVKTGRVMLGETNSADSKPGTIRGDFCIQVGRNIIHGS   120
NM23_P96S_06   FAGLVKYMHSGPVVAMVWEGLNVVKTGRVMLGETNSADSKPGTIRGDFCIQVGRNIIHGS   120
```

```
-continued
NM23_S120G    DSVESAEKEIGLWFHPEELVDYTSCAQNWIYELEHHHHHH-          160
NM23_P96S     DSVESAEKEIGLWFHPEELVDYTSCAQNWIYELEHHHHHH-          160
NM23_P96S_01  DSVESAEKEIGLWFHPEELVDYTSCAQNWIY░IGHHHHHH-          159
NM23_P96S_02  DSVESAEKEIGLWFHPEELVDYTSCAQNWI░░IGHHHHHH-          158
NM23_P96S_06  DSVESAEKEIGLWFHPEELVDYTSCA░░░░░░IGHHHHHH-          154
```

Example 15

Protein Expression/Purification

LB broth (Luria-Bertani broth) was inoculated with 1/10 of an overnight culture and cultured at 37° C. until OD600 reached ~0.5. At this point, recombinant protein expression was induced with 0.4 mM Isopropyl-β-D-thio-galactoside (IPTG, Sigma) and culture was stopped after 4 h. After harvesting the cells by centrifugation (6000 rpm for 10 min at 4° C.), cell pellet was resuspended with running buffer: PBS pH7.4, 360 mM NaCl and 80 mM imidazole. Then lysozyme (1 mg/mL, Sigma), MgCl$_2$ (0.5 mM) and DNAse (0.5 ug/mL, Sigma) were added. Cell suspension was incubated on a rotating platform (275 rpm) for 30 min at 37° C. and sonicated on ice for 5 min. Insoluble cell debris was removed by centrifugation (20000 rpm for 30 min at 4° C.). The cleared lysate was then applied to a Ni-NTA column (Qiagen) equilibrated with the running buffer. The column was washed (8CV) before eluting the protein off the column with the running buffer (6CV) supplemented with 420 mM imidazole. The proteins were further purified by size exclusion chromatography (Superdex 200).

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

---

What is claimed is:

1. An article comprising a stem cell proliferation surface without feeder layer, to which is bound an agent that binds to a cell surface molecule that is present on stem cells or progenitor cells, wherein the agent is monoclonal antibody that binds to PSMGFR, wherein the monoclonal antibody has the following Kappa Chain Variable Region CDR sequences:

```
CDR1: RSSQTIVHSNGNTYLE;    (SEQ ID NO: 20)

CDR2: KVSNRFS;             (SEQ ID NO: 21)
and

CDR3: FQGSHVPFT.           (SEQ ID NO: 22)
```

2. The article according to claim 1, wherein the surface comprises from at least about 0.5% Nitrogen (N), at least about a sum of Oxygen (O) and Nitrogen (N) of greater than or equal to 17.2%, and a contact angle of at least about 13.9 degrees.

3. The article according to claim 1, wherein the surface is Vita or Vita-like surface.

4. The article according to claim 1, wherein the cell surface molecule is MUC1.

5. The article according to claim 4, wherein the cell surface molecule is MUC1*.

6. The article according to claim 5, wherein the cell surface molecule is consists essentially of the PSMGFR sequence.

* * * * *

SEQUENCE LISTING

```
<160> NUMBER OF SEQ ID NOS: 66

<210> SEQ ID NO 1
<211> LENGTH: 1255
<212> TYPE: PRT
<213> ORGANISM: Artificial Sequence
<220> FEATURE:
<223> OTHER INFORMATION: Full-length MUC1 Receptor

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205
```

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
            645                 650                 655

Gly Val Thr Ser Ala Pro Asp Thr Arg Pro Ala Pro Gly Ser Thr Ala
        660                 665                 670

Pro Pro Ala His Gly Val Thr Ser Ala Pro Asp Thr Arg Pro Ala Pro
    675                 680                 685

Gly Ser Thr Ala Pro Pro Ala His Gly Val Thr Ser Ala Pro Asp Thr
690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
            725                 730                 735

Gly Val Thr Ser Ala Pro Asp Thr Arg Pro Ala Pro Gly Ser Thr Ala
        740                 745                 750

Pro Pro Ala His Gly Val Thr Ser Ala Pro Asp Thr Arg Pro Ala Pro
    755                 760                 765

Gly Ser Thr Ala Pro Pro Ala His Gly Val Thr Ser Ala Pro Asp Thr
770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
            805                 810                 815

Gly Val Thr Ser Ala Pro Asp Thr Arg Pro Ala Pro Gly Ser Thr Ala
        820                 825                 830

Pro Pro Ala His Gly Val Thr Ser Ala Pro Asp Thr Arg Pro Ala Pro
    835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
            885                 890                 895

Gly Val Thr Ser Ala Pro Asp Thr Arg Pro Ala Pro Gly Ser Thr Ala
        900                 905                 910

Pro Pro Ala His Gly Val Thr Ser Ala Pro Asp Thr Arg Pro Ala Pro
    915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
            965                 970                 975

Thr Ser Ala Arg Ala Thr Thr Thr Pro Ala Ser Lys Ser Thr Pro Phe
        980                 985                 990

Ser Ile Pro Ser His His Ser Asp Thr Pro Thr Thr Leu Ala Ser His
    995                 1000                1005

Ser Thr Lys Thr Asp Ala Ser Ser Thr His His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln

-continued

```
            1040                1045                1050
Phe Asn Ser Ser Leu Glu Asp Pro Ser Thr Asp Tyr Tyr Gln Glu
            1055                1060                1065

Leu Gln Arg Asp Ile Ser Glu Met Phe Leu Gln Ile Tyr Lys Gln
            1070                1075                1080

Gly Gly Phe Leu Gly Leu Ser Asn Ile Lys Phe Arg Pro Gly Ser
            1085                1090                1095

Val Val Val Gln Leu Thr Leu Ala Phe Arg Glu Gly Thr Ile Asn
            1100                1105                1110

Val His Asp Val Glu Thr Gln Phe Asn Gln Tyr Lys Thr Glu Ala
            1115                1120                1125

Ala Ser Arg Tyr Asn Leu Thr Ile Ser Asp Val Ser Val Ser Asp
            1130                1135                1140

Val Pro Phe Pro Phe Ser Ala Gln Ser Gly Ala Gly Val Pro Gly
            1145                1150                1155

Trp Gly Ile Ala Leu Leu Val Leu Val Cys Val Leu Val Ala Leu
            1160                1165                1170

Ala Ile Val Tyr Leu Ile Ala Leu Ala Val Cys Gln Cys Arg Arg
            1175                1180                1185

Lys Asn Tyr Gly Gln Leu Asp Ile Phe Pro Ala Arg Asp Thr Tyr
            1190                1195                1200

His Pro Met Ser Glu Tyr Pro Thr Tyr His Thr His Gly Arg Tyr
            1205                1210                1215

Val Pro Pro Ser Ser Thr Asp Arg Ser Pro Tyr Glu Lys Val Ser
            1220                1225                1230

Ala Gly Asn Gly Gly Ser Ser Leu Ser Tyr Thr Asn Pro Ala Val
            1235                1240                1245

Ala Ala Ala Ser Ala Asn Leu
            1250                1255

<210> SEQ ID NO 2
<211> LENGTH: 19
<212> TYPE: PRT
<213> ORGANISM: Artificial Sequence
<220> FEATURE:
<223> OTHER INFORMATION: N-terminal MUC-1 signaling sequence for
      directing MUC1 receptor and truncated isoforms to cell membrane
      surface

<400> SEQUENCE: 2

Met Thr Pro Gly Thr Gln Ser Pro Phe Phe Leu Leu Leu Leu Thr
1               5                   10                  15

Val Leu Thr

<210> SEQ ID NO 3
<211> LENGTH: 23
<212> TYPE: PRT
<213> ORGANISM: Artificial Sequence
<220> FEATURE:
<223> OTHER INFORMATION: N-terminal MUC-1 signaling sequence for
      directing MUC1 receptor and truncated isoforms to cell membrane
      surface

<400> SEQUENCE: 3

Met Thr Pro Gly Thr Gln Ser Pro Phe Phe Leu Leu Leu Leu Thr
1               5                   10                  15

Val Leu Thr Val Val Thr Ala
                20
```

```
<210> SEQ ID NO 4
<211> LENGTH: 23
<212> TYPE: PRT
<213> ORGANISM: Artificial Sequence
<220> FEATURE:
<223> OTHER INFORMATION: N-terminal MUC-1 signaling sequence for
      directing MUC1 receptor and truncated isoforms to cell membrane
      surface

<400> SEQUENCE: 4

Met Thr Pro Gly Thr Gln Ser Pro Phe Phe Leu Leu Leu Leu Leu Thr
1               5                   10                  15

Val Leu Thr Val Val Thr Gly
            20

<210> SEQ ID NO 5
<211> LENGTH: 146
<212> TYPE: PRT
<213> ORGANISM: Artificial Sequence
<220> FEATURE:
<223> OTHER INFORMATION: A truncated MUC1 receptor isoform having
      nat-PSMGFR at its N-terminus and including the transmembrane and
      cytoplasmic sequences of a full-length MUC1 receptor

<400> SEQUENCE: 5

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala Gly Val Pro
        35                  40                  45

Gly Trp Gly Ile Ala Leu Leu Val Leu Val Cys Val Leu Val Ala Leu
    50                  55                  60

Ala Ile Val Tyr Leu Ile Ala Leu Ala Val Cys Gln Cys Arg Arg Lys
65                  70                  75                  80

Asn Tyr Gly Gln Leu Asp Ile Phe Pro Ala Arg Asp Thr Tyr His Pro
                85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ala Ser Ala
    130                 135                 140

Asn Leu
145

<210> SEQ ID NO 6
<211> LENGTH: 171
<212> TYPE: PRT
<213> ORGANISM: Artificial Sequence
<220> FEATURE:
<223> OTHER INFORMATION: A truncated MUC1 receptor isoform having
      nat-PSMGFR and PSIBR at its N-terminus and including the
      transmembrane and cytoplasmic sequences of a full-length MUC1
      receptor

<400> SEQUENCE: 6

Gly Phe Leu Gly Leu Ser Asn Ile Lys Phe Arg Pro Gly Ser Val Val
1               5                   10                  15

Val Gln Leu Thr Leu Ala Phe Arg Glu Gly Thr Ile Asn Val His Asp
            20                  25                  30
```

Val Glu Thr Gln Phe Asn Gln Tyr Lys Thr Glu Ala Ala Ser Arg Tyr
              35                  40                  45

Asn Leu Thr Ile Ser Asp Val Ser Val Ser Asp Val Pro Phe Pro Phe
 50                  55                  60

Ser Ala Gln Ser Gly Ala Gly Val Pro Gly Trp Gly Ile Ala Leu Leu
65                   70                  75                  80

Val Leu Val Cys Val Leu Val Ala Leu Ala Ile Val Tyr Leu Ile Ala
                 85                  90                  95

Leu Ala Val Cys Gln Cys Arg Arg Lys Asn Tyr Gly Gln Leu Asp Ile
                100                 105                 110

Phe Pro Ala Arg Asp Thr Tyr His Pro Met Ser Glu Tyr Pro Thr Tyr
                115                 120                 125

His Thr His Gly Arg Tyr Val Pro Pro Ser Ser Thr Asp Arg Ser Pro
130                 135                 140

Tyr Glu Lys Val Ser Ala Gly Asn Gly Gly Ser Ser Leu Ser Tyr Thr
145                 150                 155                 160

Asn Pro Ala Val Ala Ala Ala Ser Ala Asn Leu
                165                 170

<210> SEQ ID NO 7
<211> LENGTH: 275
<212> TYPE: PRT
<213> ORGANISM: Artificial Sequence
<220> FEATURE:
<223> OTHER INFORMATION: A truncated MUC1 receptor isoform having
      nat-PSMGFR + PSIBR + Unique Region at its N-terminus and including
      the transmembrane and cytoplasmic sequences of a full-length MUC1
      receptor

<400> SEQUENCE: 7

Ala Thr Thr Thr Pro Ala Ser Lys Ser Thr Pro Phe Ser Ile Pro Ser
1               5                   10                  15

His His Ser Asp Thr Pro Thr Thr Leu Ala Ser His Ser Thr Lys Thr
                20                  25                  30

Asp Ala Ser Ser Thr His His Ser Thr Val Pro Pro Leu Thr Ser Ser
                35                  40                  45

Asn His Ser Thr Ser Pro Gln Leu Ser Thr Gly Val Ser Phe Phe Phe
 50                  55                  60

Leu Ser Phe His Ile Ser Asn Leu Gln Phe Asn Ser Ser Leu Glu Asp
65                   70                  75                  80

Pro Ser Thr Asp Tyr Tyr Gln Glu Leu Gln Arg Asp Ile Ser Glu Met
                85                  90                  95

Phe Leu Gln Ile Tyr Lys Gln Gly Gly Phe Leu Gly Leu Ser Asn Ile
                100                 105                 110

Lys Phe Arg Pro Gly Ser Val Val Val Gln Leu Thr Leu Ala Phe Arg
                115                 120                 125

Glu Gly Thr Ile Asn Val His Asp Val Glu Thr Gln Phe Asn Gln Tyr
130                 135                 140

Lys Thr Glu Ala Ala Ser Arg Tyr Asn Leu Thr Ile Ser Asp Val Ser
145                 150                 155                 160

Val Ser Asp Val Pro Phe Pro Phe Ser Ala Gln Ser Gly Ala Gly Val
                165                 170                 175

Pro Gly Trp Gly Ile Ala Leu Leu Val Leu Val Cys Val Leu Val Ala
                180                 185                 190

Leu Ala Ile Val Tyr Leu Ile Ala Leu Ala Val Cys Gln Cys Arg Arg
                195                 200                 205

-continued

```
Lys Asn Tyr Gly Gln Leu Asp Ile Phe Pro Ala Arg Asp Thr Tyr His
    210                 215                 220
Pro Met Ser Glu Tyr Pro Thr Tyr His Thr His Gly Arg Tyr Val Pro
225                 230                 235                 240
Pro Ser Ser Thr Asp Arg Ser Pro Tyr Glu Lys Val Ser Ala Gly Asn
                245                 250                 255
Gly Gly Ser Ser Leu Ser Tyr Thr Asn Pro Ala Val Ala Ala Ala Ser
                260                 265                 270
Ala Asn Leu
        275

<210> SEQ ID NO 8
<211> LENGTH: 233
<212> TYPE: PRT
<213> ORGANISM: Artificial Sequence
<220> FEATURE:
<223> OTHER INFORMATION: A truncated MUC1 receptor isoform including the
      transmembrane and cytoplasmic sequences of a full-length MUC1
      receptor

<400> SEQUENCE: 8

Gly Ser Gly His Ala Ser Ser Thr Pro Gly Gly Glu Lys Glu Thr Ser
1               5                   10                  15
Ala Thr Gln Arg Ser Ser Val Pro Ser Ser Thr Glu Lys Asn Ala Phe
                20                  25                  30
Asn Ser Ser Leu Glu Asp Pro Ser Thr Asp Tyr Tyr Gln Glu Leu Gln
            35                  40                  45
Arg Asp Ile Ser Glu Met Phe Leu Gln Ile Tyr Lys Gln Gly Gly Phe
50                  55                  60
Leu Gly Leu Ser Asn Ile Lys Phe Arg Pro Gly Ser Val Val Val Gln
65                  70                  75                  80
Leu Thr Leu Ala Phe Arg Glu Gly Thr Ile Asn Val His Asp Met Glu
                85                  90                  95
Thr Gln Phe Asn Gln Tyr Lys Thr Glu Ala Ala Ser Arg Tyr Asn Leu
                100                 105                 110
Thr Ile Ser Asp Val Ser Val Ser Asp Val Pro Phe Pro Phe Ser Ala
            115                 120                 125
Gln Ser Gly Ala Gly Val Pro Gly Trp Gly Ile Ala Leu Leu Val Leu
130                 135                 140
Val Cys Val Leu Val Ala Leu Ala Ile Val Tyr Leu Ile Ala Leu Ala
145                 150                 155                 160
Val Cys Gln Cys Arg Arg Lys Asn Tyr Gly Gln Leu Asp Ile Phe Pro
                165                 170                 175
Ala Arg Asp Thr Tyr His Pro Met Ser Glu Tyr Pro Thr Tyr His Thr
                180                 185                 190
His Gly Arg Tyr Val Pro Pro Ser Ser Thr Asp Arg Ser Pro Tyr Glu
            195                 200                 205
Lys Val Ser Ala Gly Asn Gly Gly Ser Ser Leu Ser Tyr Thr Asn Pro
210                 215                 220
Ala Val Ala Ala Thr Ser Ala Asn Leu
225                 230

<210> SEQ ID NO 9
<211> LENGTH: 863
<212> TYPE: PRT
<213> ORGANISM: Artificial Sequence
<220> FEATURE:
<223> OTHER INFORMATION: A truncated MUC1 receptor isoform having
``` nat-PSMGFR + PSIBR + Unique Region + Repeats at its N-terminus and
including the transmembrane and cytoplasmic sequences of a
full-length MUC1 receptor

<400> SEQUENCE: 9

```
Leu Asp Pro Arg Val Arg Thr Ser Ala Pro Asp Thr Arg Pro Ala Pro
1               5                   10                  15

Gly Ser Thr Ala Pro Gln Ala His Gly Val Thr Ser Ala Pro Asp Thr
            20                  25                  30

Arg Pro Ala Pro Gly Ser Thr Ala Pro Pro Ala His Gly Val Thr Ser
        35                  40                  45

Ala Pro Asp Thr Arg Pro Ala Pro Gly Ser Thr Ala Pro Pro Ala His
    50                  55                  60

Gly Val Thr Ser Ala Pro Asp Thr Arg Pro Ala Pro Gly Ser Thr Ala
65                  70                  75                  80

Pro Pro Ala His Gly Val Thr Ser Ala Pro Asp Thr Arg Pro Ala Pro
                85                  90                  95

Gly Ser Thr Ala Pro Pro Ala His Gly Val Thr Ser Ala Pro Asp Thr
            100                 105                 110

Arg Pro Ala Pro Gly Ser Thr Ala Pro Pro Ala His Gly Val Thr Ser
        115                 120                 125

Ala Pro Asp Thr Arg Pro Ala Pro Gly Ser Thr Ala Pro Pro Ala His
    130                 135                 140

Gly Val Thr Ser Ala Pro Asp Thr Arg Pro Ala Pro Gly Ser Thr Ala
145                 150                 155                 160

Pro Pro Ala His Gly Val Thr Ser Ala Pro Asp Thr Arg Pro Ala Pro
                165                 170                 175

Gly Ser Thr Ala Pro Pro Ala His Gly Val Thr Ser Ala Pro Asp Thr
            180                 185                 190

Arg Pro Ala Pro Gly Ser Thr Ala Pro Pro Ala His Gly Val Thr Ser
        195                 200                 205

Ala Pro Asp Thr Arg Pro Ala Pro Gly Ser Thr Ala Pro Pro Ala His
    210                 215                 220

Gly Val Thr Ser Ala Pro Asp Thr Arg Pro Ala Pro Gly Ser Thr Ala
225                 230                 235                 240

Pro Pro Ala His Gly Val Thr Ser Ala Pro Asp Thr Arg Pro Ala Pro
                245                 250                 255

Gly Ser Thr Ala Pro Pro Ala His Gly Val Thr Ser Ala Pro Asp Thr
            260                 265                 270

Arg Pro Ala Pro Gly Ser Thr Ala Pro Pro Ala His Gly Val Thr Ser
        275                 280                 285

Ala Pro Asp Thr Arg Pro Ala Pro Gly Ser Thr Ala Pro Pro Ala His
    290                 295                 300

Gly Val Thr Ser Ala Pro Asp Thr Arg Pro Ala Pro Gly Ser Thr Ala
305                 310                 315                 320

Pro Pro Ala His Gly Val Thr Ser Ala Pro Asp Thr Arg Pro Ala Pro
                325                 330                 335

Gly Ser Thr Ala Pro Pro Ala His Gly Val Thr Ser Ala Pro Asp Thr
            340                 345                 350

Arg Pro Ala Pro Gly Ser Thr Ala Pro Pro Ala His Gly Val Thr Ser
        355                 360                 365

Ala Pro Asp Thr Arg Pro Ala Pro Gly Ser Thr Ala Pro Pro Ala His
    370                 375                 380

Gly Val Thr Ser Ala Pro Asp Thr Arg Pro Ala Pro Gly Ser Thr Ala
```

```
            385                 390                 395                 400
Pro Pro Ala His Gly Val Thr Ser Ala Pro Asp Thr Arg Pro Ala Pro
                    405                 410                 415
Gly Ser Thr Ala Pro Pro Ala His Gly Val Thr Ser Ala Pro Asp Thr
                420                 425                 430
Arg Pro Ala Pro Gly Ser Thr Ala Pro Pro Ala His Gly Val Thr Ser
            435                 440                 445
Ala Pro Asp Thr Arg Pro Ala Pro Gly Ser Thr Ala Pro Pro Ala His
        450                 455                 460
Gly Val Thr Ser Ala Pro Asp Thr Arg Pro Ala Pro Gly Ser Thr Ala
465                 470                 475                 480
Pro Pro Ala His Gly Val Thr Ser Ala Pro Asp Thr Arg Pro Ala Pro
                    485                 490                 495
Gly Ser Thr Ala Pro Pro Ala His Gly Val Thr Ser Ala Pro Asp Thr
                500                 505                 510
Arg Pro Ala Pro Gly Ser Thr Ala Pro Pro Ala His Gly Val Thr Ser
            515                 520                 525
Ala Pro Asp Thr Arg Pro Ala Pro Gly Ser Thr Ala Pro Pro Ala His
        530                 535                 540
Gly Val Thr Ser Ala Pro Asp Asn Arg Pro Ala Leu Gly Ser Thr Ala
545                 550                 555                 560
Pro Pro Val His Asn Val Thr Ser Ala Ser Gly Ser Ala Ser Gly Ser
                    565                 570                 575
Ala Ser Thr Leu Val His Asn Gly Thr Ser Ala Arg Ala Thr Thr Thr
                580                 585                 590
Pro Ala Ser Lys Ser Thr Pro Phe Ser Ile Pro Ser His His Ser Asp
            595                 600                 605
Thr Pro Thr Thr Leu Ala Ser His Ser Thr Lys Thr Asp Ala Ser Ser
        610                 615                 620
Thr His His Ser Ser Val Pro Pro Leu Thr Ser Ser Asn His Ser Thr
625                 630                 635                 640
Ser Pro Gln Leu Ser Thr Gly Val Ser Phe Phe Leu Ser Phe His
                    645                 650                 655
Ile Ser Asn Leu Gln Phe Asn Ser Ser Leu Glu Asp Pro Ser Thr Asp
                660                 665                 670
Tyr Tyr Gln Glu Leu Gln Arg Asp Ile Ser Glu Met Phe Leu Gln Ile
            675                 680                 685
Tyr Lys Gln Gly Gly Phe Leu Gly Leu Ser Asn Ile Lys Phe Arg Pro
        690                 695                 700
Gly Ser Val Val Val Gln Leu Thr Leu Ala Phe Arg Glu Gly Thr Ile
705                 710                 715                 720
Asn Val His Asp Val Glu Thr Gln Phe Asn Gln Tyr Lys Thr Glu Ala
                    725                 730                 735
Ala Ser Arg Tyr Asn Leu Thr Ile Ser Asp Val Ser Val Ser Asp Val
                740                 745                 750
Pro Phe Pro Phe Ser Ala Gln Ser Gly Ala Gly Val Pro Gly Trp Gly
            755                 760                 765
Ile Ala Leu Leu Val Leu Val Cys Val Leu Val Ala Leu Ala Ile Val
        770                 775                 780
Tyr Leu Ile Ala Leu Ala Val Cys Gln Cys Arg Arg Lys Asn Tyr Gly
785                 790                 795                 800
Gln Leu Asp Ile Phe Pro Ala Arg Asp Thr Tyr His Pro Met Ser Glu
                    805                 810                 815
```

Tyr Pro Thr Tyr His Thr His Gly Arg Tyr Val Pro Ser Ser Thr
            820                 825                 830

Asp Arg Ser Pro Tyr Glu Lys Val Ser Ala Gly Asn Gly Ser Ser
        835                 840                 845

Leu Ser Tyr Thr Asn Pro Ala Val Ala Ala Ser Ala Asn Leu
    850                 855                 860

<210> SEQ ID NO 10
<211> LENGTH: 45
<212> TYPE: PRT
<213> ORGANISM: Artificial Sequence
<220> FEATURE:
<223> OTHER INFORMATION: Native Primary Sequence of the MUC1 Growth
      Factor Receptor

<400> SEQUENCE: 10

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 11
<211> LENGTH: 44
<212> TYPE: PRT
<213> ORGANISM: Artificial Sequence
<220> FEATURE:
<223> OTHER INFORMATION: Native Primary Sequence of the MUC1 Growth
      Factor Receptor

<400> SEQUENCE: 11

Thr Ile Asn Val His Asp Val Glu Thr Gln Phe Asn Gln Tyr Lys Thr
1               5                   10                  15

Glu Ala Ala Ser Arg Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 12
<211> LENGTH: 45
<212> TYPE: PRT
<213> ORGANISM: Artificial Sequence
<220> FEATURE:
<223> OTHER INFORMATION: "SPY" functional variant of the native Primary
      Sequence of the MUC1 Growth Factor Receptor having enhanced
      stability

<400> SEQUENCE: 12

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 13
<211> LENGTH: 44
<212> TYPE: PRT
<213> ORGANISM: Artificial Sequence
<220> FEATURE:
<223> OTHER INFORMATION: "SPY" functional variant of the native Primary
      Sequence of the MUC1 Growth Factor Receptor having enhanced stability

<400> SEQUENCE: 13

Thr Ile Asn Val His Asp Val Glu Thr Gln Phe Asn Gln Tyr Lys Thr
1               5                   10                  15

Glu Ala Ala Ser Pro Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 14
<211> LENGTH: 33
<212> TYPE: PRT
<213> ORGANISM: Artificial Sequence
<220> FEATURE:
<223> OTHER INFORMATION: Truncated PSMGFR receptor

<400> SEQUENCE: 14

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser

<210> SEQ ID NO 15
<211> LENGTH: 48
<212> TYPE: PRT
<213> ORGANISM: Artificial Sequence
<220> FEATURE:
<223> OTHER INFORMATION: Extended Sequence of MUC1 Growth Factor
      Receptor

<400> SEQUENCE: 15

Val Gln Leu Thr Leu Ala Phe Arg Glu Gly Thr Ile Asn Val His Asp
1               5                   10                  15

Val Glu Thr Gln Phe Asn Gln Tyr Lys Thr Glu Ala Ala Ser Pro Tyr
            20                  25                  30

Asn Leu Thr Ile Ser Asp Val Ser Val Ser Asp Val Pro Phe Pro Phe
        35                  40                  45

<210> SEQ ID NO 16
<211> LENGTH: 57
<212> TYPE: PRT
<213> ORGANISM: Artificial Sequence
<220> FEATURE:
<223> OTHER INFORMATION: Tumor-Specific Extended Sequence of MUC1 Growth
      Factor Receptor

<400> SEQUENCE: 16

Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Pro Tyr Asn Leu Thr Ile Ser Asp Val Ser Val Ser Asp Val Pro
        35                  40                  45

Phe Pro Phe Ser Ala Gln Ser Gly Ala
    50                  55

<210> SEQ ID NO 17
<211> LENGTH: 25
<212> TYPE: PRT
<213> ORGANISM: Artificial Sequence

```
<220> FEATURE:
<223> OTHER INFORMATION: Primary Sequence of the Interchain Binding
      Region

<400> SEQUENCE: 17

Gly Phe Leu Gly Leu Ser Asn Ile Lys Phe Arg Pro Gly Ser Val Val
1               5                   10                  15

Val Gln Leu Thr Leu Ala Phe Arg Glu
            20                  25

<210> SEQ ID NO 18
<211> LENGTH: 13
<212> TYPE: PRT
<213> ORGANISM: Artificial Sequence
<220> FEATURE:
<223> OTHER INFORMATION: Truncated Interchain Binding Region

<400> SEQUENCE: 18

Ser Val Val Val Gln Leu Thr Leu Ala Phe Arg Glu Gly
1               5                   10

<210> SEQ ID NO 19
<211> LENGTH: 40
<212> TYPE: PRT
<213> ORGANISM: Artificial Sequence
<220> FEATURE:
<223> OTHER INFORMATION: Repeat Motif 2

<400> SEQUENCE: 19

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
            20                  25                  30

Pro Ala His Gly Val Thr Ser Ala
            35                  40

<210> SEQ ID NO 20
<211> LENGTH: 16
<212> TYPE: PRT
<213> ORGANISM: Artificial Sequence
<220> FEATURE:
<223> OTHER INFORMATION: 2D6C3 Kappa Chain Variable Region - CDR1

<400> SEQUENCE: 20

Arg Ser Ser Gln Thr Ile Val His Ser Asn Gly Asn Thr Tyr Leu Glu
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: 2D6C3 Kappa Chain Variable Region - CDR2

<400> SEQUENCE: 21

Lys Val Ser Asn Arg Phe Ser
1               5

<210> SEQ ID NO 22
<211> LENGTH: 9
<212> TYPE: PRT
<213> ORGANISM: Artificial Sequence
<220> FEATURE:
<223> OTHER INFORMATION: 2D6C3 Kappa Chain Variable Region - CDR3

<400> SEQUENCE: 22
```

```
Phe Gln Gly Ser His Val Pro Phe Thr
1               5
```

<210> SEQ ID NO 23
<211> LENGTH: 5
<212> TYPE: PRT
<213> ORGANISM: Artificial Sequence
<220> FEATURE:
<223> OTHER INFORMATION: 2D6C3 Heavy Chain Variable Region - CDR1

<400> SEQUENCE: 23

```
Gly Tyr Ala Met Ser
1               5
```

<210> SEQ ID NO 24
<211> LENGTH: 17
<212> TYPE: PRT
<213> ORGANISM: Artificial Sequence
<220> FEATURE:
<223> OTHER INFORMATION: 2D6C3 Heavy Chain Variable Region - CDR2

<400> SEQUENCE: 24

```
Thr Ile Ser Ser Gly Gly Thr Tyr Ile Tyr Tyr Pro Asp Ser Val Lys
1               5                   10                  15

Gly
```

<210> SEQ ID NO 25
<211> LENGTH: 9
<212> TYPE: PRT
<213> ORGANISM: Artificial Sequence
<220> FEATURE:
<223> OTHER INFORMATION: 2D6C3 Heavy Chain Variable Region - CDR3

<400> SEQUENCE: 25

```
Leu Gly Gly Asp Asn Tyr Tyr Glu Tyr
1               5
```

<210> SEQ ID NO 26
<211> LENGTH: 15
<212> TYPE: PRT
<213> ORGANISM: Artificial Sequence
<220> FEATURE:
<223> OTHER INFORMATION: 2D6C8 Kappa Chain Variable Region - CDR1

<400> SEQUENCE: 26

```
Arg Ala Ser Lys Ser Val Ser Thr Ser Gly Tyr Ser Tyr Met His
1               5                   10                  15
```

<210> SEQ ID NO 27
<211> LENGTH: 7
<212> TYPE: PRT
<213> ORGANISM: Artificial Sequence
<220> FEATURE:
<223> OTHER INFORMATION: 2D6C8 Kappa Chain Variable Region - CDR2

<400> SEQUENCE: 27

```
Leu Val Ser Asn Leu Glu Ser
1               5
```

<210> SEQ ID NO 28
<211> LENGTH: 10
<212> TYPE: PRT
<213> ORGANISM: Artificial Sequence
<220> FEATURE:
<223> OTHER INFORMATION: 2D6C8 Kappa Chain Variable Region - CDR3

```
<400> SEQUENCE: 28

Gln His Ile Arg Glu Leu Thr Arg Ser Glu
1               5                   10

<210> SEQ ID NO 29
<211> LENGTH: 5
<212> TYPE: PRT
<213> ORGANISM: Artificial Sequence
<220> FEATURE:
<223> OTHER INFORMATION: 2D6C8 Heavy Chain Variable Region - CDR1

<400> SEQUENCE: 29

Gly Tyr Ala Met Ser
1               5

<210> SEQ ID NO 30
<211> LENGTH: 17
<212> TYPE: PRT
<213> ORGANISM: Artificial Sequence
<220> FEATURE:
<223> OTHER INFORMATION: 2D6C8 Heavy Chain Variable Region - CDR2

<400> SEQUENCE: 30

Thr Ile Ser Ser Gly Gly Thr Tyr Ile Tyr Tyr Pro Asp Ser Val Lys
1               5                   10                  15
Gly

<210> SEQ ID NO 31
<211> LENGTH: 9
<212> TYPE: PRT
<213> ORGANISM: Artificial Sequence
<220> FEATURE:
<223> OTHER INFORMATION: 2D6C8 Heavy Chain Variable Region - CDR3

<400> SEQUENCE: 31

Leu Gly Gly Asp Asn Tyr Tyr Glu Tyr
1               5

<210> SEQ ID NO 32
<211> LENGTH: 15
<212> TYPE: PRT
<213> ORGANISM: Artificial Sequence
<220> FEATURE:
<223> OTHER INFORMATION: 3C2B1 Kappa Chain Variable Region - CDR1

<400> SEQUENCE: 32

Arg Ala Ser Lys Ser Ile Ser Thr Ser Asp Tyr Asn Tyr Ile His
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: 3C2B1 Kappa Chain Variable Region - CDR2

<400> SEQUENCE: 33

Leu Ala Ser Asn Leu Glu Ser
1               5

<210> SEQ ID NO 34
<211> LENGTH: 10
<212> TYPE: PRT
<213> ORGANISM: Artificial Sequence
<220> FEATURE:
<223> OTHER INFORMATION: 3C2B1 Kappa Chain Variable Region - CDR3
```

<400> SEQUENCE: 34

Gln His Ser Arg Glu Leu Pro Leu Thr Phe
1               5                   10

<210> SEQ ID NO 35
<211> LENGTH: 5
<212> TYPE: PRT
<213> ORGANISM: Artificial Sequence
<220> FEATURE:
<223> OTHER INFORMATION: 3C2B1 Heavy Chain Variable Region - CDR1

<400> SEQUENCE: 35

Thr Tyr Thr Met Ser
1               5

<210> SEQ ID NO 36
<211> LENGTH: 17
<212> TYPE: PRT
<213> ORGANISM: Artificial Sequence
<220> FEATURE:
<223> OTHER INFORMATION: 3C2B1 Heavy Chain Variable Region - CDR2

<400> SEQUENCE: 36

Thr Ile Ser Thr Gly Gly Asp Lys Thr Tyr Tyr Ser Asp Ser Val Lys
1               5                   10                  15

Gly

<210> SEQ ID NO 37
<211> LENGTH: 10
<212> TYPE: PRT
<213> ORGANISM: Artificial Sequence
<220> FEATURE:
<223> OTHER INFORMATION: 3C2B1 Heavy Chain Variable Region - CDR3

<400> SEQUENCE: 37

Gly Thr Thr Ala Met Tyr Tyr Tyr Ala Met
1               5                   10

<210> SEQ ID NO 38
<211> LENGTH: 34
<212> TYPE: DNA
<213> ORGANISM: Artificial Sequence
<220> FEATURE:
<223> OTHER INFORMATION: Primer for WT NM23-H1 cDNA

<400> SEQUENCE: 38
atcgatggat ccgatggcca actgtgagcg tacc                           34

<210> SEQ ID NO 39
<211> LENGTH: 33
<212> TYPE: DNA
<213> ORGANISM: Artificial Sequence
<220> FEATURE:
<223> OTHER INFORMATION: Primer for WT NM23-H1 cDNA

<400> SEQUENCE: 39
gtggtgctcg agttcataga tccagttctg agc                            33

<210> SEQ ID NO 40
<211> LENGTH: 30
<212> TYPE: DNA
<213> ORGANISM: Artificial Sequence
<220> FEATURE:
<223> OTHER INFORMATION: Primer for NM23-H1 mutant S120G

<400> SEQUENCE: 40

```
gcaggaacat tatacatggc ggtgattctg                                30
```

<210> SEQ ID NO 41
<211> LENGTH: 30
<212> TYPE: DNA
<213> ORGANISM: Artificial Sequence
<220> FEATURE:
<223> OTHER INFORMATION: Primer for NM23-H1 mutant S120G

<400> SEQUENCE: 41

```
gccatgtata atgttcctgc caacttgtat                                30
```

<210> SEQ ID NO 42
<211> LENGTH: 483
<212> TYPE: DNA
<213> ORGANISM: Artificial Sequence
<220> FEATURE:
<223> OTHER INFORMATION: NM23 S120G

<400> SEQUENCE: 42

```
atggccaact gtgagcgtac cttcattgcg atcaaaccag atggggtcca gcggggtctt    60
gtgggagaga ttatcaagcg ttttgagcag aaaggattcc gccttgttgg tctgaaattc   120
atgcaagctt ccgaagatct tctcaaggaa cactacgttg acctgaagga ccgtccattc   180
tttgccggcc tggtgaaata catgcactca gggccggtag ttgccatggt ctgggagggg   240
ctgaatgtgg tgaagacggg ccgagtcatg ctcggggaga ccaaccctgc agactccaag   300
cctgggacca tccgtggaga cttctgcata caagttggca ggaacattat acatggcggt   360
gattctgtgg agagtgcaga gaaggagatc ggcttgtggt ttcaccctga ggaactggta   420
gattacacga gctgtgctca gaactggatc tatgaactcg agcaccacca ccaccaccac   480
tga                                                                483
```

<210> SEQ ID NO 43
<211> LENGTH: 160
<212> TYPE: PRT
<213> ORGANISM: Artificial Sequence
<220> FEATURE:
<223> OTHER INFORMATION: NM23 S120G

<400> SEQUENCE: 43

```
Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Gly Asp Ser Val Glu Ser Ala Glu Lys
        115                 120                 125

Glu Ile Gly Leu Trp Phe His Pro Glu Glu Leu Val Asp Tyr Thr Ser
```

Cys Ala Gln Asn Trp Ile Tyr Glu Leu Glu His His His His His
145                 150                 155                 160

<210> SEQ ID NO 44
<211> LENGTH: 41
<212> TYPE: PRT
<213> ORGANISM: Artificial Sequence
<220> FEATURE:
<223> OTHER INFORMATION: MUC1*ecd peptide

<400> SEQUENCE: 44

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala His His His His His His
        35                  40

<210> SEQ ID NO 45
<211> LENGTH: 29
<212> TYPE: DNA
<213> ORGANISM: Artificial Sequence
<220> FEATURE:
<223> OTHER INFORMATION: Primer for NM23-H1 mutant P96S

<400> SEQUENCE: 45
tcggggagac caactctgca gactccaag                                    29

<210> SEQ ID NO 46
<211> LENGTH: 29
<212> TYPE: DNA
<213> ORGANISM: Artificial Sequence
<220> FEATURE:
<223> OTHER INFORMATION: Primer for NM23-H1 mutant P96S

<400> SEQUENCE: 46
cttggagtct gcagagttgg tctccccga                                    29

<210> SEQ ID NO 47
<211> LENGTH: 33
<212> TYPE: DNA
<213> ORGANISM: Artificial Sequence
<220> FEATURE:
<223> OTHER INFORMATION: Primer for NM23 P96S C1

<400> SEQUENCE: 47
atcgatcata tggccaactg tgagcgtacc ttc                               33

<210> SEQ ID NO 48
<211> LENGTH: 33
<212> TYPE: DNA
<213> ORGANISM: Artificial Sequence
<220> FEATURE:
<223> OTHER INFORMATION: Primer for NM23 P96S C1

<400> SEQUENCE: 48
gtggtgaccg gtatagatcc agttctgagc aca                               33

<210> SEQ ID NO 49
<211> LENGTH: 33
<212> TYPE: DNA
<213> ORGANISM: Artificial Sequence
<220> FEATURE:
<223> OTHER INFORMATION: Primer for NM23 P96S C2

<400> SEQUENCE: 49
atcgatcata tggccaactg tgagcgtacc ttc                                33

<210> SEQ ID NO 50
<211> LENGTH: 33
<212> TYPE: DNA
<213> ORGANISM: Artificial Sequence
<220> FEATURE:
<223> OTHER INFORMATION: Primer for NM23 P96S C2

<400> SEQUENCE: 50
gtggtgaccg gtgatccagt tctgagcaca gct                                33

<210> SEQ ID NO 51
<211> LENGTH: 33
<212> TYPE: DNA
<213> ORGANISM: Artificial Sequence
<220> FEATURE:
<223> OTHER INFORMATION: Primer for NM23 P96S C6

<400> SEQUENCE: 51
atcgatcata tggccaactg tgagcgtacc ttc                                33

<210> SEQ ID NO 52
<211> LENGTH: 35
<212> TYPE: DNA
<213> ORGANISM: Artificial Sequence
<220> FEATURE:
<223> OTHER INFORMATION: Primer for NM23 P96S C6

<400> SEQUENCE: 52
gtggtgaccg gtagcacagc tcgtgtaatc tacca                              35

<210> SEQ ID NO 53
<211> LENGTH: 483
<212> TYPE: DNA
<213> ORGANISM: Artificial Sequence
<220> FEATURE:
<223> OTHER INFORMATION: NM23 P96S

<400> SEQUENCE: 53
atggccaact gtgagcgtac cttcattgcg atcaaaccag atggggtcca gcggggtctt    60
gtgggagaga ttatcaagcg ttttgagcag aaaggattcc gccttgttgg tctgaaattc   120
atgcaagctt ccgaagatct tctcaaggaa cactacgttg acctgaagga ccgtccattc   180
tttgccggcc tggtgaaata catgcactca gggccgtag ttgccatggt ctgggagggg    240
ctgaatgtgg tgaagacggg ccgagtcatg ctcggggaga ccaactctgc agactccaag   300
cctgggacca tccgtggaga cttctgcata caagttggca ggaacattat acatggcagt   360
gattctgtgg agagtgcaga gaaggagatc ggcttgtggt ttcaccctga ggaactggta   420
gattacacga gctgtgctca gaactggatc tatgaactcg agcaccacca ccaccaccac   480
tga                                                                483

<210> SEQ ID NO 54
<211> LENGTH: 160
<212> TYPE: PRT
<213> ORGANISM: Artificial Sequence
<220> FEATURE:
<223> OTHER INFORMATION: NM23 P96S

<400> SEQUENCE: 54

-continued

```
Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
        50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Ser
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
            115                 120                 125

Glu Ile Gly Leu Trp Phe His Pro Glu Glu Leu Val Asp Tyr Thr Ser
        130                 135                 140

Cys Ala Gln Asn Trp Ile Tyr Glu Leu Glu His His His His His His
145                 150                 155                 160
```

<210> SEQ ID NO 55
<211> LENGTH: 477
<212> TYPE: DNA
<213> ORGANISM: Artificial Sequence
<220> FEATURE:
<223> OTHER INFORMATION: NM23 P96S C2

<400> SEQUENCE: 55

```
atggccaact gtgagcgtac cttcattgcg atcaaaccag atggggtcca gcggggtctt      60
gtgggagaga ttatcaagcg ttttgagcag aaaggattcc gccttgttgg tctgaaattc     120
atgcaagctt ccgaagatct tctcaaggaa cactacgttg acctgaagga ccgtccattc     180
tttgccggcc tggtgaaata catgcactca gggccggtag ttgccatggt ctgggagggg     240
ctgaatgtgg tgaagacggg ccgagtcatg ctcggggaga ccaactctgc agactccaag     300
cctgggacca tccgtggaga cttctgcata caagttggca ggaacattat acatggcagt     360
gattctgtgg agagtgcaga gaaggagatc ggcttgtggt ttcaccctga ggaactggta     420
gattacacga gctgtgctca gaactggatc accggtcacc accaccacca ccactga       477
```

<210> SEQ ID NO 56
<211> LENGTH: 158
<212> TYPE: PRT
<213> ORGANISM: Artificial Sequence
<220> FEATURE:
<223> OTHER INFORMATION: NM23 P96S C2

<400> SEQUENCE: 56

```
Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
        50                  55                  60

Val Lys Tyr Met His Ser Gly Pro Val Val Ala Met Val Trp Glu Gly
```

```
                65                  70                  75                  80
Leu Asn Val Val Lys Thr Gly Arg Val Met Leu Gly Glu Thr Asn Ser
                    85                  90                  95

Ala Asp Ser Lys Pro Gly Thr Ile Arg Gly Asp Phe Cys Ile Gln Val
                100                 105                 110

Gly Arg Asn Ile Ile His Gly Ser Asp Ser Val Glu Ser Ala Glu Lys
            115                 120                 125

Glu Ile Gly Leu Trp Phe His Pro Glu Glu Leu Val Asp Tyr Thr Ser
130                 135                 140

Cys Ala Gln Asn Trp Ile Thr Gly His His His His His His
145                 150                 155

<210> SEQ ID NO 57
<211> LENGTH: 465
<212> TYPE: DNA
<213> ORGANISM: Artificial Sequence
<220> FEATURE:
<223> OTHER INFORMATION: NM23 P96S C6

<400> SEQUENCE: 57
atggccaact gtgagcgtac cttcattgcg atcaaaccag atggggtcca gcggggtctt     60
gtgggagaga ttatcaagcg ttttgagcag aaaggattcc gccttgttgg tctgaaattc    120
atgcaagctt ccgaagatct tctcaaggaa cactacgttg acctgaagga ccgtccattc    180
tttgccggcc tggtgaaata catgcactca gggccggtag ttgccatggt ctggaggggg    240
ctgaatgtgg tgaagacggg ccgagtcatg ctcggggaga ccaactctgc agactccaag    300
cctgggacca tccgtggaga cttctgcata caagttggca ggaacattat acatggcagt    360
gattctgtgg agagtgcaga gaaggagatc ggcttgtggt ttcaccctga ggaactggta    420
gattacacga gctgtgctac cggtcaccac caccaccacc actga                    465

<210> SEQ ID NO 58
<211> LENGTH: 154
<212> TYPE: PRT
<213> ORGANISM: Artificial Sequence
<220> FEATURE:
<223> OTHER INFORMATION: NM23 P96S C6

<400> SEQUENCE: 58

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
                20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
        50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Ser
                    85                  90                  95

Ala Asp Ser Lys Pro Gly Thr Ile Arg Gly Asp Phe Cys Ile Gln Val
                100                 105                 110

Gly Arg Asn Ile Ile His Gly Ser Asp Ser Val Glu Ser Ala Glu Lys
            115                 120                 125

Glu Ile Gly Leu Trp Phe His Pro Glu Glu Leu Val Asp Tyr Thr Ser
130                 135                 140
```

```
Cys Ala Thr Gly His His His His His His
145                 150

<210> SEQ ID NO 59
<211> LENGTH: 102
<212> TYPE: PRT
<213> ORGANISM: Artificial Sequence
<220> FEATURE:
<223> OTHER INFORMATION: 2D6C3 Kappa Chain Variable Region

<400> SEQUENCE: 59

Asp Ile Val Ile Thr Gln Thr Pro Leu Ser Leu Pro Val Ser Leu Gly
1               5                   10                  15

Asp Gln Ala Ser Ile Ser Cys Arg Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Phe Thr
            100

<210> SEQ ID NO 60
<211> LENGTH: 107
<212> TYPE: PRT
<213> ORGANISM: Artificial Sequence
<220> FEATURE:
<223> OTHER INFORMATION: 2D6C3 Heavy Chain Variable Region

<400> SEQUENCE: 60

Glu Val Met Val Val Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Leu Gly Gly Asp Asn Tyr Tyr Glu Tyr
            100                 105

<210> SEQ ID NO 61
<211> LENGTH: 102
<212> TYPE: PRT
<213> ORGANISM: Artificial Sequence
<220> FEATURE:
<223> OTHER INFORMATION: 2D6C8 Kappa Chain Variable Region

<400> SEQUENCE: 61

Asp Ile Val Ile Thr Gln Thr Pro Ala Ser Leu Ala Val Ser Leu Gly
1               5                   10                  15
```

Gln Arg Ala Thr Ile Ser Tyr Arg Ala Ser Lys Ser Val Thr Ser
            20                  25                  30

Gly Tyr Ser Tyr Met His Trp Asn Gln Lys Pro Gly Gln Pro Pro
            35                  40                  45

Arg Leu Leu Ile Tyr Leu Val Ser Asn Leu Glu Ser Gly Val Pro Ala
50                      55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu
            100

<210> SEQ ID NO 62
<211> LENGTH: 107
<212> TYPE: PRT
<213> ORGANISM: Artificial Sequence
<220> FEATURE:
<223> OTHER INFORMATION: 2D6C8 Heavy Chain Variable Region

<400> SEQUENCE: 62

Glu Val Met Val Val Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Leu Gly Gly Asp Asn Tyr Tyr Glu Tyr
            100                 105

<210> SEQ ID NO 63
<211> LENGTH: 102
<212> TYPE: PRT
<213> ORGANISM: Artificial Sequence
<220> FEATURE:
<223> OTHER INFORMATION: 3C2B1 Kappa Chain Variable Region

<400> SEQUENCE: 63

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Ile Ser Thr Ser
            20                  25                  30

Asp Tyr Asn Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe
            100

<210> SEQ ID NO 64
<211> LENGTH: 108
<212> TYPE: PRT
<213> ORGANISM: Artificial Sequence
<220> FEATURE:
<223> OTHER INFORMATION: 3C2B1 Heavy Chain Variable Region

<400> SEQUENCE: 64

Glu Val Met Leu Val Glu Ser Gly Gly Gly Leu Val Lys Pro Gly Gly
1               5                   10                  15

Ser Leu Lys Leu Ser Cys Ala Ala Ser Gly Ile Thr Phe Ser Thr Tyr
            20                  25                  30

Thr Met Ser Trp Val Arg Gln Thr Pro Glu Lys Arg Leu Glu Trp Val
        35                  40                  45

Ala Thr Ile Ser Thr Gly Gly Asp Lys Thr Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Gly Thr Thr Ala Met Tyr Tyr Tyr Ala Met
            100                 105

<210> SEQ ID NO 65
<211> LENGTH: 480
<212> TYPE: DNA
<213> ORGANISM: Artificial Sequence
<220> FEATURE:
<223> OTHER INFORMATION: NM23 P96S C1

<400> SEQUENCE: 65
atggccaact gtgagcgtac cttcattgcg atcaaaccag atggggtcca gcggggtctt      60
gtgggagaga ttatcaagcg ttttgagcag aaaggattcc gccttgttgg tctgaaattc     120
atgcaagctt ccgaagatct tctcaaggaa cactacgttg acctgaagga ccgtccattc     180
tttgccggcc tggtgaaata catgcactca gggccggtag ttgccatggt ctgggagggg     240
ctgaatgtgg tgaagacggg ccgagtcatg ctcggggaga ccaactctgc agactccaag     300
cctgggacca tccgtggaga cttctgcata caagttggca ggaacattat acatggcagt     360
gattctgtgg agagtgcaga gaaggagatc ggcttgtggt ttcaccctga ggaactggta     420
gattacacga gctgtgctca gaactggatc tataccggtc accaccacca ccaccactga     480

<210> SEQ ID NO 66
<211> LENGTH: 159
<212> TYPE: PRT
<213> ORGANISM: Artificial Sequence
<220> FEATURE:
<223> OTHER INFORMATION: NM23 P96S C1

<400> SEQUENCE: 66

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

-continued

```
Val Lys Tyr Met His Ser Gly Pro Val Val Ala Met Val Trp Glu Gly
 65              70                  75                  80

Leu Asn Val Val Lys Thr Gly Arg Val Met Leu Gly Glu Thr Asn Ser
                 85                  90                  95

Ala Asp Ser Lys Pro Gly Thr Ile Arg Gly Asp Phe Cys Ile Gln Val
            100             105                 110

Gly Arg Asn Ile Ile His Gly Ser Asp Ser Val Glu Ser Ala Glu Lys
        115             120                 125

Glu Ile Gly Leu Trp Phe His Pro Glu Glu Leu Val Asp Tyr Thr Ser
    130             135                 140

Cys Ala Gln Asn Trp Ile Tyr Thr Gly His His His His His
145                 150                 155
```